(12) United States Patent
Eggert et al.

(10) Patent No.: US 9,870,720 B2
(45) Date of Patent: *Jan. 16, 2018

(54) INTERACTIVE EDUCATION SYSTEM FOR TEACHING PATIENT CARE

(71) Applicant: Gaumard Scientific Company, Inc., Miami, FL (US)

(72) Inventors: John S. Eggert, Miami, FL (US); Michael S. Eggert, Norfolk, VA (US); Alberto Rodriguez, Miami, FL (US)

(73) Assignee: Gaumard Scientific Company, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/193,422

(22) Filed: Jun. 27, 2016

(65) Prior Publication Data

US 2016/0372009 A1    Dec. 22, 2016

Related U.S. Application Data

(63) Continuation of application No. 14/614,581, filed on Feb. 5, 2015, now Pat. No. 9,378,659, which is a continuation of application No. 13/863,210, filed on Apr. 15, 2013, now Pat. No. 8,951,047, which is a continuation of application No. 13/223,020, filed on
(Continued)

(51) Int. Cl.
*G09B 23/28* (2006.01)
*G06F 19/00* (2011.01)

(52) U.S. Cl.
CPC ....... *G09B 23/281* (2013.01); *G06F 19/3437* (2013.01); *G09B 23/28* (2013.01)

(58) Field of Classification Search
USPC ........ 434/267, 268, 272, 273; 446/320, 330, 446/353
See application file for complete search history.

(56) References Cited

U.S. PATENT DOCUMENTS

| 2,551,433 A | 5/1951 | Graves |
| 2,871,579 A | 2/1959 | Niiranen et al. |

(Continued)

FOREIGN PATENT DOCUMENTS

| DE | 20221862 U1 | 1/2007 |
| FR | 2448368 A1 | 9/1980 |

(Continued)

OTHER PUBLICATIONS

Allen, R. H., "Simulating Birth to Investigate Clinician-Applied Loads on Newborns," National Library of Medicine MEDLINE Database, Jul. 1995, 1 page.
(Continued)

*Primary Examiner* — Kurt Fernstrom
(74) *Attorney, Agent, or Firm* — Haynes and Boone, LLP

(57) ABSTRACT

Simulator systems for teaching patient care are provided. In some instances, the simulator system includes a maternal simulator sized and shaped to simulate a pregnant woman, the maternal simulator including a torso, arms, legs, and a head, wherein the torso includes a chamber sized and shaped to receive a fetal simulator and wherein a birthing mechanism is disposed within the chamber for providing rotational and translational movement to the fetal simulator in a birthing simulation; and a fetal simulator sized and shaped to simulate a fetus, the fetal simulator configured to be selectively engaged with the birthing mechanism of the maternal simulator.

18 Claims, 43 Drawing Sheets

Related U.S. Application Data

Aug. 31, 2011, now Pat. No. 8,419,438, which is a continuation of application No. 11/952,559, filed on Dec. 7, 2007, now Pat. No. 8,016,598, which is a continuation-in-part of application No. 11/538,306, filed on Oct. 3, 2006, now Pat. No. 7,811,090.

(56) References Cited

U.S. PATENT DOCUMENTS

| | | | |
|---|---|---|---|
| 3,125,826 A | 3/1964 | Ostrander |
| 3,154,881 A | 11/1964 | Elwell |
| 3,520,071 A | 7/1970 | Abrahamson et al. |
| 3,605,580 A | 9/1971 | Miller |
| 3,557,471 A | 1/1972 | Payne et al. |
| 3,641,703 A | 2/1972 | Tepper et al. |
| 3,664,038 A | 5/1972 | Searle et al. |
| 3,707,762 A | 1/1973 | Alderson |
| 3,740,871 A | 6/1973 | Berton et al. |
| 3,753,301 A | 8/1973 | Daniel et al. |
| 3,797,130 A | 3/1974 | Knapp et al. |
| 3,818,756 A | 6/1974 | Barron et al. |
| 3,822,486 A | 7/1974 | Knapp et al. |
| 3,824,709 A | 7/1974 | Knapp et al. |
| 3,826,019 A | 7/1974 | Knapp et al. |
| 3,866,350 A | 2/1975 | Goldfarb et al. |
| 3,905,130 A | 9/1975 | Gordon et al. |
| 3,916,535 A | 11/1975 | Hewson |
| 4,067,138 A | 1/1978 | Cederholm et al. |
| 4,134,218 A | 1/1979 | Adams et al. |
| 4,155,196 A | 5/1979 | Bollinger et al. |
| 4,237,649 A | 12/1980 | Goldfarb et al. |
| 4,360,345 A | 11/1982 | Hon |
| 4,395,235 A | 7/1983 | Becker |
| 4,402,327 A | 9/1983 | Lambert et al. |
| 4,430,893 A | 2/1984 | Barkalow |
| 4,464,123 A | 8/1984 | Glover et al. |
| 4,575,351 A | 3/1986 | Gonzalez |
| 4,611,998 A | 9/1986 | Ramamurthy |
| 4,691,556 A | 9/1987 | Mellander et al. |
| 4,701,132 A | 10/1987 | Groesch et al. |
| 4,734,039 A | 3/1988 | Thompson |
| 4,734,074 A | 3/1988 | Kinberg et al. |
| 4,773,866 A | 9/1988 | Baldwin |
| 4,797,104 A | 1/1989 | Laerdal et al. |
| 4,820,236 A | 4/1989 | Berliner et al. |
| 4,828,501 A | 5/1989 | Ingenito et al. |
| 4,836,821 A | 6/1989 | Raymond |
| 4,843,497 A | 6/1989 | Leyden |
| 4,850,876 A | 7/1989 | Lutaenko et al. |
| 4,865,552 A | 9/1989 | Maloney et al. |
| 4,867,685 A | 9/1989 | Brush et al. |
| 4,907,973 A | 3/1990 | Hon |
| 4,915,635 A | 4/1990 | Ingenito et al. |
| 4,923,428 A | 5/1990 | Curran |
| 4,932,879 A | 6/1990 | Ingenito et al. |
| 5,055,052 A | 10/1991 | Johnsen |
| 5,083,962 A | 1/1992 | Pracas |
| 5,100,329 A | 3/1992 | Deesen et al. |
| 5,104,328 A | 4/1992 | Lounsbury |
| 5,137,458 A | 8/1992 | Ungs et al. |
| 5,137,459 A | 8/1992 | Zirm |
| 5,195,896 A | 3/1993 | Sweeney et al. |
| 5,259,765 A | 11/1993 | Richards |
| 5,279,309 A | 1/1994 | Taylor et al. |
| 5,295,835 A | 3/1994 | Schelnberg et al. |
| 5,351,677 A | 10/1994 | Kami et al. |
| 5,385,474 A | 1/1995 | Brindle |
| 5,441,413 A | 8/1995 | Kumar |
| 5,454,722 A | 10/1995 | Holland et al. |
| 5,509,810 A | 4/1996 | Schertz et al. |
| 5,528,943 A | 6/1996 | Smrcka et al. |
| 5,538,005 A | 7/1996 | Harrison et al. |
| 5,540,592 A | 7/1996 | Scheinberg et al. |
| 5,584,701 A | 12/1996 | Lampotang et al. |
| 5,609,485 A | 3/1997 | Bergman et al. |
| 5,620,326 A | 4/1997 | Younker |
| 5,628,230 A | 5/1997 | Flam |
| 5,704,791 A | 1/1998 | Gillio |
| 5,755,577 A | 5/1998 | Gillio |
| 5,769,640 A | 6/1998 | Jacobus et al. |
| 5,769,641 A | 6/1998 | Lampotang et al. |
| 5,772,443 A | 6/1998 | Lampotang et al. |
| 5,779,484 A | 7/1998 | Lampotang et al. |
| 5,799,282 A | 8/1998 | Rakshit et al. |
| 5,800,179 A | 9/1998 | Bailey |
| 5,828,197 A | 10/1998 | Martin et al. |
| 5,853,292 A | 12/1998 | Eggert et al. |
| 5,855,553 A | 1/1999 | Tajima et al. |
| 5,882,206 A | 3/1999 | Gillo |
| 5,900,923 A | 5/1999 | Prendergast et al. |
| 5,941,757 A | 8/1999 | Jurmain et al. |
| 6,022,263 A | 2/2000 | Liu et al. |
| 6,024,576 A | 2/2000 | Bivert et al. |
| 6,042,450 A | 3/2000 | Leversedge et al. |
| 6,050,826 A | 4/2000 | Christianson et al. |
| 6,077,083 A | 6/2000 | Smith-Whitley et al. |
| 6,088,017 A | 7/2000 | Tremblay et al. |
| 6,088,020 A | 7/2000 | Mor |
| 6,089,873 A | 7/2000 | Jurmain et al. |
| 6,091,981 A | 7/2000 | Cundari et al. |
| 6,113,395 A | 9/2000 | Hon |
| 6,117,078 A | 9/2000 | Lysyanskyt et al. |
| 6,126,450 A | 10/2000 | Mukai et al. |
| 6,193,519 B1 | 2/2001 | Eggert et al. |
| 6,219,032 B1 | 4/2001 | Rosenberg et al. |
| 6,220,866 B1 | 4/2001 | Amend et al. |
| 6,230,574 B1 | 5/2001 | Rider et al. |
| 6,267,599 B1 | 7/2001 | Bailey |
| 6,273,728 B1 | 8/2001 | van Meurs et al. |
| 6,296,490 B1 | 10/2001 | Bowden |
| 6,306,107 B1 | 10/2001 | Myklebust et al. |
| 6,375,471 B1 | 4/2002 | Wendlandt et al. |
| 6,428,321 B1 | 8/2002 | Jurmain et al. |
| 6,443,735 B1 | 9/2002 | Eggert et al. |
| 6,470,302 B1 | 10/2002 | Cunningham et al. |
| 6,503,087 B1 | 1/2003 | Eggert et al. |
| 6,527,558 B1 | 3/2003 | Eggert et al. |
| 6,544,041 B1 | 4/2003 | Damadian |
| 6,547,782 B1 | 4/2003 | Taylor |
| 6,575,757 B1 | 6/2003 | Leight et al. |
| 6,638,073 B1 | 10/2003 | Kazimirov et al. |
| 6,669,483 B1 | 12/2003 | Leight et al. |
| 6,705,871 B1 | 3/2004 | Bevirt et al. |
| 6,758,676 B2 | 7/2004 | Eggert et al. |
| 6,850,222 B1 | 2/2005 | Rosenberg |
| 6,857,878 B1 | 2/2005 | Chosack et al. |
| 6,923,081 B2 | 8/2005 | Krstic |
| 6,929,481 B1 | 8/2005 | Alexander et al. |
| 6,946,812 B1 | 9/2005 | Martin et al. |
| 6,957,961 B1 | 10/2005 | Owens et al. |
| 6,997,718 B1 | 2/2006 | Boettcher et al. |
| 7,114,954 B2 | 10/2006 | Eggert et al. |
| 7,192,284 B2 | 3/2007 | Eggert et al. |
| 7,241,145 B2 | 7/2007 | Riener et al. |
| 7,465,168 B2 | 12/2008 | Allen et al. |
| 7,485,025 B2 | 2/2009 | Schnuckle |
| 8,382,485 B2 | 2/2013 | Bardsley et al. |
| 2003/0073060 A1 | 4/2003 | Eggert et al. |
| 2004/0110117 A1 | 6/2004 | van Oostrom et al. |
| 2004/0157199 A1 | 8/2004 | Eggert et al. |
| 2004/0234933 A1 | 11/2004 | Dawson et al. |
| 2007/0122785 A1 | 5/2007 | Eggert et al. |
| 2007/0172804 A1 | 7/2007 | Allen et al. |
| 2008/0131855 A1 | 6/2008 | Eggert et al. |
| 2008/0138778 A1 | 6/2008 | Eggert et al. |
| 2008/0138779 A1 | 6/2008 | Eggert et al. |
| 2008/0138780 A1 | 6/2008 | Eggert et al. |
| 2009/0148822 A1 | 6/2009 | Eggert et al. |

FOREIGN PATENT DOCUMENTS

| | | |
|---|---|---|
| FR | 2554360 A1 | 5/1985 |
| GB | 2324902 | 4/1998 |
| JP | 5528028 | 2/1980 |

(56) References Cited

FOREIGN PATENT DOCUMENTS

| | | |
|---|---|---|
| JP | 63011018 | 2/1985 |
| JP | 60030769 | 3/1985 |
| JP | 63080180 | 4/1988 |
| JP | 04008447 | 1/1992 |
| WO | WO-1996/016389 | 5/1996 |
| WO | WO-2002/001536 | 1/2002 |
| WO | WO-2002/029765 | 4/2002 |
| WO | WO-2003/041034 | 5/2003 |
| WO | WO 2004/030599 A2 | 4/2004 |
| WO | WO-2005/032327 | 4/2005 |
| WO | WO-2005/053508 | 6/2005 |
| WO | WO-2005/122111 | 12/2005 |
| WO | WO-2008/042931 | 4/2006 |
| WO | WO-2009/076145 | 12/2008 |

OTHER PUBLICATIONS

American Heart Association CPR and Advanced Cardiac Life Support Learning System, Fighting Heart Disease and Stroke, American Heart Association.
Armstrong 1996, Anesthesia Emergency Code Team, METI, EMS Respiratory ICU/CCU, 15 pages.
Brett, P. N., "A Technique for Measuring Contact Force Distribution in Minimally Invasive Surgical Procedures," National Library of Medicine MEDLINE Database, 1997, 1 page.
Crofts, Joanna F., et al., "Training for Shoulder Dystocia," Obstetrics & Gynecology, vol. 108, No. 6, Dec. 2006, p. 1477-1485.
Easy ACLS Quick reference Chart 2, Advanced Cardiac Life Support Preparation Manual, 1995, 11 pages.
European Patent Office, Office Action dated Nov. 22, 2005, Application No. 2009/143583, 5 pages.
European Patent Office, International Search Report dated Feb. 28, 2006, for Application No. PCT/US07/080252, 3 pages.
European Patent Office, Office Action dated Nov. 22, 2005, Application No. 01977908.1, 4 pages.
European Patent Office, Office Action dated Jul. 8, 2014, Application No. 08860019.2, 5 pages.
European Patent Office, "Notification of Transmittal of the International Search Report and the Written Opinion of the International Searching Authority, or the Declaration," PCT/US2008/085471, Jul. 16, 2009, 23 pages.
Gaumard Scientific 2002-2003 Catalogue, 88 pages.
Gaumard Scientific 95-96 Catalogue, 2 pages.
Helping Save Lives, Laerdal Catalogue, 1992, 10 pages.
Human Patient Simulator, Clinical Features Summary, Medical Education Technology, 2002-2003, 11 pages.
International Search Report and Written Opinion for PCT/US2004/39409, dated Oct. 24, 2005, 9 pages.
International Search Report for PCT/US2007/080252, dated Feb. 28, 2008.
Japanese Patent Office, Office Action dated Dec. 8, 2009, Application No. 2009/143583, 5 pages.
John S. Eggert, Michael S. Eggert and Alberto Rodriguez, U.S. Appl. No. 11/952,606, filed Dec. 7, 2007 for "Interactive Education System for Teaching Patient Care".
John S. Eggert, Michael S. Eggert, Alberto Rodriguez, U.S. Appl. No. 11/952,636, filed Dec. 7, 2007 for "Interactive Education System for Teaching Patient Care".
John S. Eggert, Michael S. Eggert, Alberto Rodriguez and Miguel Carvajal, U.S. Appl. No. 11/952,669, filed Dec. 7, 2007 for "Interactive Education System for Teaching Patient Care".
John S. Eggert, Michael S. Eggert and Ning Jiang, U.S. Appl. No. 11/952,698, filed Dec. 7, 2007 for "Interactive Education System for Teaching Patient Care".
Lifesaving Products for Today's Good Samaritans, Laerdal Catalogue, 2003, 7 pages.
Loral Data Physiology, Pharmacology & Technology Together in the Human Patient Simulator, Aug. 1994, 8 pages.
Loral Data Systems Delivers Human patient Simulator, news release, Aug. 1994, 1 page.
Loral Data Physiology, Pharmacology & Technology Together in the Human Patient, Simulator, Mar. 1994, 3 pages.
Medical Educational Technology, Human Patient Simulator, 1996, 9 pages.
Medical Testing Taxes Leap into Future, newspaper article, Nov. 8, 1994, 2 pages.
METI, Practice is the Best Teacher Brochure, 1997, 4 pages.
METI, The Biggest Smallest Innovation, Pediasim Simulation Technology, 1999, 4 pages.
Nasco Health Care Educational Materials. 1996-1997 catalogue, 23 pages.
Noelle Maternal and Neonatal Birthing Simulator Product Promotional Information, 2002, 16 pages.
Promotional Literature, Advanced Cardiac Life Support Learning System, Ambu MegaCode Trainer System and Ambu Defib Training Manikin, May 1996, 9 pages.
Putting It All Together, Laerded ALS Trainer Product Information, 2 pages.
University or Miami, Division of Research in Medical Education. "Harvey"—The Cardiology Patient Simulator, 5 pages.
www.laedal.com, Early Defibrillation Products, Laerdal AED Trainer and Laerdal Early Defibrillation Training Manikins, Nov. 16, 1998, 2 pages.
European Patent Office, "Examination Report" for Application No. 07 843 710.0 1952, dated Jan. 31, 2017, 4 pages.
International Searching Authority/European Patent Office, "Communication—European Search Report," for European Application No. 13 163 909.8, dated Aug. 1, 2016, 8 pages.

Fig. 16

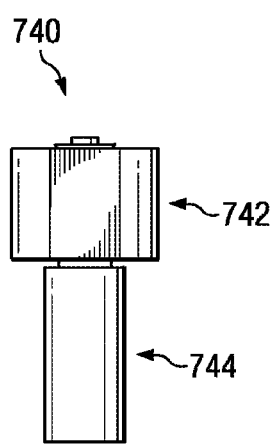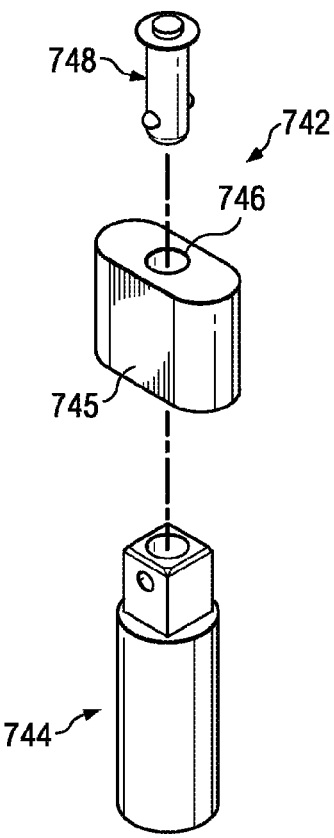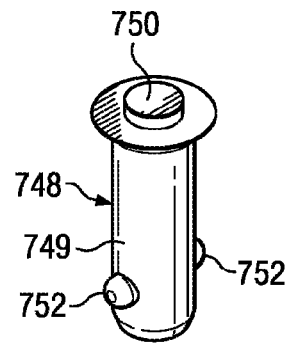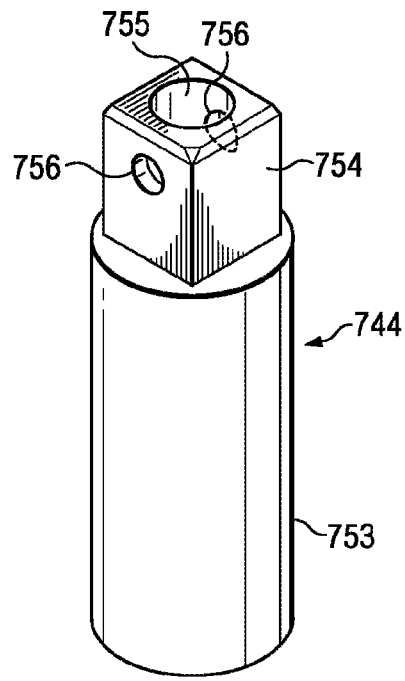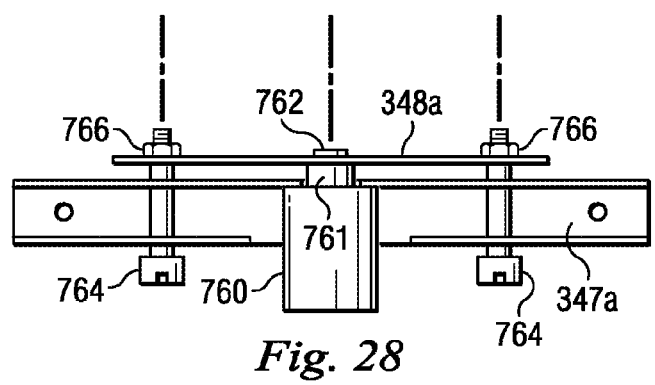
Fig. 24
Fig. 25
Fig. 26
Fig. 27
Fig. 28

INTERACTIVE EDUCATION SYSTEM FOR TEACHING PATIENT CARE

CROSS-REFERENCE TO RELATED APPLICATION

This application is a continuation of U.S. application Ser. No. 14/614,581, filed Feb. 5, 2015, now U.S. Pat. No. 9,378,659, which is a continuation of U.S. application Ser. No. 13/863,210, filed on Apr. 15, 2013, now U.S. Pat. No. 8,951,047, which is a continuation of U.S. application Ser. No. 13/223,020 filed on Aug. 31, 2011, now U.S. Pat. No. 8,419,438, which is a continuation of U.S. application Ser. No. 11/952,559 filed on Dec. 7, 2007, now U.S. Pat. No. 8,016,598, which is a continuation-in-part of U.S. application Ser. No. 11/538,306 filed on Oct. 3, 2006, now U.S. Pat. No. 7,811,090, each of which is hereby incorporated by reference in its entirety.

Further, in some embodiments the present disclosure is configured for use with the patient simulators and systems described in U.S. patent application Ser. No. 11/952,363, now U.S. Pat. No. 7,976,312, filed Dec. 7, 2007; U.S. patent application Ser. No. 11/952,606, filed Dec. 7, 2007; U.S. patent application Ser. No. 11/952,669, filed Dec. 7, 2007; U.S. patent application Ser. No. 11/952,698, now U.S. Pat. No. 7,976,313, filed Dec. 7, 2007, each herein incorporated by reference in its entirety. Further, U.S. patent application Ser. No. 10/848,991, now U.S. Pat. No. 7,114,954, filed on May 19, 2004; U.S. patent application Ser. No. 10/292,193, now U.S. Pat. No. 6,758,676, filed on Nov. 11, 2002; U.S. patent application Ser. No. 09/684,030, now U.S. Pat. No. 6,503,087, filed on Oct. 6, 2000; U.S. patent application Ser. No. 09/640,700, now U.S. Pat. No. 6,527,558, filed Aug. 17, 2000; U.S. patent application Ser. No. 09/560,949, now U.S. Pat. No. 6,443,735, filed Apr. 28, 2000; U.S. patent application Ser. No. 09/199,599, now U.S. Pat. No. 6,193,519, filed Nov. 25, 1998; and U.S. patent application Ser. No. 08/643,435, now U.S. Pat. No. 5,853,292, filed May 8, 1996 are each hereby incorporated by reference in their entirety.

BACKGROUND

The present embodiment relates generally to an interactive education system for teaching patient care, and more particularly to such a system having virtual instruments for use with a child birthing patient simulator in conducting patient care activity.

While it is desirable to train students in patient care protocols before allowing contact with real patients, textbooks and flash cards lack the important benefit to students attained from "hands-on" practice. Thus, patient care education has often been taught using medical instruments to perform patient care activity on a simulator, such as a manikin. However, one disadvantage of such a system is that medical instruments are often prohibitively expensive, and consequently, many users must settle for using a smaller variety of instruments, even at the cost of a less comprehensive educational experience. One solution to the foregoing problem is using a set of relatively inexpensive, simulated medical instruments ("virtual" instruments), as taught in U.S. Pat. No. 5,853,292, the entire disclosure of which is hereby incorporated by reference. Another solution is for the simulators to be compatible with real medical instruments.

Another problem in patient care education is that the patient simulators used for teaching a user are generally passive. For example, in a child birthing simulation, a user must position the simulated fetus in a simulated maternal pelvis, move it down the birth canal, birth the fetus's head, rotate the fetus approximately ninety degrees to birth the shoulders, and finally, pull out the fetus, now referred to as a neonate. While replicating the sequence of events in a real delivery, the lack of verisimilitude resulting from physical manipulation of the fetus by the user undermines an appreciation for the difficulties of providing patient care. In a real delivery, the fetus is inaccessible, and most activity is obscured from view, and thus prior systems fail to address the most challenging conditions of providing patient care during child birthing. Moreover, prior systems fail to simulate cervical dilation as the fetus moves down the birth canal, thus failing to allow a student to assess the stage of delivery or construct a chart of cervical dilation versus time to assess the progress of delivery ("Partograph").

Further, another problem in patient care education is that often the systems are too bulky and require too many wired connections to other components, which prevents easy transportation of the simulator to other locations. Often systems that claim to be "portable" require moving the numerous attached components, such as compressors and power supplies, for the simulator to be fully-functional. A solution to this problem is to make the simulators fully-functional, self-contained simulators that communicate with external devices wirelessly. Therefore, what is needed is a system for an interactive education system for use in conducting patient care training sessions that includes a more realistic simulated patient(s).

SUMMARY

The present embodiment provides an interactive education system for teaching patient care to a user. The system includes a maternal simulator, a fetal simulator designed to be used both in conjunction with the maternal simulator and separate from the maternal simulator, and neonatal simulator designed to replace the fetal simulator in post-birth simulations. In some embodiments, the system includes simulators that are completely tetherless. That is, the simulator is functional without the need for wired connections to other external instruments, devices, or power supplies. In such embodiments, the simulator may communicate with other devices or instruments wirelessly.

In some embodiments, a newborn simulator for teaching patient care is provided. The simulator includes a body having one or more simulated body portions sized to simulate a newborn baby. A head portion is movably connected to a portion of the body. A simulated heart and simulated lungs are positioned at least partially within the body. The simulator is operable to provide a simulated heart beat and respiratory pattern. Also, the simulator is operable without physical connection to an external device.

In some embodiments, a method of teaching patient care is provided. The method includes providing a medical simulator including a model of at least a portion of a human body. The simulator is configured to execute a simulated medical scenario. The method also includes defining a plurality of palette items, each of the plurality of palette items associated with a physiological state of the simulator, and defining at least one scenario, the at least one scenario including a series of linked palette items. The method also includes selecting a scenario for execution by the simulator, communicating the selected scenario to the simulator, and utilizing the simulator to execute the selected scenario.

In some embodiments, a patient simulator for teaching patient care is provided. The patient simulator includes a patient body comprising one or more simulated body portions and a pair of bladders positioned within the patient body for simulating a patient's lungs. A compressor is positioned within the patient body in communication with the bladders for selectively providing an air supply to the bladders to simulate a respiratory pattern. A master module is also positioned within the patient body and configured for communication with an external control system. A respiratory module system is positioned within the patient body and spaced from the master module. The respiratory module system controls the respiratory pattern of the patient simulator by controlling the air supply to and from the bladders. The patient simulator is operable without physical connection to an external device.

In some embodiments, a patient simulator for teaching patient care is provided. The simulator includes a patient body simulating at least a portion of a patient's anatomy. A master module is positioned within the patient body. The master module is configured for communication with an external control system. In that regard, the master module is configured to receive simulation commands from the external control system and relay the simulation commands to a plurality of task modules positioned within the patient body but spaced from the master module. The simulator also includes the plurality of task modules configured to execute the simulation commands received from the master module.

In some embodiments, an eye assembly for use in a patient simulator is provided. The eye assembly includes an iris diaphragm having a moveable inner portion defining an opening. The inner portion of the iris diaphragm is movable radially from a first position wherein the opening has a first diameter and a second position wherein the opening has a second diameter greater than the first diameter. The iris diaphragm is configured for use in a simulated eye. The eye assembly also includes a dilation actuator in communication with the inner portion of the iris diaphragm for selectively moving the inner portion between the first and second positions to simulate dilation of an eye.

In some embodiments, a patient simulator system for teaching patient care is provided. The system includes a patient simulator. The patient simulator includes a patient body comprising one or more simulated body portions. A respiratory system is positioned within the patient body. The respiratory system includes a pair of lungs and is configured to simulate a respiratory pattern of a patient. A circulatory system is also positioned within the patient body. The circulatory system is configured to simulate at least one circulatory parameter of the patient. The system also includes a control system in communication with the patient simulator. The control system includes a respiratory physiological model for controlling the simulated respiratory pattern of the respiratory system and a circulatory physiological model for controlling the at least one circulatory parameter of the circulatory system. The respiratory physiological model is configured to adjust the simulated respiratory pattern of the respiratory system at least partially based on a treatment administered to the patient simulator by a user.

In some embodiments, a patient simulator system for teaching patient care is provided. The system includes a maternal simulator comprising one or more simulated body portions, a fetal simulator positioned within the maternal simulator, and a control system in communication with the maternal and fetal simulators. The control system is configured for controlling simulated physical parameters of the maternal simulator and the fetal simulator. In that regard, parameters of the fetal simulator are at least partially based on parameters of the maternal simulator.

BRIEF DESCRIPTION OF THE DRAWINGS

FIGS. 12-16 are screen display views generated by a program according to one embodiment of the present system.

FIG. 24 is a front view of a mechanism for securing the fetal/neonatal simulator to the maternal simulator according to one embodiment of the present disclosure.

FIG. 25 is a perspective, exploded view of the mechanism of FIG. 24.

FIG. 26 is a perspective view of a portion of the mechanism of FIG. 24.

FIG. 27 is a perspective view of another portion of the mechanism of FIG. 24.

FIG. 28 is a side view of a system for causing selective rotation of the fetal/neonatal simulator during a birthing simulation.

DETAILED DESCRIPTION

Figure 1A:
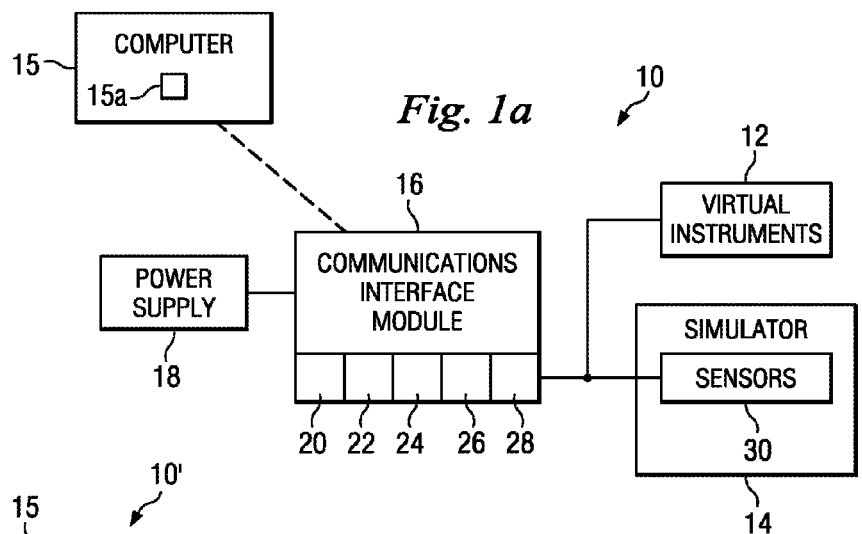
FIG. 1a is a schematic view of an illustrative embodiment of an interactive education system.

Referring to FIG. 1a, the reference numeral 10 refers, in general, to an interactive education system for teaching patient care protocols to a user. The system 10 comprises a set of virtual instruments 12 used to simulate medical instruments, and a simulator 14 used to simulate at least one patient for receiving patient care activity from the user. The virtual instruments 12 are tangible objects, and look, feel, and operate like real medical devices in conjunction with the simulator 14, which is understood to encompass a variety of forms, including a fully articulating and adult-sized manikin, as well as a fetus, a neonate, a child, a youth, or portion of a manikin, such as the arm, torso, head, or pelvic region.

Patient care activity received by the simulator 14 from the user, or users, is sensed in a manner to be described, and in response to the activity, the system 10 provides feedback to the user. It is understood that feedback may comprise any audio, visual, or tactile response. A computer 15 having a program 15a is optionally connected to the system 10, for reasons to be described.

Figure 1B:
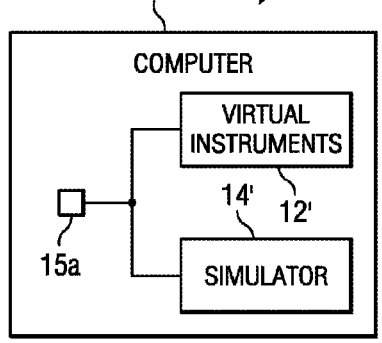
FIG. 1b is a schematic view of an interactive education system according to another embodiment.

Referring to FIG. 1b, a system 10' comprises the computer 15 and the program 15a, wherein a software-generated set of virtual instruments 12' and a software-generated simulator 14' is provided. Thus, the patient care activity performed by the user comprises manipulating an icon relating to a selected software-generated virtual instrument 12' to provide patient care to the software-generated simulator 14'. In this embodiment, the program 15a uses conventional means, such as clicking a mouse or voice-activated software, to monitor activity by the user, and provides feedback in response, as will be described.

Returning to FIG. 1a, the system 10 further comprises a communications interface module ("CIM") 16, which receives operating power from a conventional power source 18, and contains a microcontroller ("PIC") 20. Microcontrollers are available from many vendors, such as Microchip Technology, Inc. (Chandler, Ariz.), and are then customized. As will be described, the PIC 20 receives input signals from the user's activity, and is programmed to respond in a certain manner to provide feedback to the user. For example, to provide audio feedback, the CIM 16 additionally includes an audio chip 22 which is responsive to the PIC 20 for causing a speaker 24 to produce realistic patient sounds, for example, heart, lung, blood pressure (Korotkoff), intestinal, fetal, and the like. A control 26 is included in the CIM 16 for adjusting the volume of the speaker 24.

Alternatively, depending on the complexity of the desired feedback, the CIM 16 may be connected to the computer 15 and program 15a. In one example of feedback, the program 15a could be used to provide a vast library, for example, of ultrasound profiles, or fetal distress monitor traces. Feedback could also be of body sounds, generated by the program 15a, and played through speakers of the computer.

The CIM 16 has a plurality of ports, collectively 28, for receiving input signals occasioned by interaction between the virtual instruments 12 and sensors 30 disposed on the simulator 14, resulting from the user's patient care activity. It is understood that there may be more than one PIC 20, and more than one CIM 16, to manage the input signals thus created.

Figure 2:
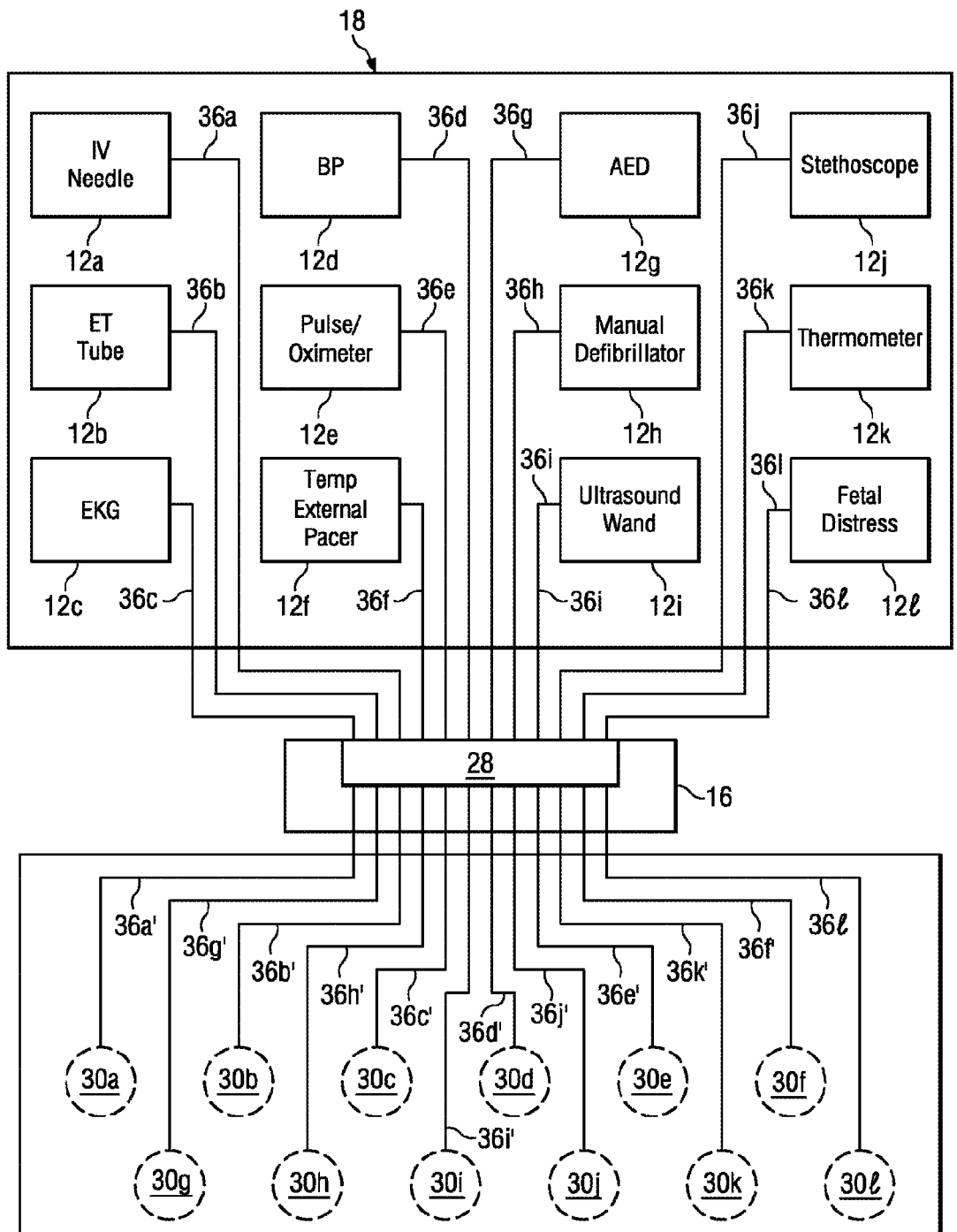
FIG. 2 is a schematic view of the interaction between a set of virtual instruments and a patient simulator.

The virtual instruments 12 comprise patient care devices, for example, as shown in FIG. 2, at least one IV needle, an endotracheal (ET) tube, an electrocardiogram (ECG or EKG) monitor, a blood pressure (BP) cuff, a pulse oximeter cuff, a temporary external pacer, an automatic external defibrillator (AED), a manual defibrillator, an ultrasound wand, a virtual stethoscope, a thermometer, and a fetal distress monitor, respectively 12a-1. Such virtual instruments look and operate like real medical devices. Of course, other virtual instruments are contemplated, as is the use of relatively inexpensive medical devices, such as a conventional stethoscope, a vacuum extractor, catheters, trays, IV stands, and the like.

Referring to FIG. 2, the IV needle 12*a* has a selectable group of specific drugs and dosages, and in one embodiment is part of a medication tray with an assortment of labeled syringes for dispensing the drugs to the simulator 14, with the effects of administration controlled by the program 15*a*. The ET tube 12*b* is used in simulated patient airway management, and placed in a tracheal airway of the simulator 14. The EKG monitor 12*c* comprises a 3, 5, or 12 lead system, including a real-time trace monitor and R-wave sonic markers, and a plurality of color-coded patches for attachment to a torso of the simulator 14. The BP cuff 12*d* attaches to the simulator 14, for example, around an arm. The pulse oximeter finger cuff 12*e* attaches to the simulator 14, for example, around a finger. The temporary external pacer 12*f* has a plurality of anterior and posterior pacer pads for attachment to the torso of the simulator 14. The pacer 12*f* has controls for pacer rate and current, and exhibits rhythm pacing, cap time, and loss of cap time, all of which is controlled by the program 15*a*. The automatic external defibrillator (AED) 12*g* has a plurality of apex and sternum AED pads for attachment to the torso of the simulator 14. Upon selecting a software-generated shock button produced by the program 15*a*, the system 10 simulates defibrillation shock, with the resultant conditions controlled by the program 15*a*. The manual defibrillator 12*h* has a plurality of apex and sternum defibrillator paddles for contacting the torso of the simulator 14. Upon selecting a software-generated shock button, or alternatively by using a dual shock buttons associated with manual defibrillator 12*h*, the system 10 simulates defibrillation shock, with the resultant conditions controlled by the program 15*a*.

Still referring to FIG. 2, the ultrasound wand 12*i* interacts with the simulator 14, such that when the wand 30*i* is brought within a predetermined proximity of a predetermined anatomical area of the simulator, the CIM 16 detects the interaction and the program 15*a* supplies an ultrasound profile taken from a library of ultrasound images and or sounds. The program 15*a* may select between normal and abnormal profiles, requiring the user to interpret the profile and respond accordingly. The virtual stethoscope 12*j* interacts with the simulator 14, such that when the stethoscope 12*j* is brought within a predetermined proximity of a predetermined anatomical area of the simulator, the CIM 16 detects the interaction and feedback is supplied to the user, as will be explained below, with FIGS. 3*a-b*. The thermometer 12*k* interacts with the simulator 14, such that when the thermometer 12*k* is brought within a predetermined proximity of a predetermined anatomical area of the simulator, the CIM detects the interaction and the program 15*a* supplies a temperature reading. The fetal distress monitor 12*l* (tocodynomometer) attaches to a portion of the simulator 14, and upon attachment, the program 15*a* supplies a heart rate reading for a simulated fetus.

Each instrument has a corresponding sensor 30*a-1*, as indicated by lines, collectively 36. Unless otherwise indicated, the lines 36 are schematic, and merely illustrate that the virtual instruments 12 and the sensors 30 are functionally connected to each other for providing an interaction created by the user's patient care activity, the interaction being reported as an input signal to the CIM 16. It is understood that the sharing of such physical lines among instruments 12, or sensors 30, is contemplated as well.

Interaction between the virtual instruments 12 and the sensors 30 may be electrical, optical, pressure differential, tactile, temperature-controlled, or wireless. Generally speaking, an electrical interaction (which would also provide the input signal) could be created via a virtual instrument 12 having one node and a sensor 30 with another node, both of which are physically connected to the CIM 16, or by a virtual instrument with two nodes and a sensor formed of conductive material, or vice versa, only one of which may be physically connected to the CIM 16. For example, the IV needle 12*a* corresponds with a portion of the simulator 14 capable of accepting medications, such as the antecubital region of an arm, which may have a sensor 30*a* comprising an insulator sandwiched between two layers of conductive material having an appropriate thickness and weave density for permitting the needle 12*a* to pass through the cloth at a low acute angle (e.g., 20□). The conductive layers of the sensor 30*a* are electrically coupled to the CIM 16 via line 36*a*', such that when the needle 12*a* is correctly passed through the two conductive layers, simulating cannulation of a vein of the simulator 14, a circuit is completed between the layers and sensed by the CIM 16.

In another example of a method of sensing interaction, the ET tube 12*b* is used in simulated patient airway management, the simulator 14 having a head, eyes, a nose, a mouth, and a realistic airway capable of accepting conventional airway adjuncts, with the airway configuration adjustable to display a large tongue, an obstructed pharynx, or closed vocal cords, to increase the difficulty of the patient care activity. In order to confirm proper placement in the tracheal airway of the simulator 14, an optical sensor 30*b* is mounted in the wall of the trachea of the simulator 14 and connected to the CIM 16 via line 36*b*'. Correct placement of the ET tube 12*b* in the trachea is confirmed when the tip of the ET tube interrupts the beam of the optical sensor 30*b*. The sensor 30*b* may also be used to determine whether a fluid has passed.

The virtual stethoscope 12*j* provides an example of a wireless method of sensing interaction. At least one sensor 30*j* is placed at an anatomical location on the simulator 14 where specific heart, lung (including airway), Korotkoff, fetal, or other sounds are normally heard. The sensor 30*j* provides at least one signal which is identified by the stethoscope 12*j*, thereby directing an integrated sound circuit to play a sound to the user appropriate for the anatomical location of the sensor on the simulator 14. It is understood that the sound circuit has a stored library of body sounds corresponding to the location of the selected sensor 30*j*, and that the sensor 30*j* is illustrative of any number of similar sensors.

Figure 3B:
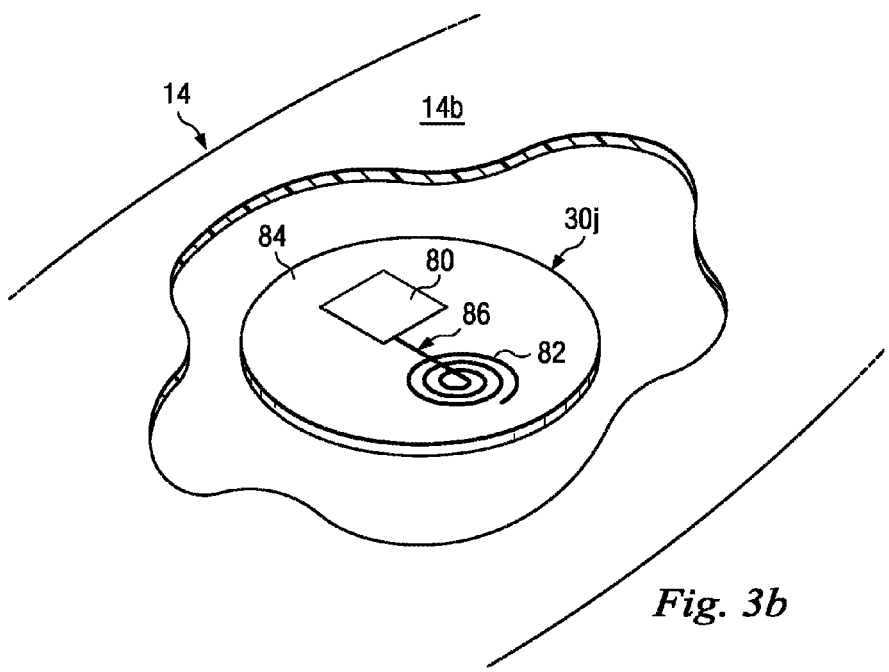
FIG. 3b is a perspective view with a cutaway of a sensor.
Figure 3A:
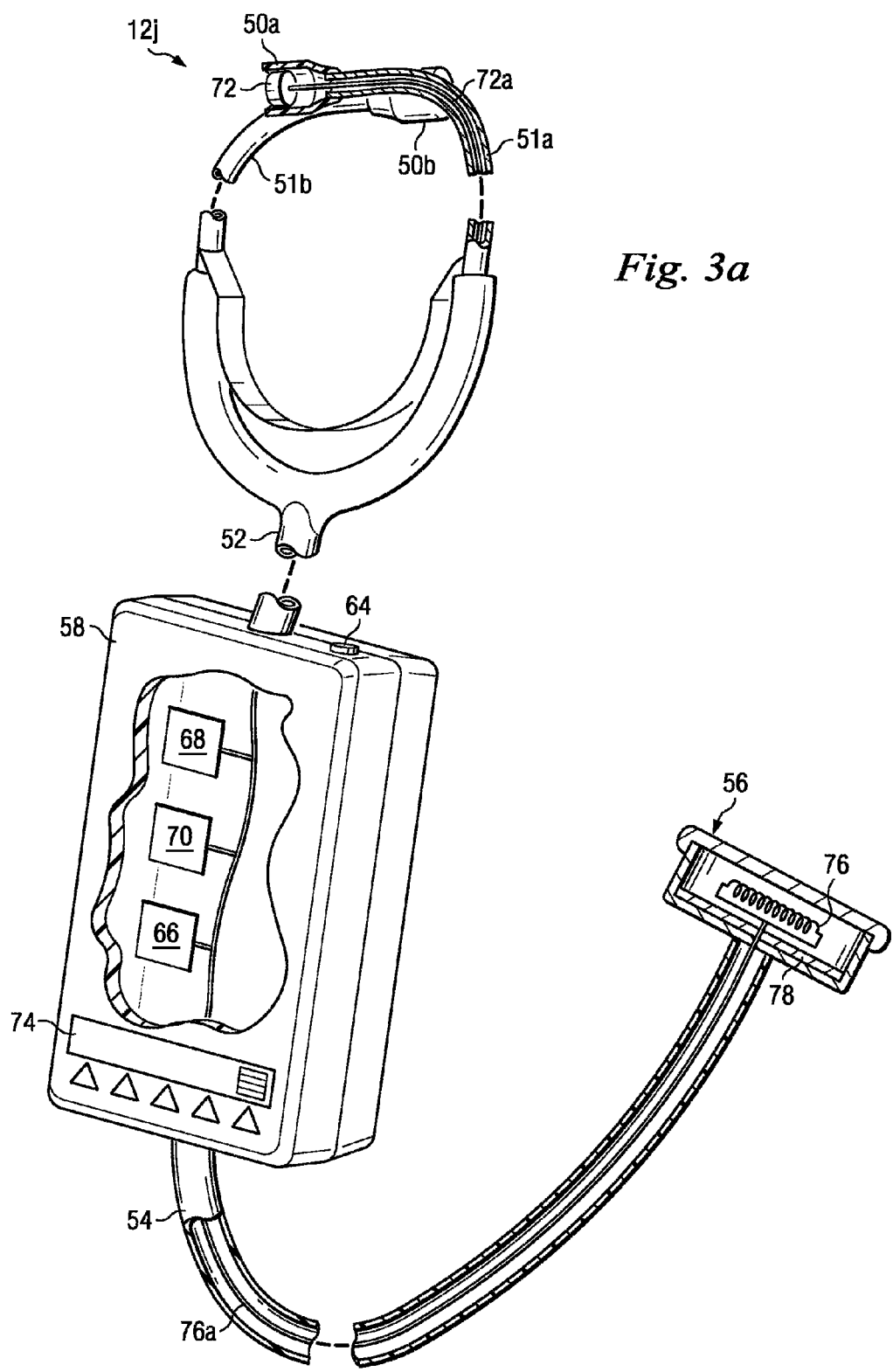
FIG. 3a is a perspective view with a cutaway of a virtual instrument.

Referring to FIG. 3*a*, in some respects, the appearance of the stethoscope 12*j* resembles a standard stethoscope, having earpieces 50*a-b* for hearing sounds, and being connected to extenders 51*a-b*, which are joined to a bifurcated ear tube 52. Similarly, the stethoscope further comprises a bell tube 54, and a bell 56, preferably made of nonferrous material. However, unlike conventional stethoscopes, an electronic control box 58 is disposed between the ear tube 52 and the bell tube 54. The control box 58 is understood to be an appropriately developed CIM 16, physically integrated into the virtual instrument 12*j*, thus simplifying the system 10. A jack 64 is provided on the control box 58 for output to an external speaker (not depicted), so that other users may hear the sounds heard in the earpieces 50*a-b*. This not only increases the number of users who benefit from the patient care activity, but allows an instructor to test the user's ability, and correct the user's technique if required. The control box 58 retains a small power source 66, such as a battery, an acquisition circuit 68 and a sound circuit 70 (see copending U.S. application Ser. No. 09/640,700, filed Aug. 17, 2000, for circuit diagrams) for directing a small speaker 72, such as is available from ADDAX Sound Company (Northbrook, Ill.), to play a predetermined sound. The speaker 72 is disposed in the earpiece 50a, and connected to the control box 58 via a wire 72a, allowing the user to hear the sounds produced by the sound circuit 70. It is understood that a second, substantially identical speaker may be disposed in the opposite earpiece 50b, and also connected to the control box 58. In an alternative embodiment, the speaker 72 may be disposed in the control box 58, and sounds transmitted via conventional ear tubes to the ear pieces. The sound circuit 70 is also connected to the jack 64 for allowing connection to an external speaker for the above-described reasons.

A switch 74, having a number of positions, is disposed on the control box 58 for switching between groups of sounds, for example exemplary normal and abnormal sounds that may be those heard in an adult, neonate, or fetus. An RF (radio frequency) signal acquisition coil 76, such as is available from M.C. Davis Co. (Arizona City, Ariz.), is disposed in the interior of the bell 56 for transmitting and acquiring RF signals, as will be explained. The acquisition coil 76 is a copper coil and circuitry having an associated wire 76a, which is attached to the electronic control box 58. A polymeric disc 78 is disposed between the acquisition coil 76 and the bell 56 to decrease noise from the bell.

In other embodiments, the sounds are recreated by speakers (not shown) disposed within the manikin such that the sounds are audible without the use of a real or virtual stethoscope. In yet other embodiments, the sounds are recreated by speakers (not shown) disposed within the manikin such that the sounds are audible with the use of a real stethoscope.

Referring to FIG. 3b, the sensor 30j is disposed beneath the skin 14b of the simulator 14 to avoid visual detection by the user. Likewise, it is advantageous that the sensor 30j have a minimal thickness to prevent intentional or accidental detection, as some anatomical locations, for example, intercostal spaces, must be palpated in order to be located. In an alternative embodiment, the sensors 30j may be affixed to an overlay (not depicted) substantially similar to the skin 14b, thus allowing the overlay to be placed over other simulators and models of patients, thereby converting those devices to allow them to be used with the stethoscope 12j.

The sensor 30j comprises an RF ID tag 80, such as is available from Microchip Technology, Inc. (Chandler, Ariz.) (Part No. MCRF200-I/3C00A), which may be programmed using "Developer's Tools" also sold by Microchip Technology, Inc. to engender a unique signal that serves to identify the particular sensor 30j. A coil 82, such as is available from M. C. Davis Co. (Arizona City, Ariz.), is operably connected to the tag 80. The tag 80 and coil 82 are potted in RTV potting material 84, or silicon rubber, such as is available from M. C. Davis Co. (Arizona City, Ariz.), to prevent damage. Once potted, the tag 80 and coil 82 collectively form a COB module 86 which emits a signal comprising a unique train of frequencies when interrogated.

In operation, the COB module 86 may actively broadcast the frequencies, but preferably the COB module is passive, that is, only activated when interrogated by the acquisition coil 76 in the stethoscope bell 56. In this preferred embodiment, the acquisition coil 76 delivers a carrier signal, such as a 125 kHz excitation frequency, which is received by the COB module 86 when the bell 56 is brought within a predetermined proximity, or acquisition distance, of the COB module. The acquisition distance of the bell 56, and therefore the acquisition coil 76, to the COB module 86 is determined by the strength to noise (S/N) ratio of the carrier signal. Thus, adjustment of the S/N ratio of the carrier signal provides a means for controlling the precision with which the user must place the stethoscope bell 56 in relation to the anatomical location of the sensor 30j, and therefore the COB module 86. Precise placement of the bell 56 on the simulator 14 by the user is rewarded with feedback, in the form of an appropriate body sound. Normally, the S/N ratio is set to require that the bell 56 be brought within approximately one-half to two centimeters of the COB module 86 of the sensor 30j.

In response to receiving a sufficiently strong carrier signal, the COB module 86 emits a train of two identifying frequencies for use in a process conventionally known as frequency shift keying (FSK), although other keying methods could be used. The acquisition coil 76 in the stethoscope bell 56 receives the emitted frequencies and relays the signal to the acquisition circuit 68, which determines the identity of the sensor 30j. As the anatomical position of each sensor 30j is known to the programmer, a selection of appropriate body sounds associated with each sensor is provided, and accessible to the sound circuit 70. Thus, by identifying the sensor 30j, the acquisition circuit 68 directs the sound circuit 70 to play an appropriate body sound for the anatomical position of the COB module 86, which is heard by the user through the speaker 72 disposed in the earpiece 50a. It can be appreciated that to expose the user to a greater selection of sounds, more sensors 30j could be added to the simulator 14, or each sensor could correspond to more than one sound. As depicted, the switch 74 has five different positions, and includes means for switching the sound circuit 70 between five different groups of sounds. Thus, it is understood that the number of switch positions corresponds to the number of sounds that can be produced by a single sensor, i.e., with thirteen sensors and five switch positions, the user could listen to up to sixty-five location-appropriate sounds, including examples of normal and abnormal sounds.

It can be appreciated that the above-described acquisition coil and COB module may be adapted to be used with the respective leads, paddles, or probes ("connectors") of the ECG monitor 12c, the temporary external pacer 12f, the automatic external defibrillator (AED) 12g, the manual defibrillator 12h, the ultrasound wand 12i, and the fetal distress monitor 12l. If desired, the connectors may be equipped with adhesive to temporarily hold them in place on the patient simulator. The interaction between the instruments' connectors and the sensors 30, as sensed by the CIM 16, confirms proper placement. The hidden location of the sensors 30 beneath the skin of the patient simulator further challenges a user's patient care skills, as well as more closely mimicking a real patient.

It is understood that the simulator 14 is designed to represent a patient and receive treatment, and as such the simulator 14 could take a variety of forms, including a fully articulating and adult-sized obstetrics simulator, a curled fetus, an articulating fetus, multiple fetuses, or a neonate, as well as a portion of simulated patient, for example, the torso and pelvic region.

Figure 4:
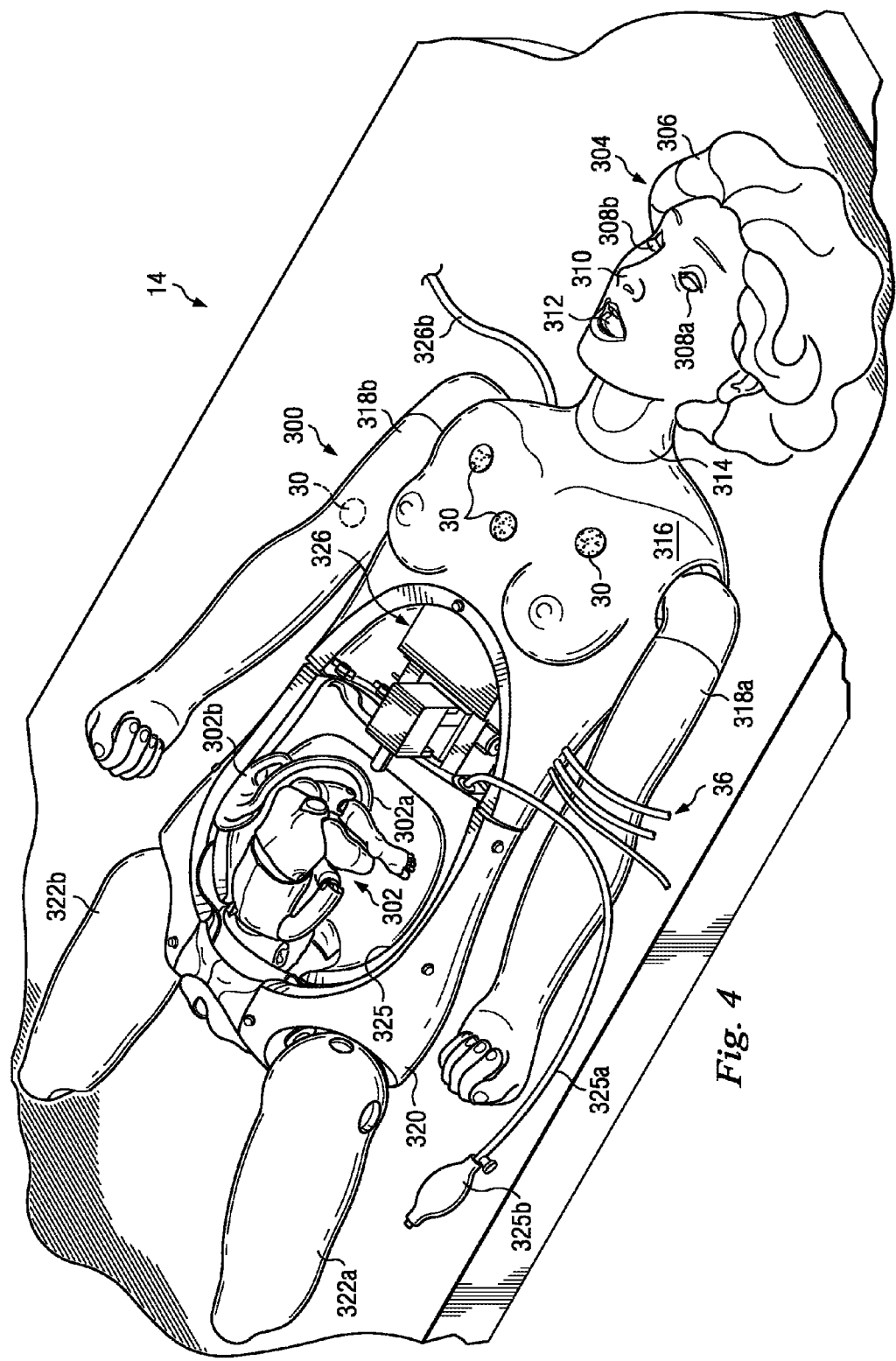
FIG. 4 is a perspective view of an illustrative embodiment of a patient simulator.
Figure 5A:
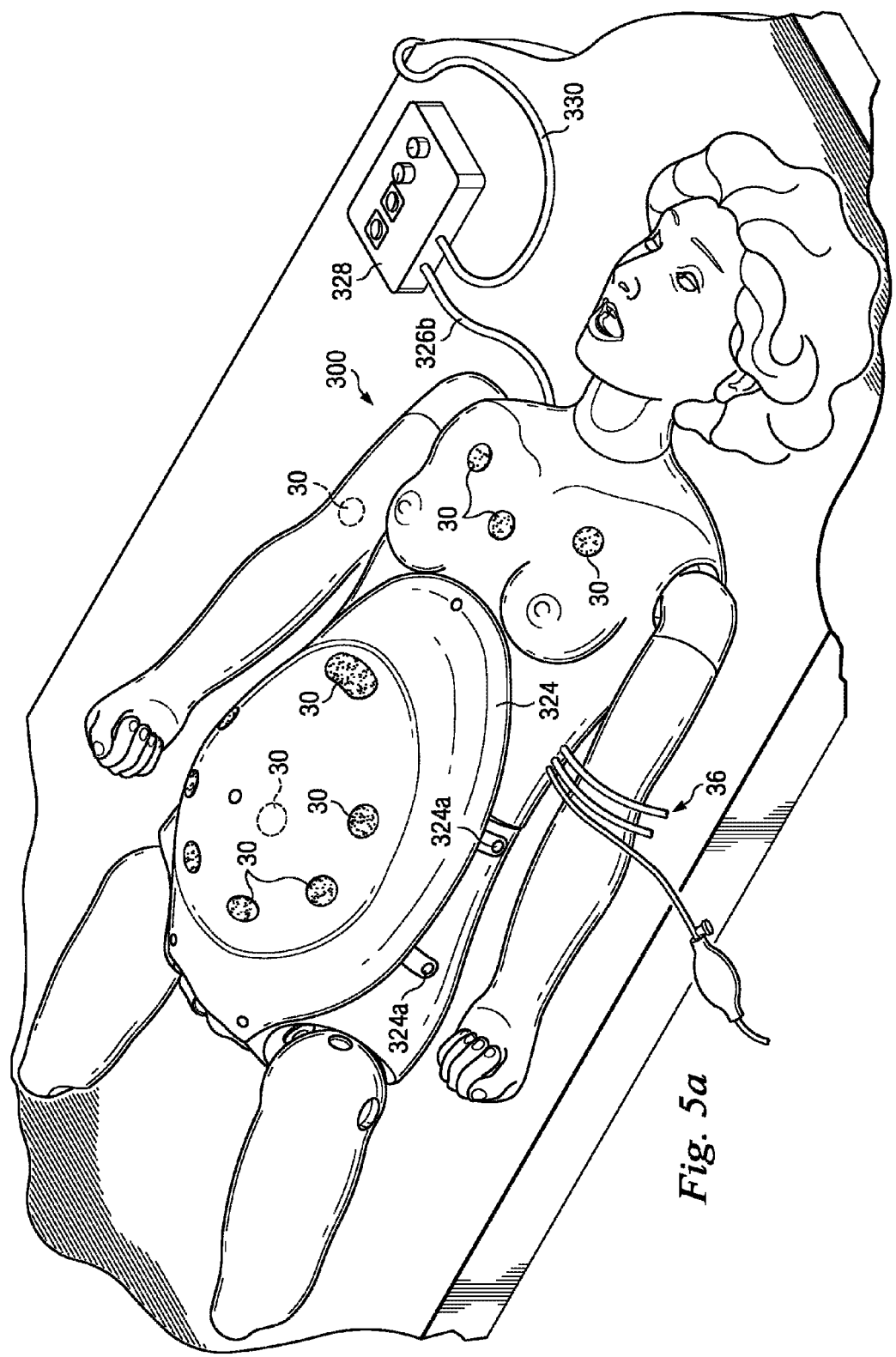
FIG. 5a is a perspective view of the patient simulator of FIG. 4 with an attached cover.

Referring to FIGS. 4 and 5a, in an illustrative embodiment, the simulator 14 comprises a child birthing maternal simulator 300 and a removable associated fetal simulator 302. The maternal simulator 300 has a head 304, with hair 306, eyes 308a-b, a nose 310, and a mouth 312. The head assembly contains a realistic airway (not depicted) capable of accepting conventional airway adjuncts. Sensors, generally denoted 30 (FIG. 1a), may be disposed on the skin of the maternal simulator (shown as stippled) and/or beneath the skin (shown in phantom). It is understood that in one embodiment of the maternal simulator (not depicted), no sensors are associated with the simulator. Lines 36 protrude from the torso 316 for providing electrical, pneumatic, or fluid connections, as well as for connecting the sensors 30 to the CIM 16, if necessary.

In other embodiments, the maternal simulator 300 is tetherless. That is, the maternal simulator is functional without wired or tubular connection to other devices outside of the simulator and, therefore, does not have lines 36, 325a, and 326b extending from the torso 316. Rather, the maternal simulator is self-contained. Thus, the maternal simulator 300 can include an internal power supply, such as a rechargeable power cell, and all pneumatic and fluid connections are made to the corresponding compressors or other devices within the maternal simulator 300. As the maternal simulator is self-contained, it is not only portable, but can be in use while being transported between different locations. Further, in such embodiments, the maternal simulator 300 may communicate with other devices, such as the CIM 16, through wireless communication. Thus, the entire simulator system 14 can be functional up to the limits of the wireless communication. Further, in some embodiments the maternal simulator 300 may connect to a computer or network system wireless, which then connects to the CIM 16 via a wired or wireless network, making the functional distance of the maternal simulator virtually limitless. Though only the maternal simulator has been described here as being self contained, the fetal and neonatal simulators described in more detail below are also tetherless in some embodiments. In some embodiments, the simulators are configured to be used both un-tethered and tethered. In some embodiments, the simulators are fully-functional when used un-tethered (i.e., the simulator has the same functionality tethered and un-tethered.)

A pair of arms 318a-b are connected to the torso 316. At least one arm contains an IV receptacle (not depicted) capable of accepting medications, and sensors 30a may be placed within the receptacle to ascertain whether an IV has been started. Similarly, the arm may contain a sensor 30d for auscultation of Korotkoff sounds, as well as means for measurement of blood pressure. A pelvic region 320 of the torso 316 receives a pair of legs 322a-b.

Referring to FIG. 5a, a cover 324 may be attached to the torso 316 via a plurality of snaps 324a, although other reversible fastening means, such as hook and loop closures may be used. The cover 324 retains sensors 30, for cooperating with the ultrasound wand 12i, fetal distress monitor 12l, and the stethoscope 12j, or alternatively at least one small speaker, to allow simulation of fetal heart sounds which may be detected by the stethoscope 12j or a conventional stethoscope, respectively. In one embodiment, the cover 324 surrounds an open cell foam (not depicted) connected to means for producing a vacuum. Activation of the vacuum shrinks the foam, making it feel harder, which simulates uterine contractions by the maternal simulator 300. Alternatively, the cover 324 may retain an air bladder and associated line (not depicted) for pressurizing the cover, thus making it feel harder. In yet other embodiments, the cover may contain a plurality of flexible tubes (not shown) extending across the torso. The air pressure in the tubes determines the hardness. The pressure is adjusted to change the hardness. It is understood that different levels of hardness may be produced to simulate different levels of contraction strength, for example, mild, moderate, and strong contractions. If connected to the CIM 16 and program 15a, the contractions could be spaced at regular intervals, and associated data for maternal intrauterine pressure may be displayed by the program, as will be discussed with FIG. 14.

Returning to FIG. 4, the fetal simulator 302, has an umbilical cord 302a and placenta 302b, and is depicted as resting upon a removable stage 325 disposed inside the maternal simulator. The removable stage 325 has a bladder (not shown), a line 325a, and a bulb 325b. When the bulb 325b is used to pump air into the bladder, the stage 325, and hence the fetal simulator 302, is raised relatively upwards. When covered with the cover 324 (FIG. 5a), raising of the stage 325 allows a user to palpate the fetal simulator 302 through the cover to assess position, as well as to perform Leopold maneuvers. In other embodiments, the bulb 325b is replaced by an alternative pump, such as an electrically powered, pneumatic pump. The electric pump may be controlled remotely through a computer system or other device.

A birthing device 326 is disposed inside the torso 316, as will be described. The cover 324 is designed to obscure the fetal simulator 302 of the simulator and the birthing device 326 from view, thus more accurately simulating the child birthing process, and challenging the user's diagnostic abilities. With the stage 325 removed, the birthing device 326 may be operated via a manual crank (not shown), or by a small motor 326a connected via a line 326b to controlling means for turning the motor on or off, as well as determining operational speed.

Figure 5B:
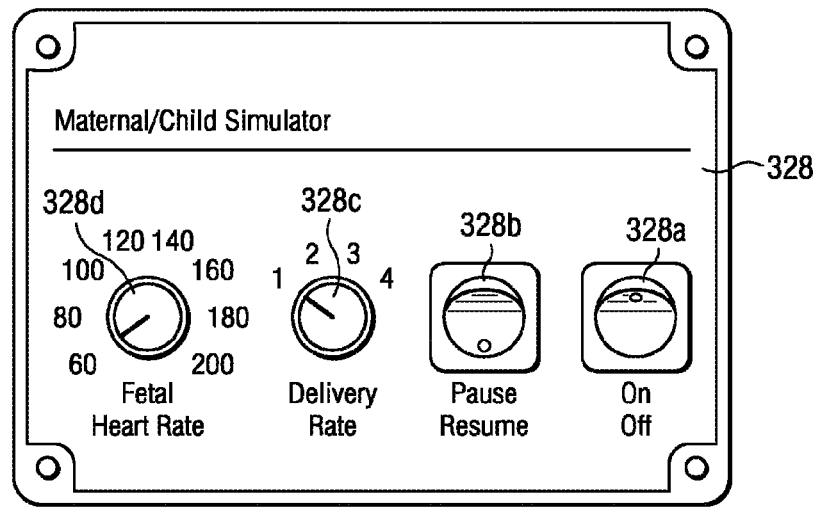
FIG. 5b is a top plan view of a control box.

In a first embodiment, software of the program 15a controls the birthing device 326, as will be discussed in conjunction with FIG. 14, below. In an alternative embodiment, the controlling means is a control box 328, and a line 330 which connects the control box 328 to the CIM 16. Referring to FIG. 5b, the control box 328 has controls 328a-d for respectively turning the simulator 14 on and off, pausing and resuming child birthing, determining the speed of the delivery rate, and setting the fetal heart rate.

Figure 6:
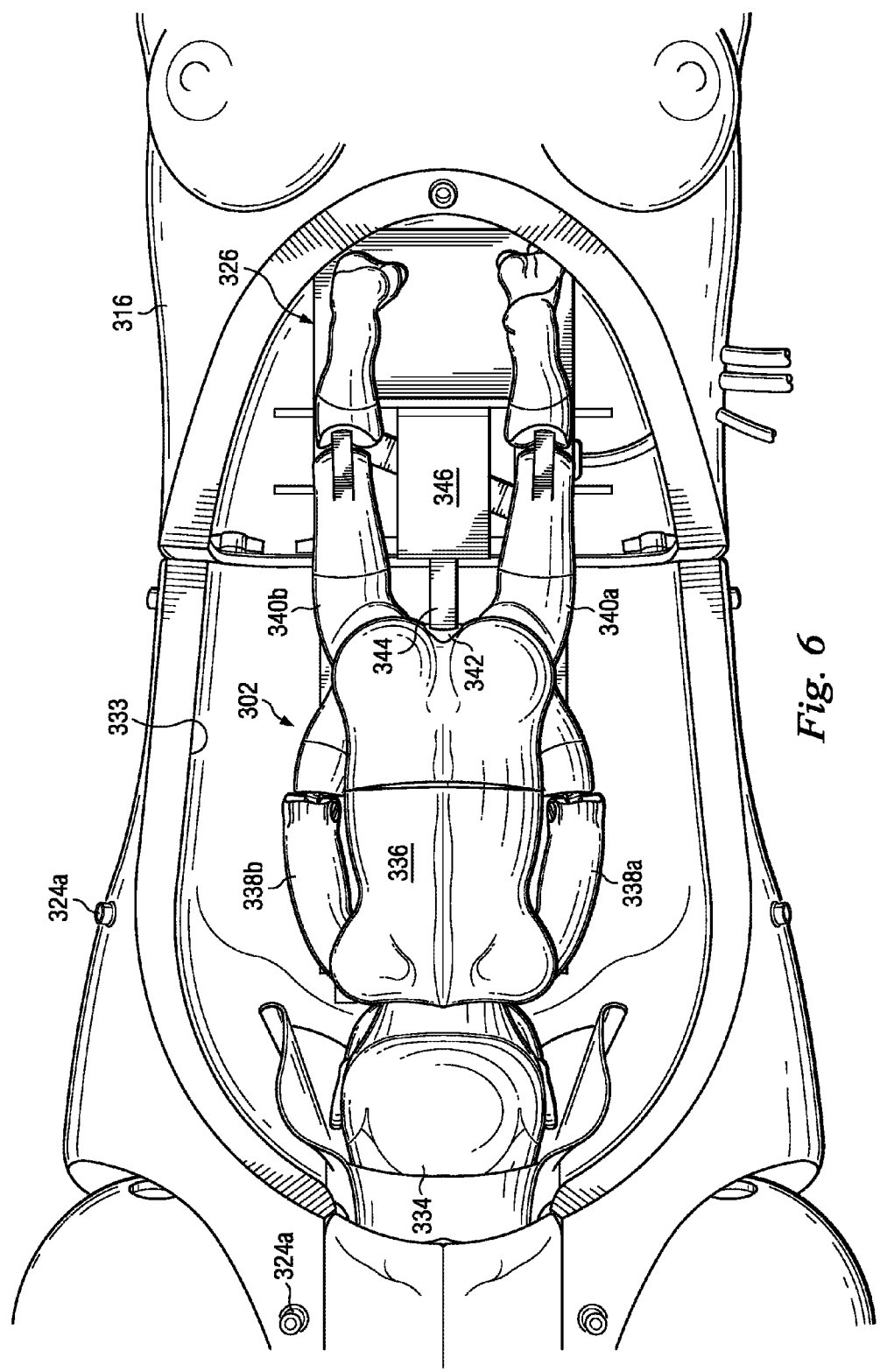
FIG. 6 is a perspective view of the torso of the patient simulator of FIG. 4.
Figure 7:
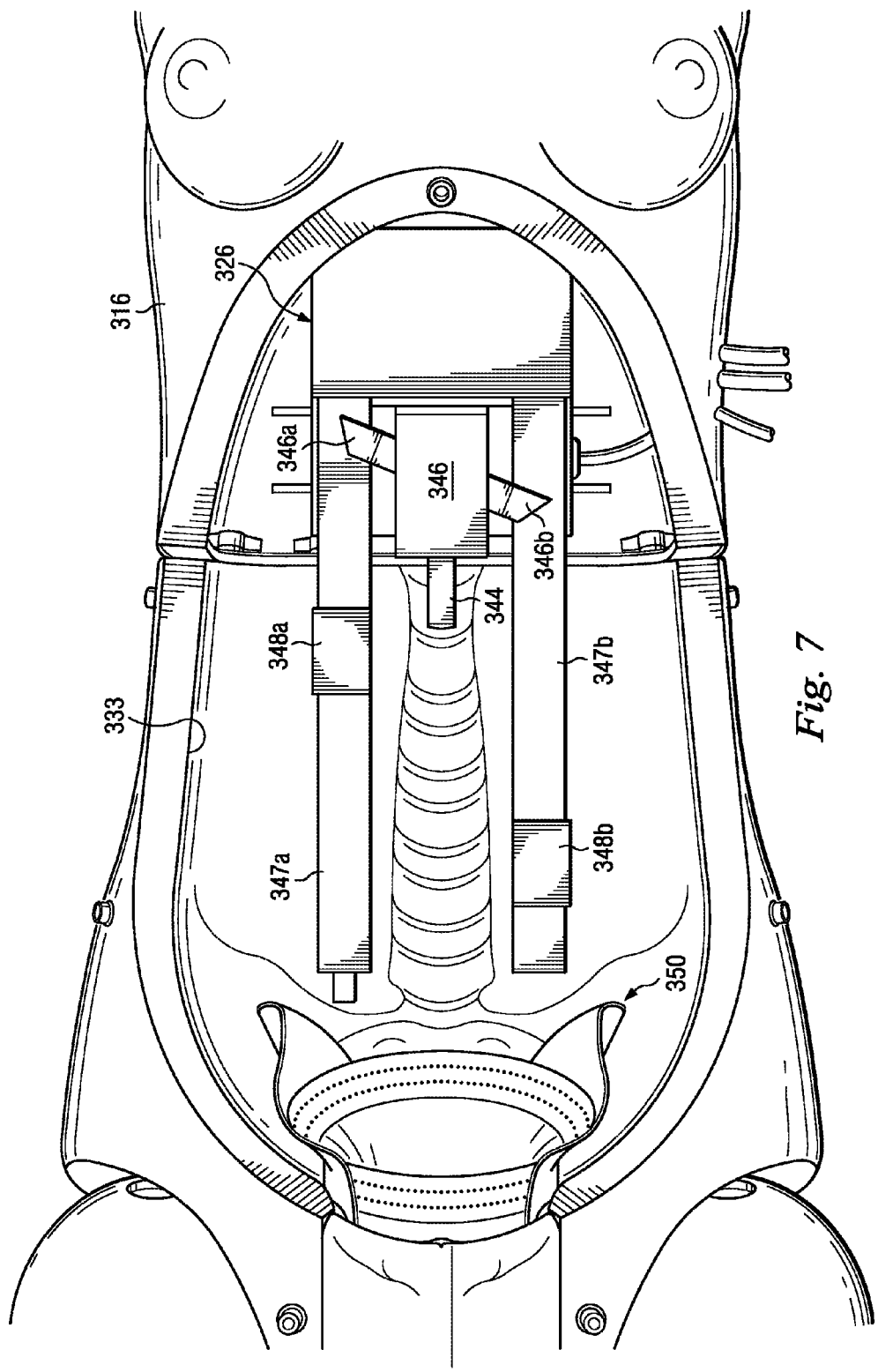
FIG. 7 is a perspective view of FIG. 6 with the fetal portion of the patient simulator removed.

Referring to FIGS. 6 and 7, the torso 316 of the maternal simulator 300 is shown with the cover 324 removed to expose the fetal simulator 302. The fetal simulator 302 is disposed in a cavity 333 of the maternal simulator 300, and has a head 334, an attached torso 336, with a pair of arms 338a-b and legs 340a-b attached to the torso. The head 334 is soft to allow for vacuum extraction, and has a mouth and nose which may be suctioned by the user.

In that regard, in some embodiments the fetal simulator 302 includes force sensors (not shown) positioned in the neck, shoulders, and hips to monitor the amount of force being applied on the fetal simulator during delivery. Pulling on the head 334 produces a signal from the neck sensor. The amount of force is relayed to the user and/or instructor by a user interface. The user interface can include a graphical display or audible signals. For example, the user interface may produce a bar graph indicating the amount of force being applied or the user interface may beep or otherwise sound an alarm when the force exceeds a predetermined threshold, prompting the user to reduce the force being applied or try a different delivery method. In one embodiment, the maximum force threshold is approximately 40 lbs. of force. In one embodiment, the preferred range of force is between approximately 17-20 lbs. of force. Shoulder dystocia is a potentially fatal situation wherein the shoulder of the fetus becomes lodged behind the maternal pubic bone. Too much force can lead to brachial plexis and even Erb's palsy in the fetus. To simulate this potential situation, shoulder sensors are included at the left and right shoulders of the fetal simulator 302 to monitor the force being applied at the shoulders. Finally, various situations, such as vaginal breeches, can cause the legs 340*a-b* to be grasped and removed from the vagina. The hip sensors serve to monitor the force being applied to the fetal simulator 302 in such situations. In some embodiments, the sensors 30 are in communication with an output device operable to provide output signal indicative of the measurement a particular sensor is adapted to monitor. The output device may output an electrical signal, wireless signal, or any other suitable output signal.

The umbilical cord and placenta 302*a-b* (FIG. 4) are removed to simplify the illustration, but it is understood that the placenta 302*b* (FIG. 4) could be disposed in any number of common orientations, such as normal fundal, low placement, or placenta previa, and attached to the cavity 333 with conventional removable fasteners. Likewise, the umbilical cord 302*a* (FIG. 4) could be presented to replicate various complications, and may house connecting lines to the fetal simulator 302 to allow an umbilical pulse to be felt by the user, or to convey electricity to the fetal simulator 302, if necessary.

A receiver 342 is disposed on the fetal simulator 302 to allow the birthing device 326 to retain the fetal simulator. Other receivers, similar to the receiver 342, are contemplated on different portions of the fetal simulator 302, such as to simulate a breech birth, and as the fetal simulator 302 articulates, a variety of breech deliveries, such as full, frank, and footling may be simulated.

The birthing device 326 has a projection 344 of a ram 346 which cooperates with the receiver 342 of the fetal simulator 302 to retain the fetal simulator. In some embodiments, the receiver 342 and projection 344 are adapted for selective engagement such that the fetal simulator 302 is selectively engaged with or released by the maternal simulator 300. In the depicted embodiment, the ram 346 is driven by a drive system, including a small electric motor, gears, electronic logic to permit resetting, means to determine the position of the ram, and a forward and reverse function. The ram 346 proceeds down a set of tracks 347*a-b*, thereby translating the fetal simulator 302 out of the maternal simulator 300.

The projection 344 of the ram 346 is rotatable, the birthing device 326 thereby producing both rotational and translational movement of fetal simulator 302, to simulate a realistic child birthing scenario, wherein the fetus makes a turn to bring it to a normal nose down position of crowning, and it makes another turn after crowning to allow its shoulders to better pass through the birth canal. In some embodiments, the receiver 342 is disposed in another portion of the fetal simulator, such as the head, neck, shoulders, arms, hips, and/or legs. Alternative embodiments of the receiver 342 and projection 344 are discussed in relation to FIGS. 24-27 below.

In one embodiment, levers 346*a-b* of the ram 346, being operably connected to the projection 344, engage cams 348*a-b*, respectively, to produce rotation. As the ram 346 proceeds down the tracks 347*a-b*, the levers 346*a-b* of the ram engage the fixed cams 348*a-b* in turn, causing the respective lever to move. Movement of the lever rotates the projection 344. Eventually, the respective lever is moved to a point where the lever clears the respective cam. It can be appreciated that the cams 348*a-b* may be located at places along the tracks 347*a-b* where rotation is desired, the tracks simulating the birth canal. Thus, internal rotation of the fetus is produced by the lever 346*a* engaging the cam 348*a*, and external rotation of the fetus is produced by the lever 346*b* engaging the cam 348*b*. As described below in relation to FIG. 28, in some embodiments the cams 348*a-b* are moveable between a position for causing rotation of the fetal simulator and a position that does not cause rotation of the fetal simulator. Further, in some embodiments the cams 348*a-b* include intermediate position(s) to provide some rotation to the fetal simulator. Alternatively, the program 15*a* allows for adjustment of the rotation of the projection 344 from zero to one hundred and eighty degrees, as will be discussed with reference to FIG. 14, below. In either embodiment, the fetus 302 passes through a distensible cervix 350, as will be described.

Figure 9:
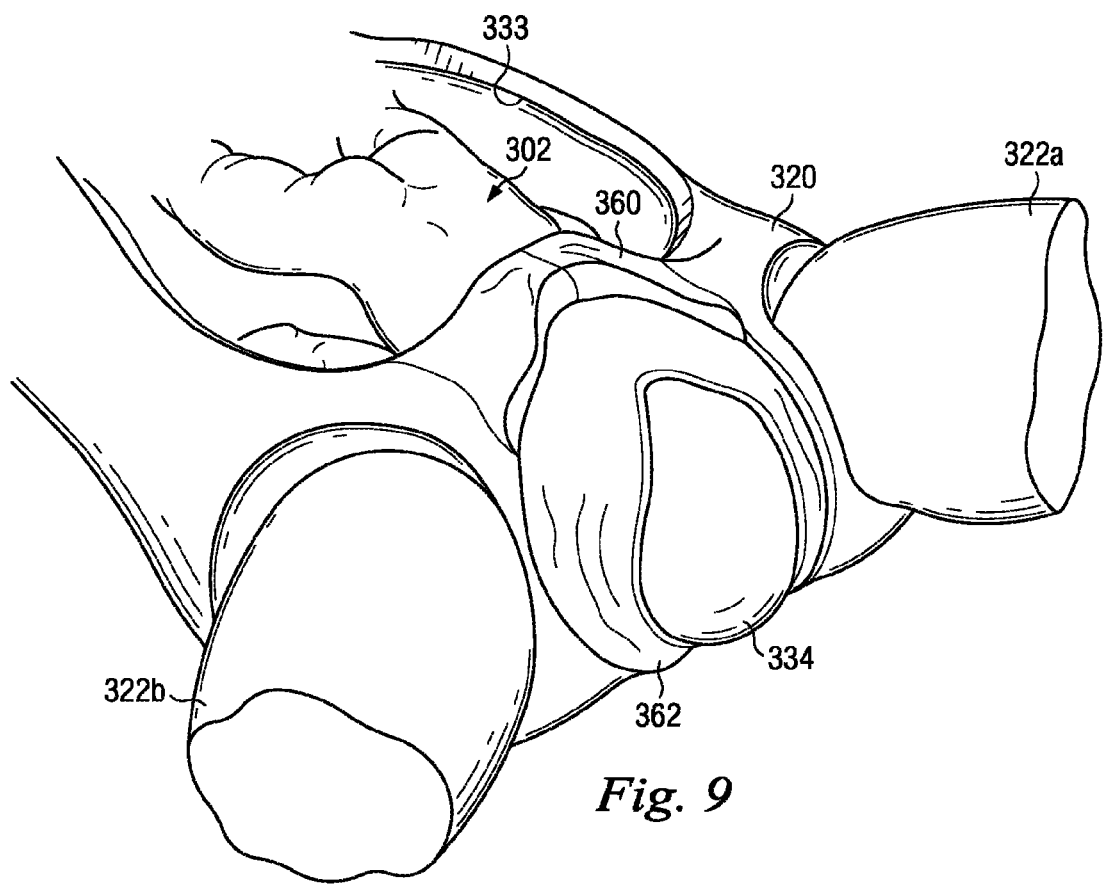
FIG. 9 is a perspective view of the exterior of the patient simulator.
Figure 8:
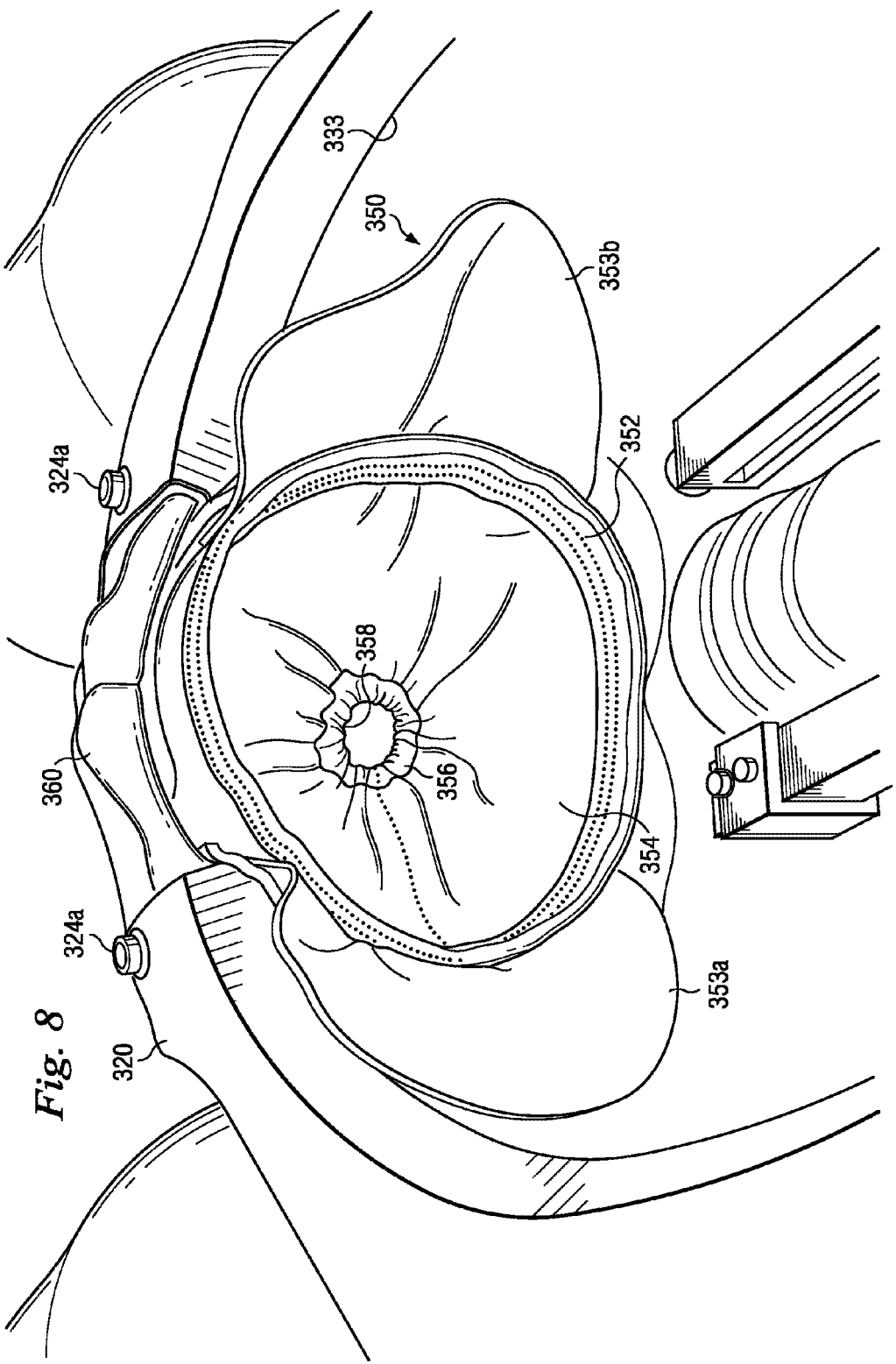
FIG. 8 is a perspective view of a distensible cervix of the patient simulator.

Referring now to FIGS. 8 and 9, the distensible cervix 350 comprises a ring 352 having attached flaps 353*a-b* for maintaining the cervix's position in the cavity 333. As such, the flaps 353*a-b* may have attached snaps, hook and loop closures, or other reversible fastening means. A wall 354 is connected to the ring 352, and is preferably of an elastic material, such as Lycra$^7$, or thermoplastic elastomer. A gathering 356 of the wall material defines a port 358. The gathering 356 may have an associated elastomeric element disposed interiorly to enhance the elasticity of the port 358. Alternatively, the wall 354 itself may provide sufficient elasticity.

The port 358 expands from about two to ten centimeters in diameter as the fetal simulator 302 is pushed through the port, and because of the shape of the fetal simulator's head 334, and the elasticity of the wall 354, dilation is automatically simulated coincident to fetal descent. The user may then practice measuring cervical dilation and plot labor progress as a Partograph. The elasticity of the wall 354 may be adjusted, for example by using thicker or thinner wall material, to produce a cervix having faster or slower dilation than normal, respectively. The cervix 350 is disposed concentric to the pelvic area 320, which has a pubic bone 360, as well as several cover snaps 324*a*.

The fetal simulator 302 moves through the cervix 350 and out of the cavity 333 past vulva 362. The vulva 362 are made of a flexible material so that the user may manipulate the vulva, or perform an episiotomy to birth the head 334. It is understood that the vulva 362 may comprise a portion of an insert (not depicted) including features such as a urinary tract and rectum, which could be replaceable with other genital inserts for displaying various patient conditions. After delivery, the user may practice postpartum exercises, such as massaging a uterus insert (not depicted) back to a desirable size, removing retained placenta parts (not depicted), or repairing the cervix 350 or vulva 362.

In one embodiment, the torso 316 contains a simulated heart, lungs, and ribs. The heart (not depicted) beats by the action of a pulsatile flow which is controlled by the program 15*a* in response to the condition of the patient and upon therapeutic interventions. Palpable pulses may be found at carotid, brachial, radial, femoral, and pedis dorsis locations. Specific pulse locations become non-palpable as the systolic pressure falls, and the absence or presence of a pulse will depend upon the simulated blood pressure. Heart sounds are heard at appropriate locations through the use of the stethoscope 12*j*. The heart beat is synchronized with the Virtual EKGs, which are determined by the program 15*a*. Application of the stethoscope 12*j* to a point below the BP cuff 30*d* (FIG. 2) will cause the appropriate Korotkoff sounds to be heard.

The maternal simulator 300 displays a combination of ventilation means, and lung and airway sounds are heard at appropriate locations using the stethoscope 12*j*. The simulator 300 breathes spontaneously in a manner that would achieve targeted arterial blood gases for a given situation, including response to interventions such as ventilation and administration of drugs, and demonstrates the amount of chest rise relating to the tidal volume and physiologic states. Normal gas exchange lung dynamics are virtual and are controlled by the program 15a, which may also determine tidal volumes (TV), functional residual capacity (FRC), and expired carbon dioxide ($CO_2$). Airway resistance, lung and chest wall compliance are also controlled by the program 15a.

The heart and lungs are connected to pressure transducers confirming airway ventilation and cardiac compression. For example, an air line may be mounted in tracheal wall or lungs of the simulator 300 and connected to a sensor circuit connected to the CIM 16 so that when cardiopulmonary resuscitation (CPR) ventilation is performed on the simulator, the CIM 16 monitors the timing and magnitude of the pressure and volume of the ventilation procedure, via the air line and the sensor. Similarly, a compression bladder may be embedded within the heart or chest cavity of the simulator 300 for sensing and confirming proper timing and magnitude of a CPR chest compression procedure, when connected by an air line to a compression sensor circuit attached to the CIM 16. It can be appreciated that compression and ventilation data is acquired from pressure waves sensed by the CIM 16 through the lines 36. The blood pressure, heart rate, and oxygen saturation is virtually measured by the BP cuff 30d (FIG. 2) and the Pulse Ox cuff 30e (FIG. 2), although the data displayed is generated by the program 15a.

Figure 10:
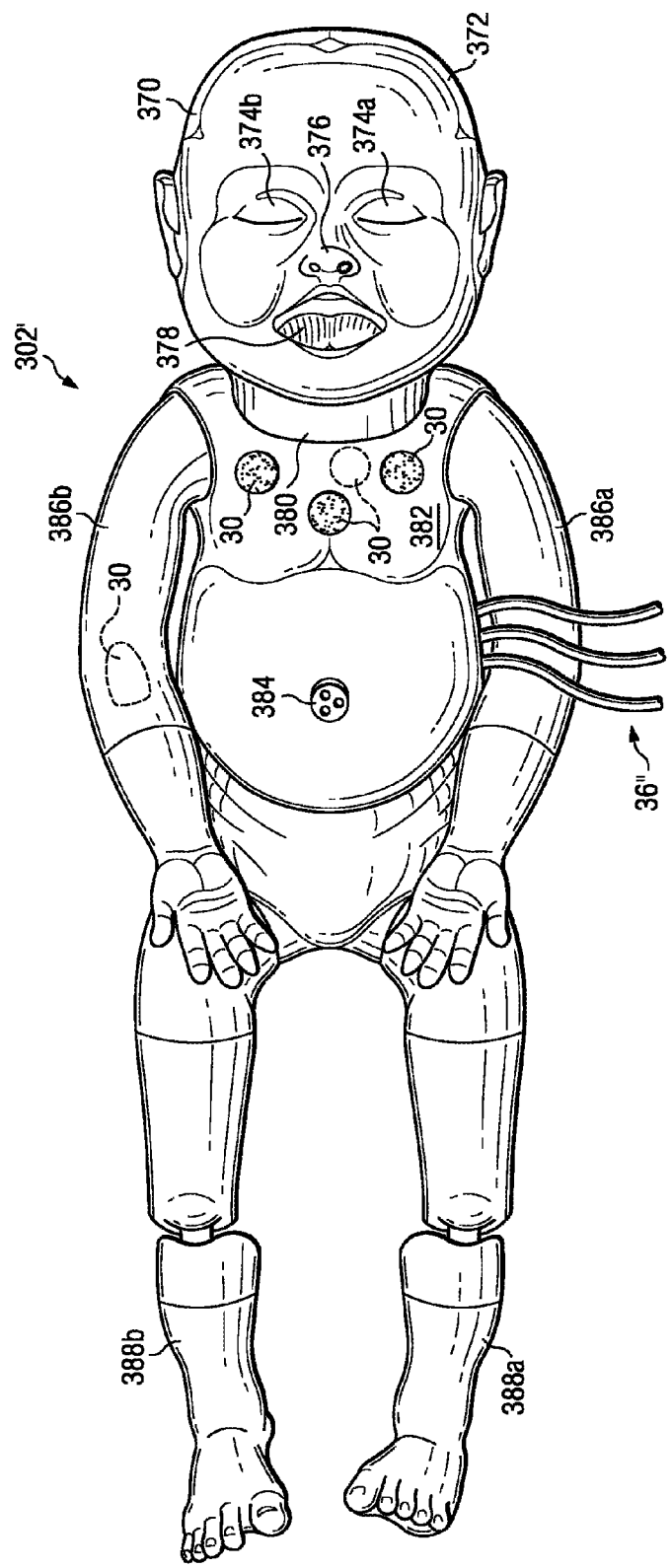
FIG. 10 is a perspective view of a neonatal embodiment of a patient simulator.

Referring to FIG. 10, a neonate simulator 302' may be used to replace the fetal simulator 302 (FIG. 8) to allow practice of neonatal resuscitation according to the program 15a. In other embodiments, the fetal simulator 302 is itself used in post-birth simulations. In that regard, the fetal simulator 302 can have all of the functionalities and features of the neonate simulator 302' as described herein. The neonate 302' has a head 370, with hair 372, eyes 374a-b, a nose 376, and a mouth 378. The head assembly contains a realistic airway (not depicted) capable of accepting conventional airway adjuncts and a sensor for determining whether an airway adjunct has been placed, or whether a fluid has passed. The head 370 is connected via a neck 380 to a torso 382.

Sensors, generally denoted 30 (FIG. 1a), may be disposed on the skin of the neonate simulator (shown as stippled) and/or beneath the skin (shown in phantom). Lines 36" protrude from the torso 382 for providing electrical, pneumatic, or fluid connection, as well as for connecting sensors (not depicted) to the CIM 16. The torso 382 has an umbilical site 384, which provides a site for catheterization, and a simulated heart, lungs, and ribs for performing CPR. The heart and lungs are connected to pressure transducers as described above for the maternal simulator 300 for confirming airway ventilation and cardiac compression. The neonate simulator 302' exhibits many of the same features as the maternal simulator 300 (FIG. 6), including heart rate, pulse, oxygenation, and a variety of body sounds which can be detected using the stethoscope 12j (FIG. 2) or a conventional stethoscope. A pair of arms 386a-b, and a pair of legs 388a-b, are also connected to the torso 3382.

In one embodiment, the hands and feet as well as the face and upper torso change color based upon proper oxygenation or an oxygen deficit. As oxygenation decreases, the extremities (peripheral cyanosis) change color first, followed by the face and upper torso (central cyanosis). Such change is reversible as oxygenation is improved.

In a preferred embodiment, coloration is achieved using blue thermochromatic dye (such as Reversatherm Blue Type F, available from Keystone, Chicago, Ill.), approximately 3 grams dissolved in 10 grams of clear vinyl paint thinner, and dispersed into 300 grams of clear vinyl paint. The mixture is applied to the hands, feet, chest, and face. At room temperature, the neonate is blue. Resistance heaters (such as available from Minco Products, Minneapolis, Minn.) are connected in parallel, and placed under the skin to provide 5-15 watts/$in^2$, or heat energy sufficient to raise the surface temperature of the skin to about 115°, causing the bluish color to disappear. Power for the heater is supplied through the CIM 16. The peripheral and central heaters may be separately controlled to allow peripheral cyanosis without central cyanosis. Heat sinks may also be disposed with the heaters to allow faster cooling, and hence, faster changes in coloration.

In one embodiment, the thermochromatic system is logically linked to the program 15a, for example, an instructor defines the condition of the neonate. Afterwards, coloration is responsive to CPR quality being performed by a user, improving, worsening, or remaining the same. The program 15a also provides for an override if coloration changes are not desired. Coloration may alternatively be simulated by having applied a conventional photochrome to the simulator, such that upon exposure to an associated adjustable UV light, the simulator appears to turn blue. As another alternative, the coloration may be simulated by using colored lights. For example, in one aspect blue LEDs can be used.

As mentioned above with respect to the maternal simulator, in some embodiments the neonatal simulator does not include lines 36". Rather the neonatal simulator is tetherless such that is has self-contained functionality without the need for wired, tubed, or other physical connection to external devices.

Figure 11:
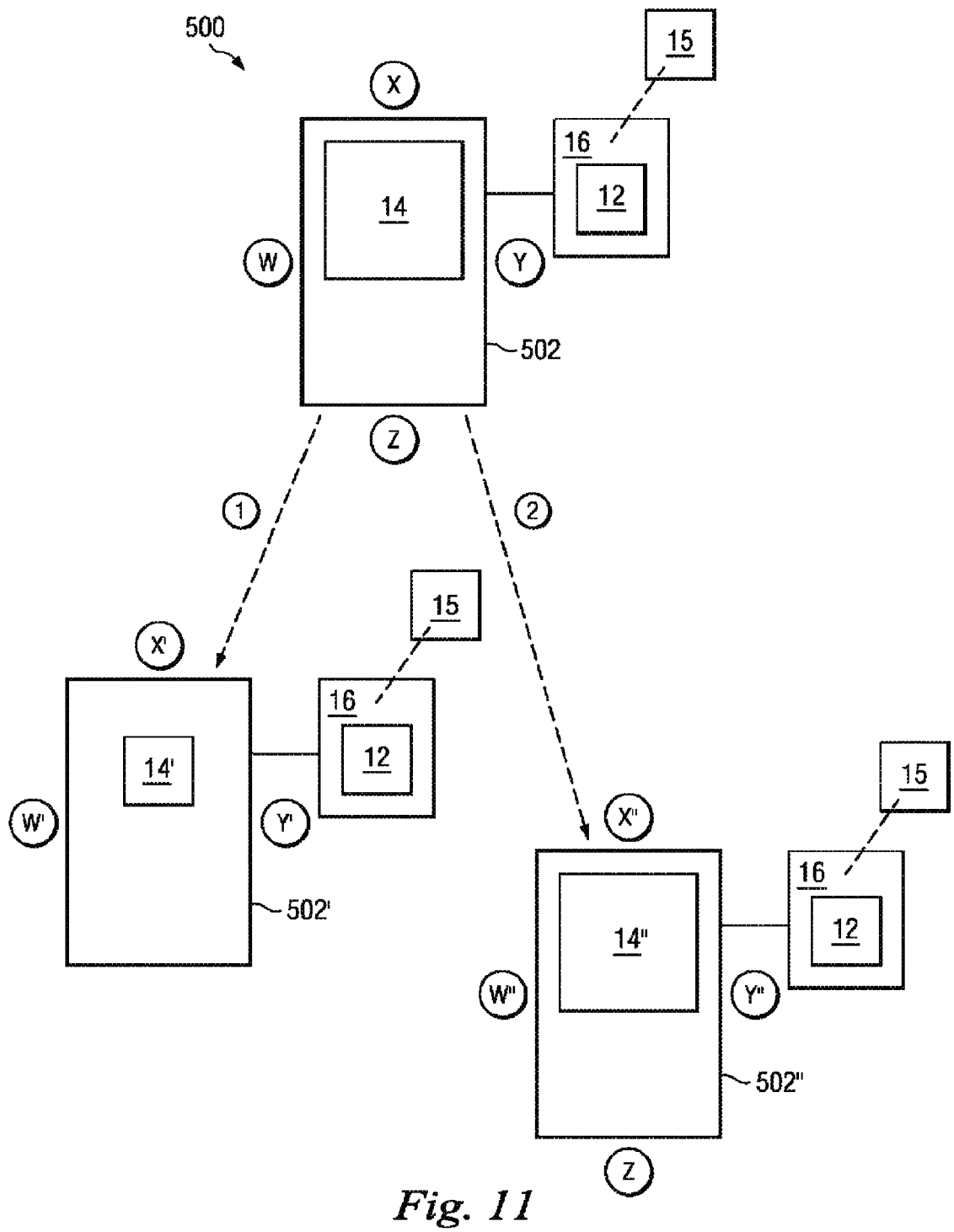
FIG. 11 is a schematic view of an illustrative use of the present system.

Referring now to FIG. 11, a child birthing system 500 illustrates the use of the foregoing embodiments. The simulator 14, for example, the maternal simulator 300 and fetus 302 are placed on a table 502. Students, W, X, Y, and Z, take places around the table, for example, W controls medication, Y controls virtual instruments 12, X controls anesthesia, and Z controls obstetrics. The child birthing device 326, as discussed above, may be driven via a manual crank or by a small motor 326a connected to either a control box 328, or the program 15a of the computer 15 may optionally (shown in phantom) control the birthing device 326. Whichever controlling means are used, the distensible cervix accurately reflects progress of the fetal simulator down the birth canal. Eventually, as described above, the fetal simulator is birthed.

Once the fetal simulator is birthed, a team W', X', and Y' (which are understood to be the same students W, X, and Y, or others depending on class size) moves along path 1 to practice neonatal care on a table 502'. At least one team, denoted by the absence of Z, must remain behind with the maternal simulator for monitoring and potential stabilization. The fetal simulator is switched with a neonatal simulator 14', for example, neonatal simulator 302' (FIG. 10). If connected to the computer, the program 15a may be used to simulate the need for neonatal resuscitation, and CPR and other emergency care protocols may be performed. The program 15a monitors the care received by the simulator via the CIM 16 and virtual instruments 12, and compares the care to accepted standards.

Meanwhile, the program 15a of the computer 15 may be used to simulate the need for maternal resuscitation. If so, a team moves along path 2 to practice maternal care on a table 502". Students, W", X", Y", and Z can work on the maternal simulator 14", for example maternal simulator 300 with the fetal simulator removed. CPR and other emergency care may be given, and the program 15a monitors the care received by the simulator via the CIM 16 and virtual instruments 12.

Figure 12:
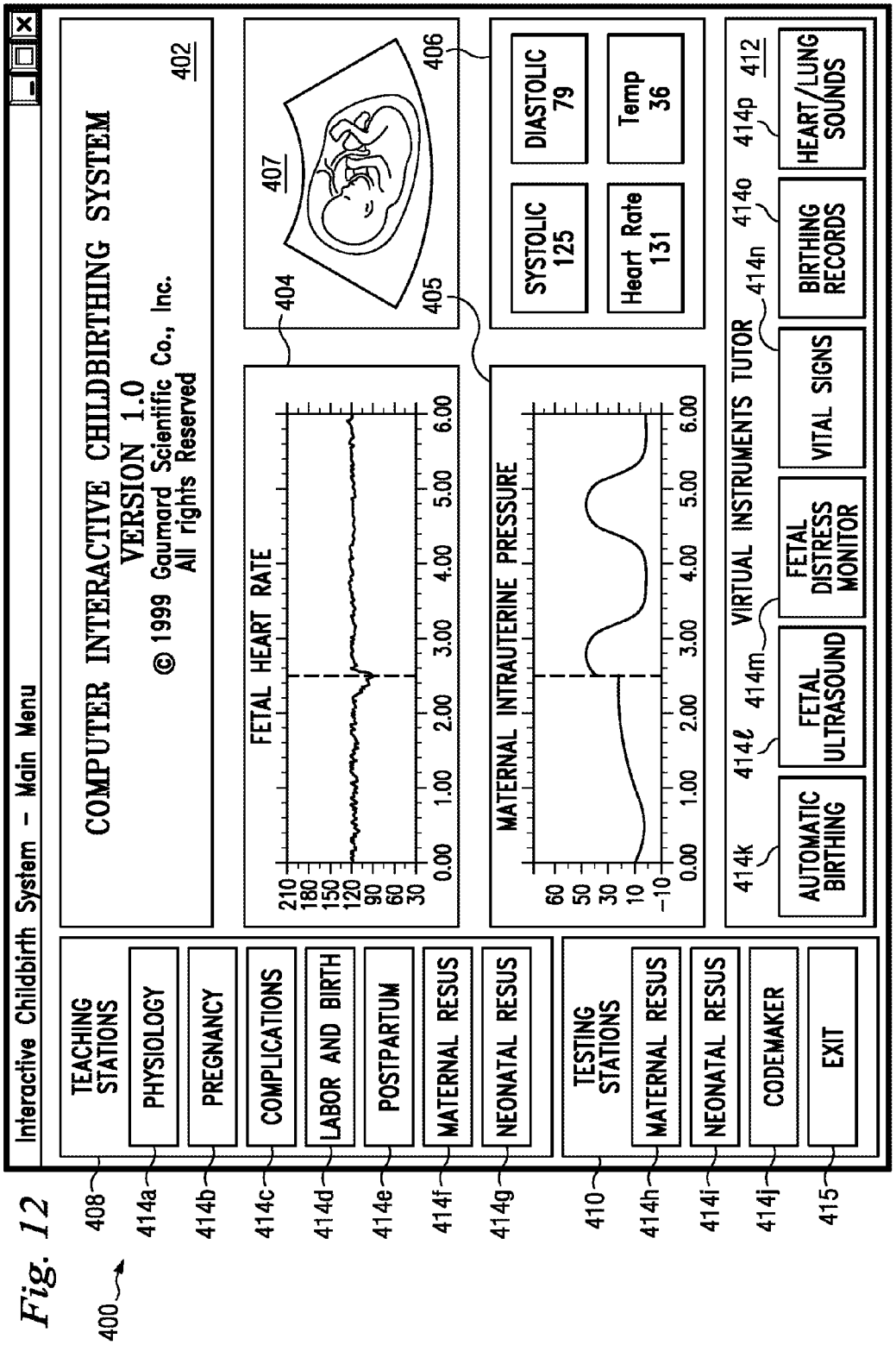

Referring now to FIG. 12, an introductory screen display 400 of the program 15a is presented on the computer 15 for teaching patient care protocols to a user. The display 400 includes several decorative features: a title box 402, a fetal heart rate box 404, a maternal intrauterine pressure box 405, a vital signs box 406, and an ultrasound video box 407. The display 400 also contains a teaching box 408, a testing box 410, and a virtual instruments box 412. As will be described, in some modules, the program 15a compares information pertaining to the user's activity with predetermined standards.

The screen 400 also displays a group of selectable patient care modules 414a-p provided by the program 15a, which furnish information on medical topics and associated concepts. Each module has a single topic, and represents an interactive patient care training session for the user. The modules 414a-g are disposed in the teaching box 408, and give an overview of relevant physiology, pregnancy, complications, labor and birth, postpartum, and maternal and neonatal resuscitation protocols. The modules 414h-j are disposed in the testing box 410, and give an opportunity to test a user in maternal and neonatal resuscitation protocols, as well as instructor defined protocols (Codemaker). An exit button 415 for exiting the program 15a is also disposed in the testing box 410. The modules 414k-p are disposed in the virtual instruments tutor box 412, and give a user a tutorial on use of the system, including automatic birthing, fetal ultrasound, fetal distress monitor, vital signs, Partographs, and heart and lung sounds.

Figure 13:
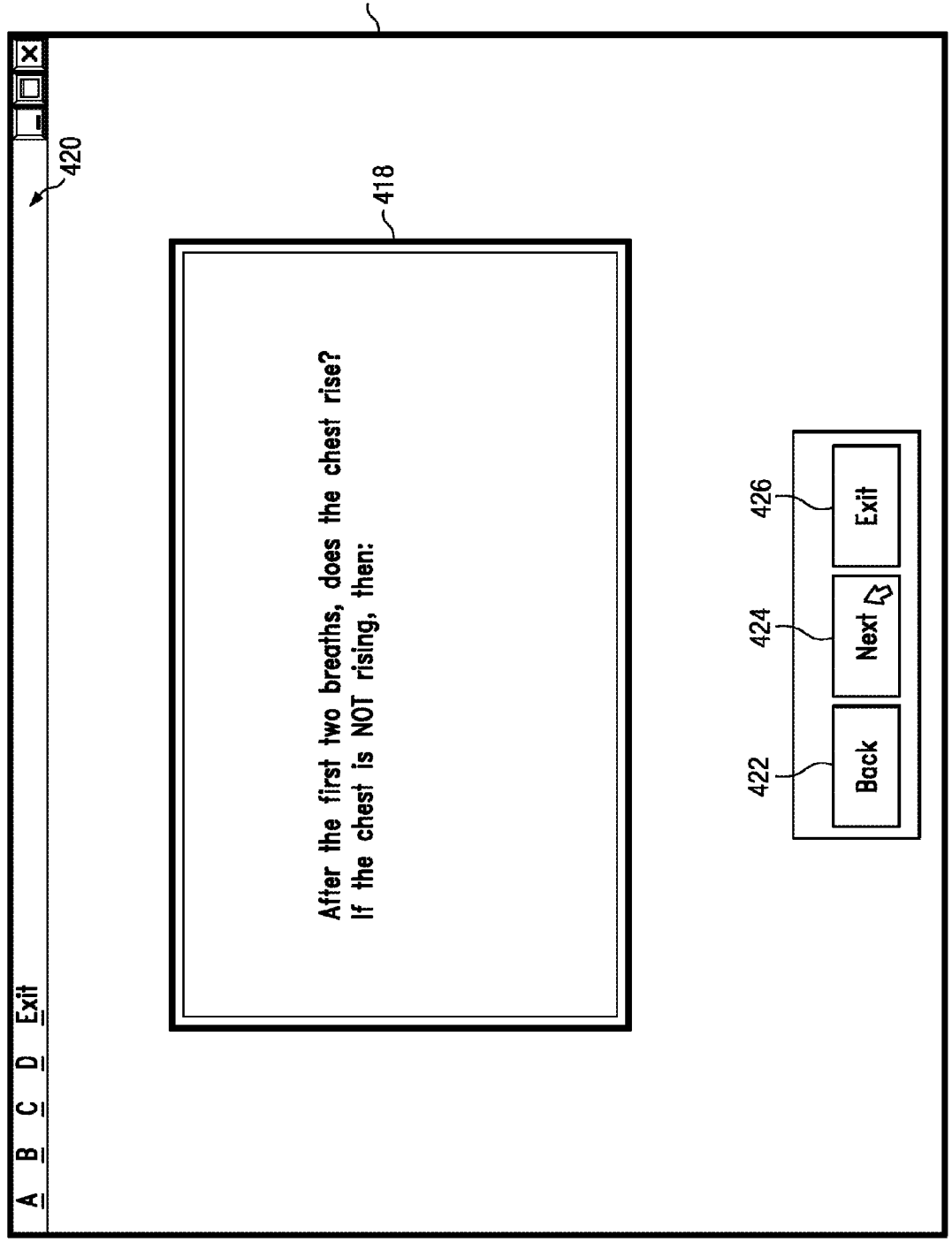

Referring to FIG. 13, if one of the modules (FIG. 12) is selected by the user, such as by voice recognition or selection with a mouse of the computer 15, the program 15a displays a display screen 416. The display screen 416 contains an information box 418, which contains topical information. The display screen 416 also has a menu bar 420 containing information items (illustrated as A-D for convenience) listing information categories specific to the topic of the selected module. It is understood that an item may be selected from the screen 416 via the menu bar 420, and that each module 414a-p has its own display screen with its own menu of specific informational items A-D, which may be expanded to include a large number of items, or condensed for example, by placing selectable sub-items under an item.

Selection of an item from a menu, other than an exit item, causes text and/or illustrations topical to the selected menu item to be displayed in the information box 418. In practice, the program may generate a new display screen (not depicted). As such, it is understood that the information screen 416 is used as an example of any number of screens, and furthermore, such screens can be displayed in sequential order, or a series, for each item. A series of screens, such as screen 416, comprises a tutorial regarding patient treatment protocols for the selected menu item. Thus, the user can review information from a library of topics by selecting the appropriate module, and item, and then navigating through a series. Navigation in a series of screens is attained by the user's selection between three boxes: 422, 424, and 426, respectively "Back", "Next", and "Exit", with corresponding function among the screens, such as proceeding backwards or forwards in the series. If no "Back" or "Next" function is possible, as respectively would be the case of the first and last screen of a series, the boxes 422 or 424 may be unselectable.

For example, modules 414f and 414g each engender a series to teach a user about maternal and neonatal resuscitation, respectively. The user may also practice CPR on the simulator 14 (FIG. 1a), such as the maternal simulator 300, or the neonatal simulator 302', above, and the program 15a senses the user's compression and ventilation, via the CIM 16 (FIG. 1a) and sensors 30 (FIG. 1a). The heart and lungs of the simulator 14 are connected to pressure transducers confirming airway ventilation and cardiac compression; for example, an air line may be mounted in tracheal wall of the simulator 14 and connected to a sensor 30 connected to the CIM 16, so that when CPR ventilation is performed on the simulator, the CIM 16 monitors the timing and magnitude of the pressure and volume of the ventilation activity, via the air line and the sensor. Similarly, a compression bladder may be embedded within the chest cavity of the simulator 14 for sensing and confirming proper timing and magnitude of a CPR chest compression procedure, when connected by an air line to a compression sensor 30 attached to the CIM 16. The program 15a compares the information pertaining to the user's activity with predetermined standards, and thus provides an interactive training session.

The predetermined standards are selectable, and reflect medical protocols used around the world, including BLS and ACLS guidelines set forth by the American Heart Association and others. At least seven major protocols for cardiopulmonary resuscitation (CPR) are stored and selectable by the user. Moreover, a user may update the protocols, or enter and store a "New Protocol" reflecting the local protocol regarding depth, duration, and frequency of cardiac compressions and airway ventilations. The program will use this series of acceptable limits to generate a new CPR waveform for testing CPR.

Referring back to FIG. 12, selection of a test module 414h-j from the test box 410 directs execution of the program 15a to provide a testing sequence to help test the user on patient care protocols, such as maternal and neonatal resuscitation, and other responses to emergency scenarios. The program 15a paces through the steps of a patient distress scenario, giving the user a predetermined time to respond or complete the task required, thus enabling the user to experience the pressure of an emergency situation. For example, the program 15a may test the user by presenting choices from which the user must select in order to treat the patient, wherein the user must complete the correct choice before the sequence proceeds to the next event. The program 15a enables the user to enable, disable, or check the virtual instruments 12 and sensors 30 for connection to supply input to the CIM 16.

If the virtual instruments 12 (FIG. 2) are enabled, the user may implement patient care activity on the simulator 14 using the virtual instruments 12, while having the results and quality of response being monitored by the program 15a. Alternatively, the user may use software-simulated instruments 12' (FIG. 1b) generated by the program 15a. The program 15a advances through the scenario until the patient recovers, and provides a running critique of the user's responses, with an explanation of each incorrect choice or action. Features of the test modules 414h-j include items that enable the user to specify that action sequences prescribed by the scenario comprise a predetermined number of compression/ventilation cycles on the simulator 14, or to allow the user to record the time and magnitude of the compression and ventilation activity performed on the simulator 14, or to select among a group of choices for hearing realistic sounds.

Testing may be defined by the program 15a, as above, or by the user. For example, selection of the Codemaker Test module 414*j* (FIG. 12) allows a first user, for example, an instructor, to create a scenario to test a second user, for example, a student. The first user may input preliminary data to define the patient simulator of the testing scenario by entering a set of preliminary patient parameters regarding information such as sex, weight, and age, as well as patient indications, vital signs and cardiac rhythms which will be realistically reflected in the vital signs monitor 406 (FIG. 12). An instructor defined testing system allows the instructor to test the student on local, national, or international patient care protocols. Many algorithms are selectable by opening files, including BLS, ACLS, Pediatric, and Obstetric (OB) emergencies. Other algorithms may be created and stored, and algorithms may be linked together as well. Benefits of this module include flexibility for instruction and the ability to detect mastery of the subject. An instructor-defined algorithm would presumably vary from well-known, structured algorithms, and thus avoid the problem of rote memorization of responses by the student.

Action may be taken in response to the conditions by the student, for example, the student may select among virtual instruments to use to render patient care activities. The student may then perform the patient care activities virtually, or using the tangible simulator.

Use of the modules 414*k-p* of the virtual instruments tutor box 52 provides information about instruments commonly used in child birthing scenarios. In some instances, opportunities to practice using some of the virtual instruments 12 in patient care protocols with the simulator 14 are provided.

Figure 14:
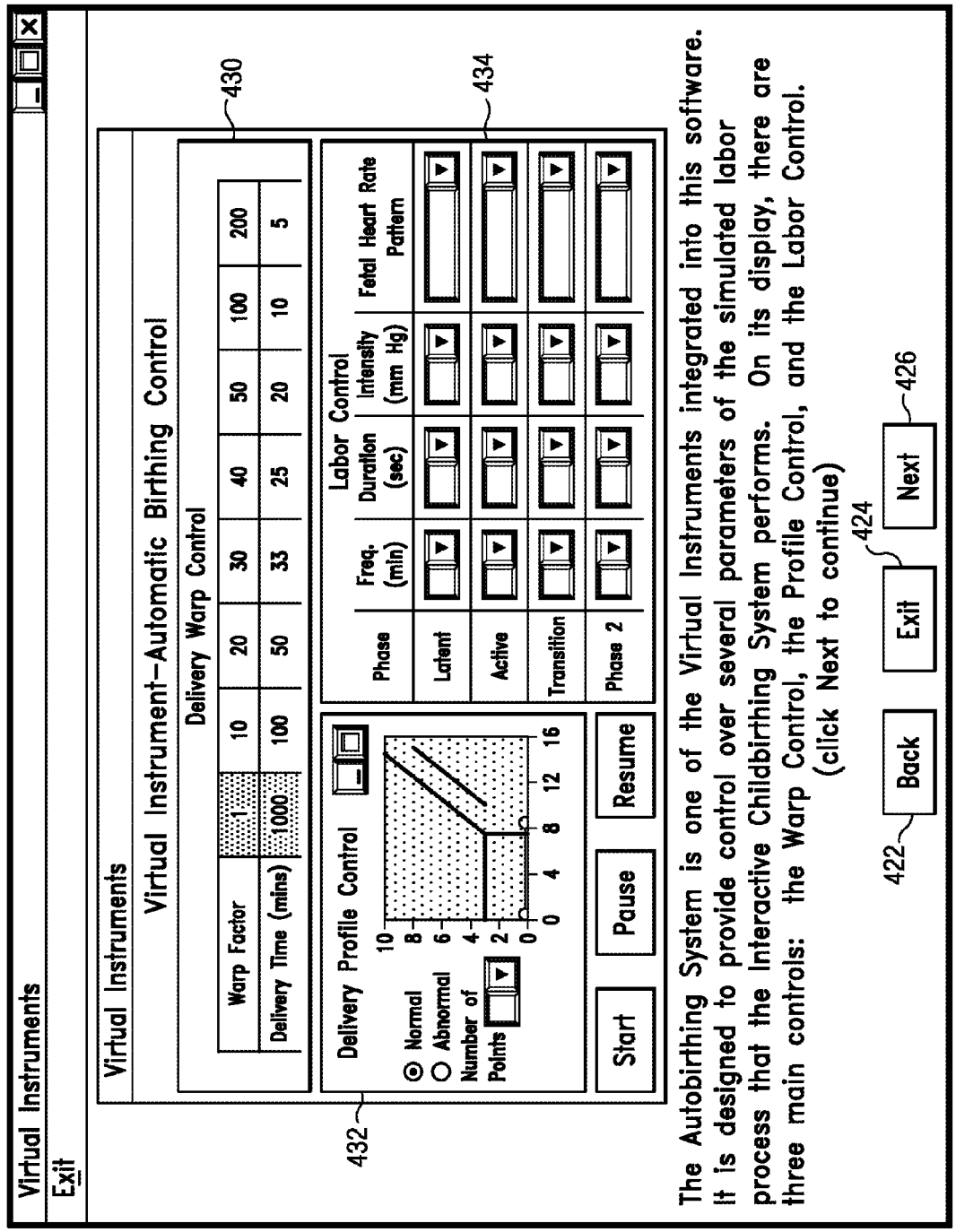
Figure 15:
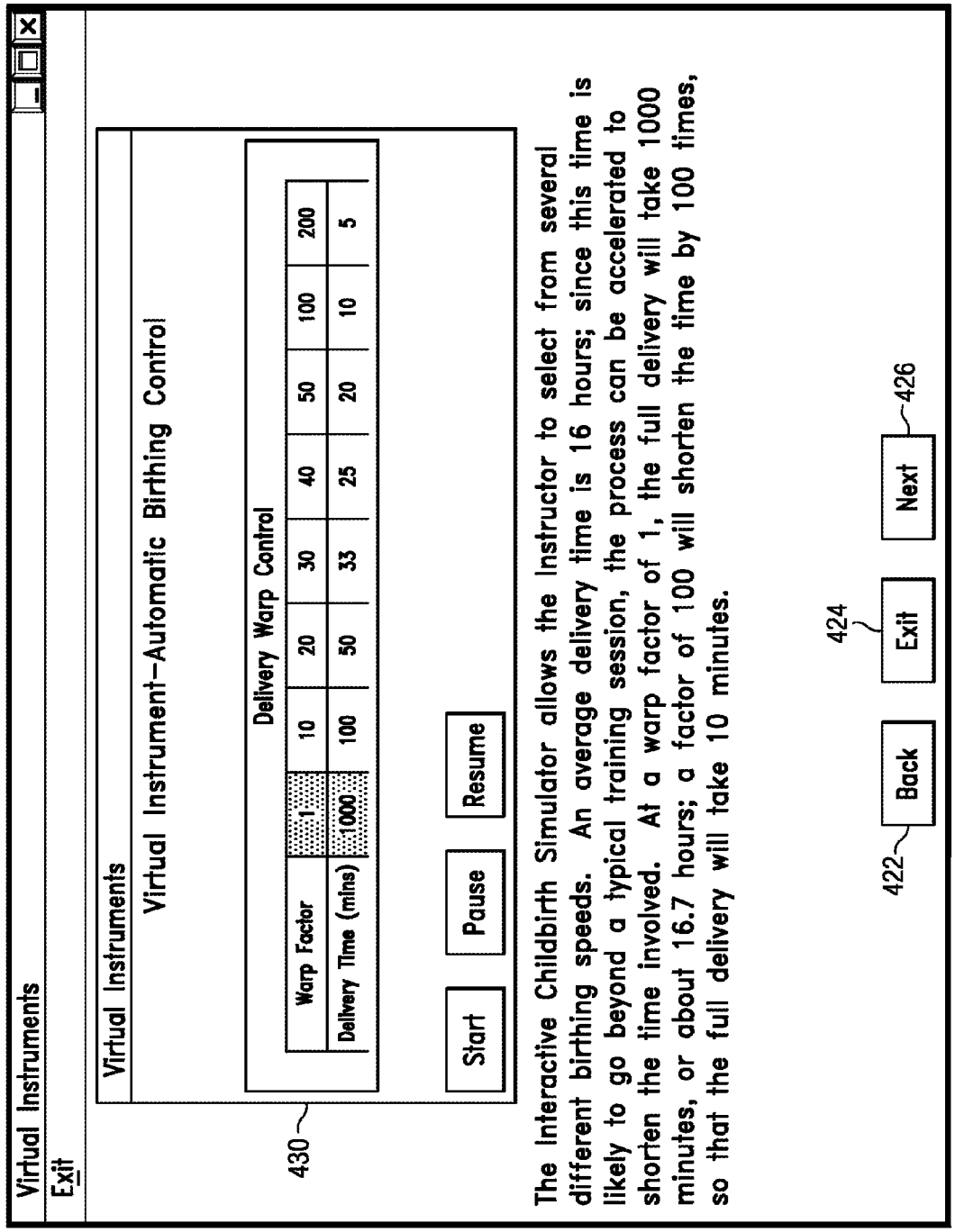

Turning now to FIGS. 14 and 15, the entire child birthing process may be automated via the program 15*a*, with the user merely defining initial conditions, such as delivery time 430, delivery profile 432, and contraction intensity 434. The warp feature allows a full delivery to be condensed from 16 hours to 5 minutes. Child birthing then consists of placing the fetal simulator 302 on the projection 344, and placing the cover 324 on the maternal simulator 300. The program 15*a* also offers a varying rate for progress of the ram 346, i.e., the first few centimeters may proceed much more slowly than the last few centimeters to better simulate child birth.

Figure 16:
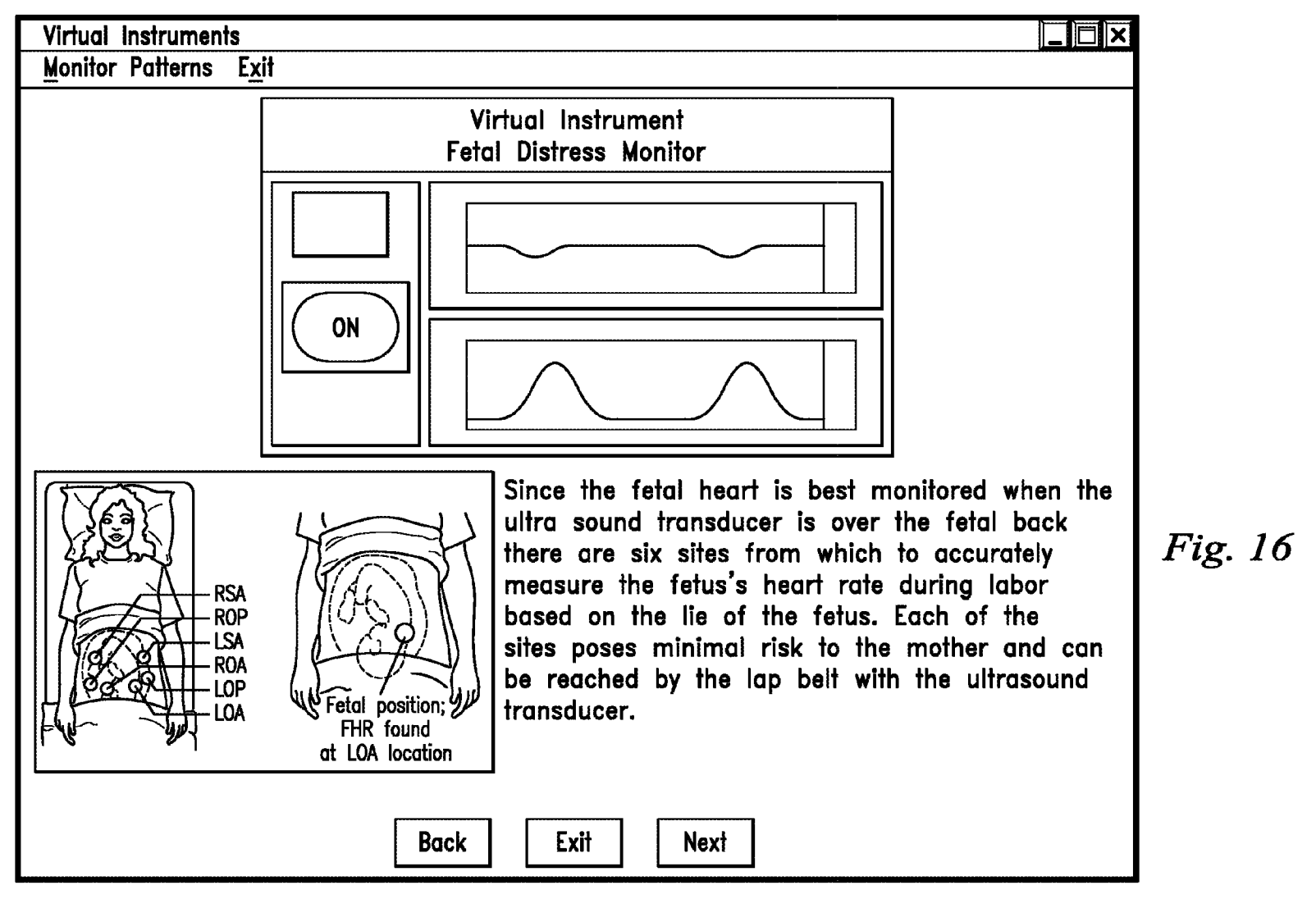

Referring to FIG. 16, if module 414*m* (FIG. 12) is selected, a series of screens are shown regarding the fetal distress monitor, with tutorial information. An exemplary fetal distress monitor box 436 is depicted, along with a selectable On button 436*a* for turning on the monitor. The fetal distress monitor 12*l* cooperates with the simulator 14, the fetal heart monitor is placed on the cover 324 of the maternal simulator 300 (FIG. 5*a*) and interacts with at least one sensor 30, while the contractions monitor interacts with another sensor 30 disposed on the cover.

Figure 17:
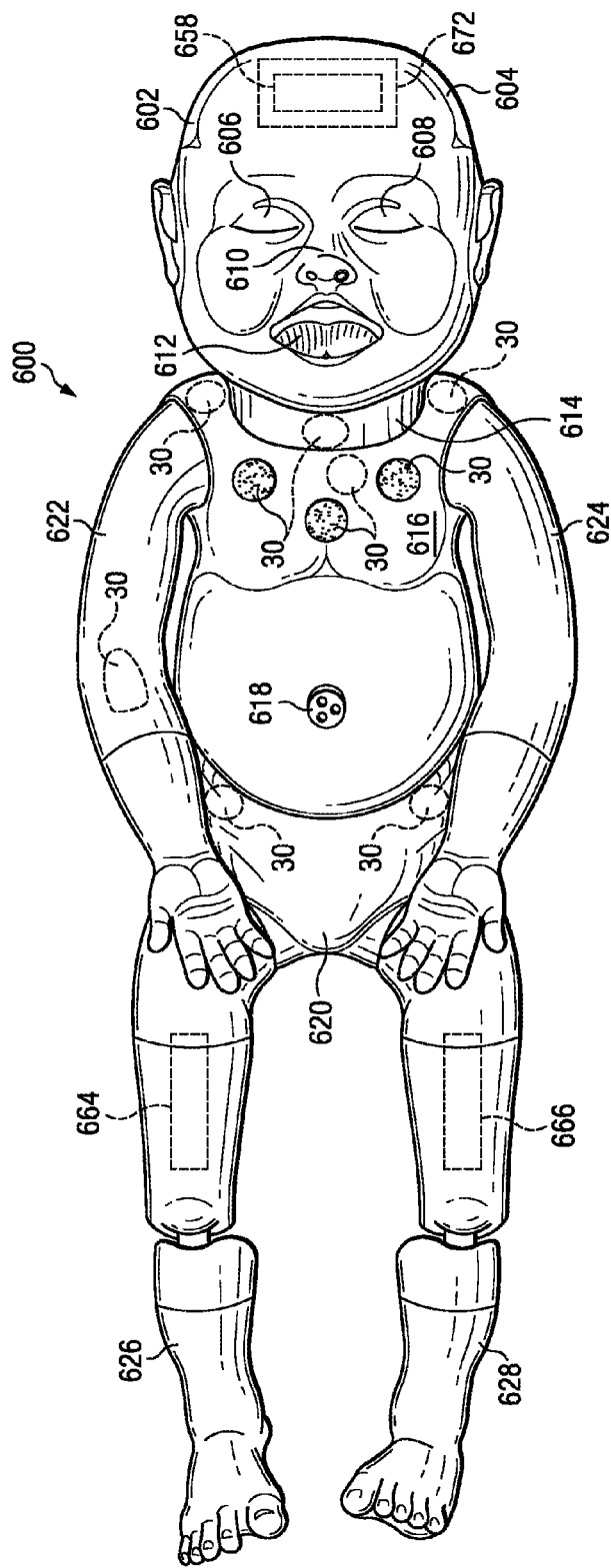
FIG. 17 is a perspective view of a neonatal embodiment of a patient simulator according to one embodiment of the present disclosure.

Referring to FIG. 17, a neonate simulator 600 may be used to replace the fetal simulator 302 to allow practice of neonatal resuscitation according to the program 15*a*. In one embodiment, the neonate simulator is substantially the size of an average sized neonate of 28 weeks gestational age. In another embodiment, the neonate simulator 600 is substantially the size of an average sized neonate of 40 weeks gestational age. The neonate simulator 600 exhibits many of the same features as the maternal simulator 300, including heart rate, pulse, oxygenation, and a variety of body sounds that can be detected using the virtual stethoscope 12*j* or a conventional stethoscope. Further, as described below the neonate simulator 600 is self-sufficient in that it does not require wired or tubed connection to any external devices for proper operation its numerous features, such as bulky external compressors and power supplies. The neonate simulator 600 is portable. In some embodiments the neonatal simulator is tetherless, such that it is functional without wired, tubed, or other physical connection to other external devices.

The neonate simulator 600 has a head 602, with hair 604, eyes 606 and 608, a nose 610, and a mouth 612. The head 602 is connected via a neck 614 to a torso 616. The torso 616 includes an umbilical site 618 that provides a site for catheterization. The torso 616 also includes an interchangeable genetalia site 620 that is adapted to receive both male and female genetalia pieces (not shown). Two arms 622 and 624 are connected to and extend from the upper portion of the torso 616. Two legs 626 and 628 are connected to and extend from the lower portion of the torso 616.

Sensors, generally denoted 30, may be disposed on the skin of the neonate simulator 600 (shown as stippled) and/or beneath the skin (shown in phantom) to provide various simulated features, as previously described. The torso 616 contains a simulated heart, lungs, and ribs for performing CPR. In one aspect, the heart and lungs are connected to pressure transducers as described above for the maternal simulator 300 for confirming airway ventilation and cardiac compression. The torso 616 also contains other components such as the power supply and wireless communication devices. In one embodiment, the power supply is a rechargeable pack of five lithium-ion cells. In one aspect, the power supply is positioned in the area normally reserved for the liver.

Figure 18:
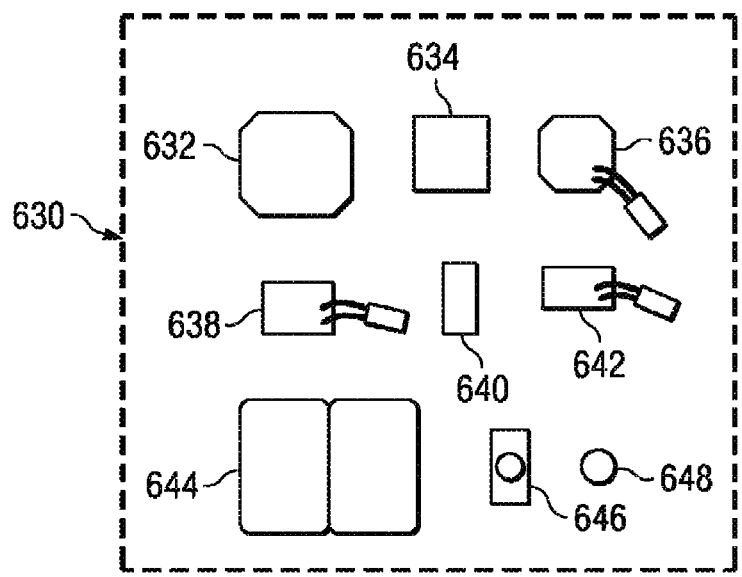
FIG. 18 is a perspective view of various modules for use with the neonatal simulator of FIG. 17.

To fit all of the functionality of the neonatal simulator 600 into a manikin the size of a neonate of 28 or 40 weeks gestational age, the numerous electronics must be appropriately sized and precisely positioned within the manikin where they are needed. In one embodiment, the electronic components of the neonate simulator 600 are grouped into smaller modules based on function, rather than placed on a general motherboard. For example, FIG. 18 illustrates one possible set of modules 630 for use in the neonate simulator 600. The set of modules 630 includes a master module 632 for interfacing the neonate 600 with the computer; a module 634 for generating the ECG signal; a module 636 for generating sounds such as heart, lungs, voice, and Korotkoff sounds; a module 638 for sensing pressure such as chest compression, airway ventilation, blood pressure, and compressor pressure; a module 640 for monitoring intubation; a module 642 for driving valves and LEDs; a module 644 for providing a connection such as a wireless interface and USB-RF interface; a module 646 for producing voice sounds; and a module 648 for producing sounds other than voice. One or more of these modules 632-648 can be combined to create any number of simulation features for the neonate simulator 600.

Figure 19:
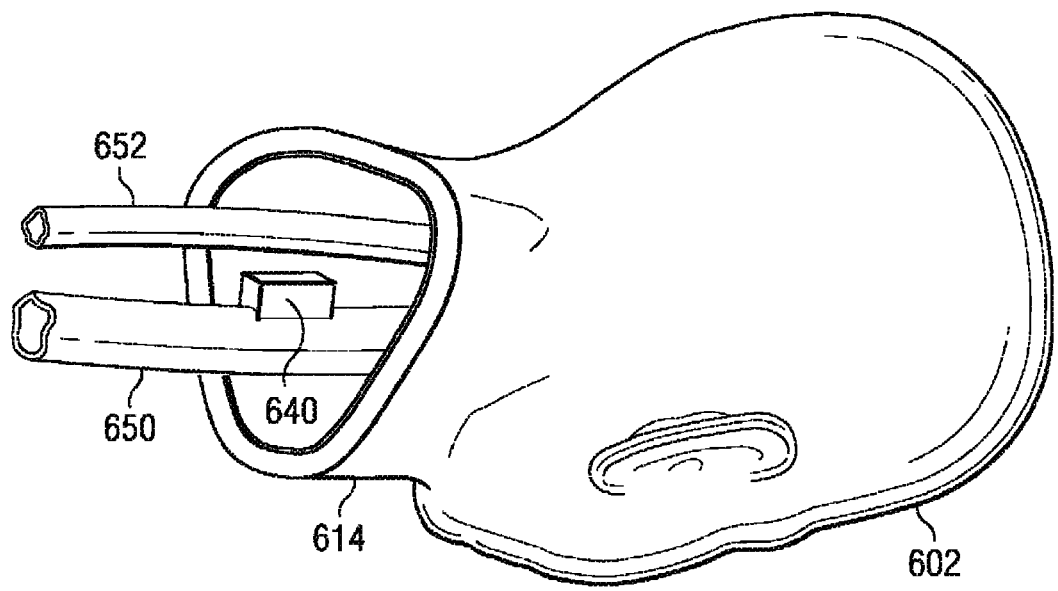
FIG. 19 is a perspective view of a cutaway portion of the neonatal simulator of FIG. 17.

Referring to FIG. 19, the neonate simulator 600 includes a realistic airway 650 accessible via the mouth 612 and nose 610. The airway 650 is capable of accepting conventional airway adjuncts and a sensor, such as module 640, is positioned adjacent the airway for determining whether an airway adjunct has been placed, or whether a fluid has passed through the airway. In one embodiment, the module 640 is an optical sensor that monitors the position of an airway adjunct, such as an endotrachial tube, and determines the adjunct is positioned too high, too low, or just right. The neonate simulator 600 also includes a simulated esophagus 652 that extends into the torso 616 to a simulated stomach.

Figure 20:
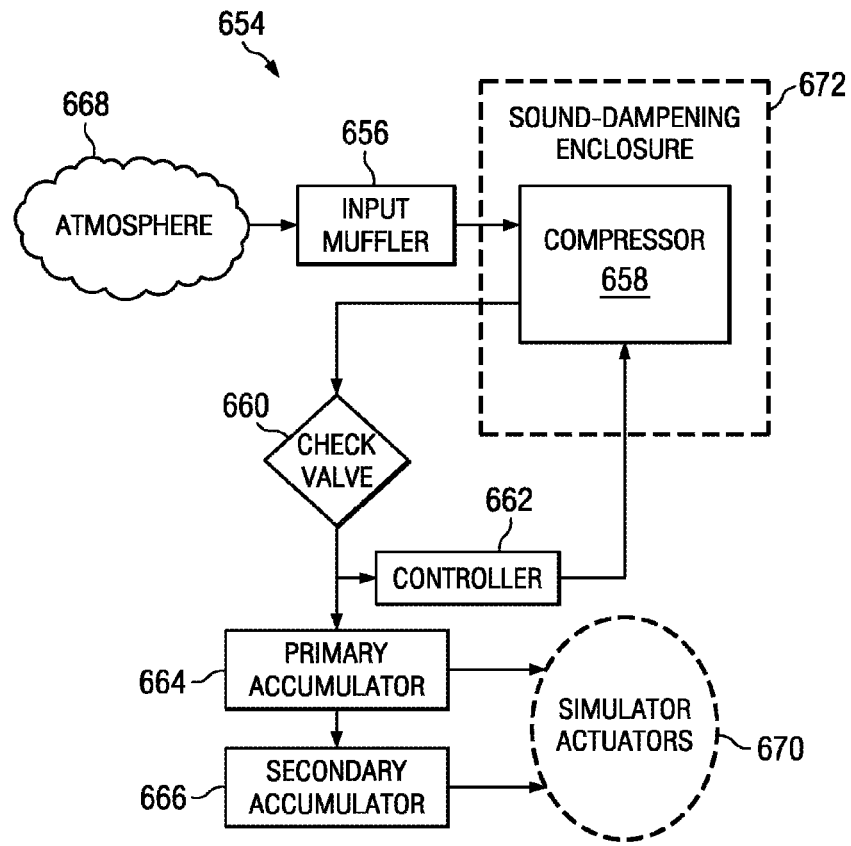
FIG. 20 is schematic view of an air supply system of the neonatal simulator of FIG. 17.

Referring to FIG. 20, the neonate simulator 600 also includes an air supply system 654 to simulate breathing, pulse, and associated physiological conditions of the neonate. The air supply system 654 includes a muffler 656, a compressor 658 (that may be a single diaphragm compressor such as model T2-03-E, available from T-Squared Pumps of New Jersey), a check valve 660 (appropriate valves may be obtained from Gulf Controls of Florida), a compressor controller 662, a primary accumulator 664, and a secondary accumulator 666. The compressor can alternatively be a rotary compressor or other suitable compressor.

In operation, the air supply system 654 provides pressured air to the neonate simulator 600 as follows. Air from the atmosphere 668 or a reservoir enters the compressor through the input muffler 656. The compressor controller 662 is utilized to maintain the pressure in the primary accumulator 664. A check valve 660 ensures air flow is in the proper direction. A pressure regulator (not shown) can be used to maintain a predefined pressure in the secondary accumulator. The primary and secondary accumulators are connected to actuators of the neonate simulator 600 for controlling supply of air. In one embodiment, the primary accumulator is connected to an actuator for controlling the supply of air to airway 650. In one embodiment, the secondary accumulator is connected to an actuator for controlling the supply of air to the lungs. The compressor controller 662 selectively provides power to the compressor 658 to maintain the desired pressure in the primary accumulator 664. In one embodiment, the approximate desired pressure of the primary accumulator is between 4.5-5.5 psi and the approximate desired pressure of the secondary accumulator is 1.5 psi. In some embodiments the air supply system 654 is further connected to the simulated circulatory system to provide simulated pulses or otherwise facilitate the simulated circulatory system.

The components of the air supply system 654 are positioned, insulated, and muffled to minimize the noise produced by the system. Since users will be utilizing stethoscopes to assess heart and breathing sounds of the neonate simulator 600, excessive noise from the air supply system 654 can interfere with and distract the user. To this end, portions of the air supply system 654 may be stored in the head 602 and extremities (arms 622, 624 and legs 626, 628) of the neonatal simulator 600.

For example, in one embodiment the compressor 658, the check valve 660, and the compressor controller 662 are positioned in the head 602 and the mufflers and accumulators are positioned in the legs 626, 628. The noise created by the components in the head is shielded by a sound dampening enclosure 672, illustrated schematically in FIG. 20. In one embodiment, the sound dampening enclosure 672 is a bilayer system having a first layer serving as an acoustic barrier and a second layer serving as a mass barrier. In one aspect, the acoustic barrier and the mass barrier are formed of noise abatement materials from EAR Specialty Composites. Further, the exhaust air created by the compressor 658 is ported down into legs 626, 628 of the simulator 600. Each leg 626, 628 includes a muffler system and an air reservoir. The muffler system dampens the "noisy" exhaust air to provide the air reservoir with a supply of "quiet" air for use by the neonate simulator 600 for the breathing and pulse simulations. In one aspect, the legs 626, 628 themselves serve as the air reservoirs and are sealed to prevent leakage.

Figure 21:
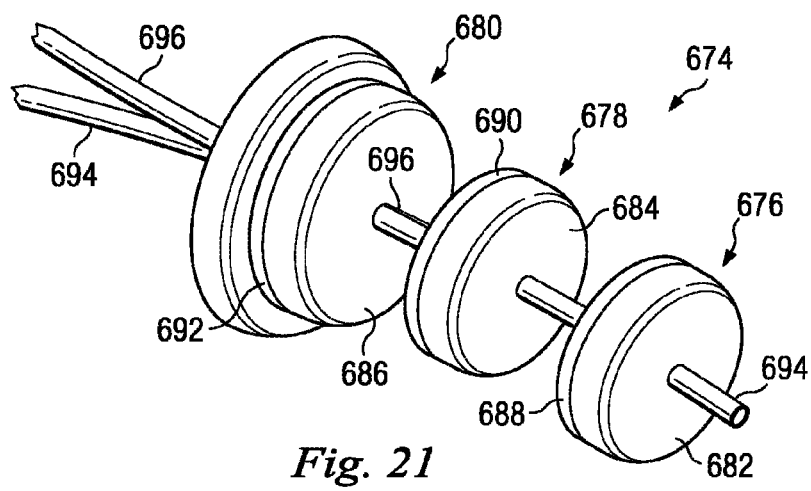
FIG. 21 is a perspective view of a cutaway portion of a muffler for use with the air supply system of FIG. 20.

FIG. 21 shows an exemplary embodiment of a muffler system 674. The muffler system 674 has three separate portions 676, 678, and 680 that dampen the sound from the noisy air. Each portion 676, 678, 680 has a first layer 682, 682, and 686, respectively, that serves as an acoustic barrier and a second layer 688, 690, and 692, respectively, that serves as a mass barrier. In one aspect, the acoustic barrier and the mass barrier are formed of the same noise abatement materials from EAR Specialty Composites as the sound dampening enclosure 672 described above. The noisy air is ported into the muffler system through a tube 694. The quiet or dampened air then exits the muffler through a tube 696. In one embodiment, the each leg 626, 628 is lined with noise abatement material in addition to the muffler system to further muffle and dampen any noise.

In one embodiment the hands and feet as well as the face and upper torso change color based upon proper oxygenation or an oxygen deficit. As oxygenation decreases, the extremities (peripheral cyanosis) change color first, followed by the face and upper torso (central cyanosis). Such change is reversible as oxygenation is improved. In one embodiment, the amount of time the neonate is without oxygen determines where the color and corresponding vital signs start, and the effort that is required to successfully bring the neonate back to healthy condition. In some embodiments, the simulator includes a mechanism for independently changing the color of the central portion and the peripheral portions. The mechanism, in some embodiments, utilizes blue LEDs or other lighting to simulate cyanosis.

In one embodiment, the thermochromatic system is logically linked to the program 15a, for example, an instructor defines the condition of the neonate. Afterwards, coloration is responsive to CPR quality being performed by a user, improving, worsening, or remaining the same. For comparison, an adult can tolerate between 5-10 minutes without oxygen. A pregnant mother or the maternal simulator 300 uses oxygen more quickly than a normal adult and, therefore, is affected more quickly. A neonate, on the other hand, can tolerate on the order of 15 minutes without oxygen, with death in about 30 minutes. Thus, if the hypoxic event is 5-7 minutes the neonatal simulator 600 will "pink up" rather easily. If the hypoxic event is 12-15 minutes then recovery will be slower and requires more effort on the part of the user. Further, if the hypoxic event is more than 20 minutes, then it is very difficult even with the use of epinephrine for the user to get the neonatal simulator 600 to "pink up," and the neonatal simulator 600 can die or suffer some lifelong malady, such as cerebral palsy.

Figure 22:
FIG. 22 is a screen display view generated by a program according to one embodiment of the present disclosure.
Figure 23:
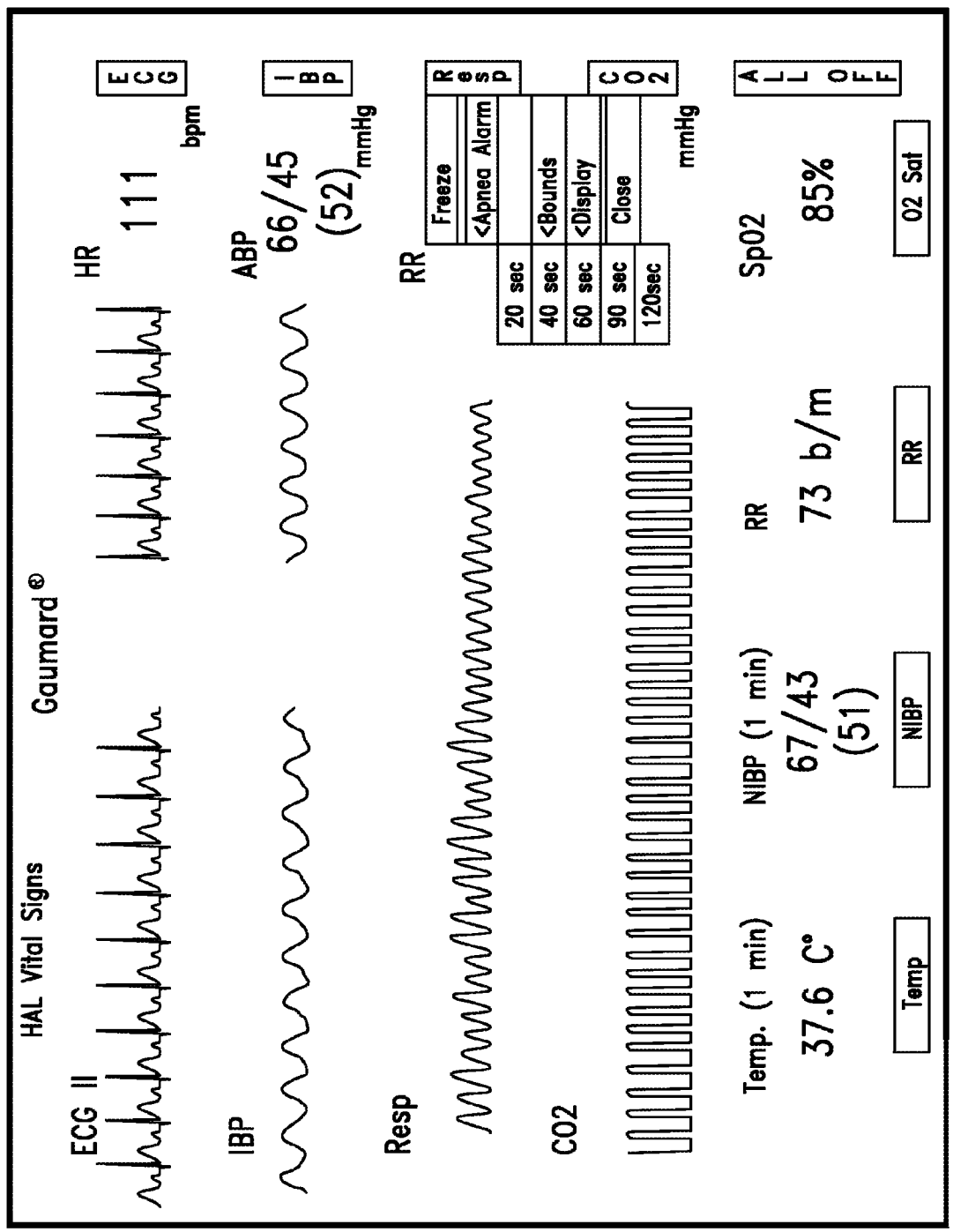
FIG. 23 is an output display view of simulated vital signs of the neonatal simulator of FIG. 17 according to one embodiment of the present disclosure.

In one embodiment, the instructor can select the degree of cyanosis of the neonatal simulator 600, as shown in the screen display 700 of FIG. 22. Though not shown in the screen display 700, the instructor may also select or define various other attributes of the neonatal simulator 600, such as the muscle tone in the arms 622, 624 and the legs 626, 628 (e.g., limp, well-flexed, motion, etc.) and the "speech" of the neonatal simulator 600 (e.g., crying, grunting, stridor, etc.). The vital signs and recovery of the neonatal simulator 600 can be monitored using a display 702, as shown in FIG. 23. The program also provides for an override if coloration changes are not desired.

Referring now to FIGS. 24-27, shown therein is an engagement system 740 that is an alternative embodiment to the receiver 342 and projection 344 system for selectively engaging the fetal or neonatal simulator 302, 600 to the maternal simulator 300. The engagement system 740 includes a mechanism 742 that engages a mechanism 744. In some embodiments, the mechanism 742 is disposed within the fetal or neonatal simulator 302, 600 and the mechanism 744 is disposed within the maternal simulator 300. In one embodiment, the mechanism 742 is adapted to replace the receiver 342 and the mechanism 744 is adapted to replace the projection 744. In other embodiments, the mechanism 742 is disposed within the maternal simulator 300 and the mechanism 744 is disposed within the fetal or neonatal simulator 302, 600.

Referring more specifically to FIG. 25, the mechanism 742 includes a housing 745 with an opening 746 extending therethrough. In the current embodiment the opening 746 is centrally located and substantially cylindrical. In other embodiments, the opening 746 can have various other cross-sectional shapes, including polygon, irregular, and other shapes. The mechanism 742 also includes a locking portion 748. The locking portion 748 and housing 745 can be permanently secured together (e.g. glued) or temporarily secured together (e.g. threaded engagement). Further, the locking portion 748 and/or the housing 745 may include additional features not shown to facilitate the engagement between the two pieces. In other embodiments the housing 745 and the locking portion 748 are an integral piece.

As shown in FIG. 26, the locking portion 748 includes a body portion 749. The body portion 749 is adapted to mate with the opening 746 of the mechanism 742. Thus, in the current embodiment the body portion 749 is substantially cylindrical, but in other embodiments may have other cross-sectional shapes to match opening 746. The locking portion 748 further includes an actuator 750 for moving locking pins 752 from an extended position, shown in FIG. 26, to a retracted position. In one embodiment the retracted position of the locking pins 752 is substantially within the body portion 749 of the locking portion. As described below, the selective extension and retraction of the locking pins 752 cause selective engagement of the mechanism 742 with the mechanism 744. In this manner the fetal and neonatal simulators 302, 600 are selectively engaged with the maternal simulator 300. In some embodiments, the actuator 750 is selective actuated by a solenoid. In some embodiments, the solenoid is disposed within the fetal or neonatal simulator 302, 600 or maternal simulator 300 adjacent the actuator 150. In some embodiments, the solenoid is located within the mechanism 742. In some embodiments, the solenoid is actuated via wireless device or a computer system such that an instructor can selectively release the fetal or neonatal simulator.

Referring more specifically to FIG. 27, the mechanism 744 includes a body portion 754. In the current embodiment, the body portion 753 is substantially cylindrical, but in other embodiments has other cross-sectional shapes. The mechanism 744 also includes an engagement portion 754. The engagement portion 754 has a substantially square cross-sectional shape, but in other embodiments has other cross-sectional shapes. The engagement portion 754 further includes an opening 755 extending therethrough. The opening 755 is adapted to receive the locking portion 748 of the mechanism 742. The engagement portion 754 also includes locking openings 756. The locking pins 752 of the locking portion 748 are adapted to engage openings 756 when extended. When retracted, the locking pins 752 retract from the openings 756 releasing locking mechanism 748 from the engagement portion 754.

Referring to FIG. 28, shown therein is a system for providing selective rotation to the fetal or neonatal simulators 302, 600. The system is adapted to move the cam 348*a* between a first position for causing rotation of the fetal simulator and a second position that does not cause rotation of the fetal simulator. In this manner the system can be used to selectively rotate or not rotate the fetal simulator during a birthing simulation. In some embodiments, retracting the cam 348*a* to a position adjacent the track 347*a* prevents rotation of the fetal simulator. In some embodiments, the cam 348*a* is further moveable to an intermediate position that causes some rotation of the fetal simulator, but less rotation than the first position. In some embodiments, the cam 348*a* is moveable between a plurality of intermediate positions each allowing a different amount of rotational movement. In some embodiments, the plurality of intermediate positions and the amount of rotation are continuous. In other embodiments, the plurality of intermediate positions and the amount of rotation are discrete.

The system includes a solenoid 760 that is adapted to selectively retract the cam 348*a*. The solenoid 760 is a connected to the cam 348*a* via an extension 761 and a fixation member 762. In one embodiment, the fixation member 762 is a bolt, screw, other threaded member, or other device for connecting the cam 348*a* to the extension 761. The cam 348*a* is connected to track 347*a* via fixation members 764 and 766. The fixation members 764 and 766 in some embodiments are bolts and nuts. The fixation members 764 and 766 also serve to prevent unwanted translational and rotational movement of the cam 348*a* with respect to track 347*a*. In other embodiments, the cam 348*a* and solenoid 760 may be adapted to translate along the track 347*a*. Further, in some embodiments the cam 348*a* may be adapted for rotational movement with respect to track 347*a*. In some embodiments, the position of the cam 348*a* is controlled remotely, and in some embodiments wirelessly, by the instructor or computer program. Though the system has been described with respect to track 347*a* and cam 348*a*, the same system is applied to track 347*b* and 348*b*.

Figure 29:
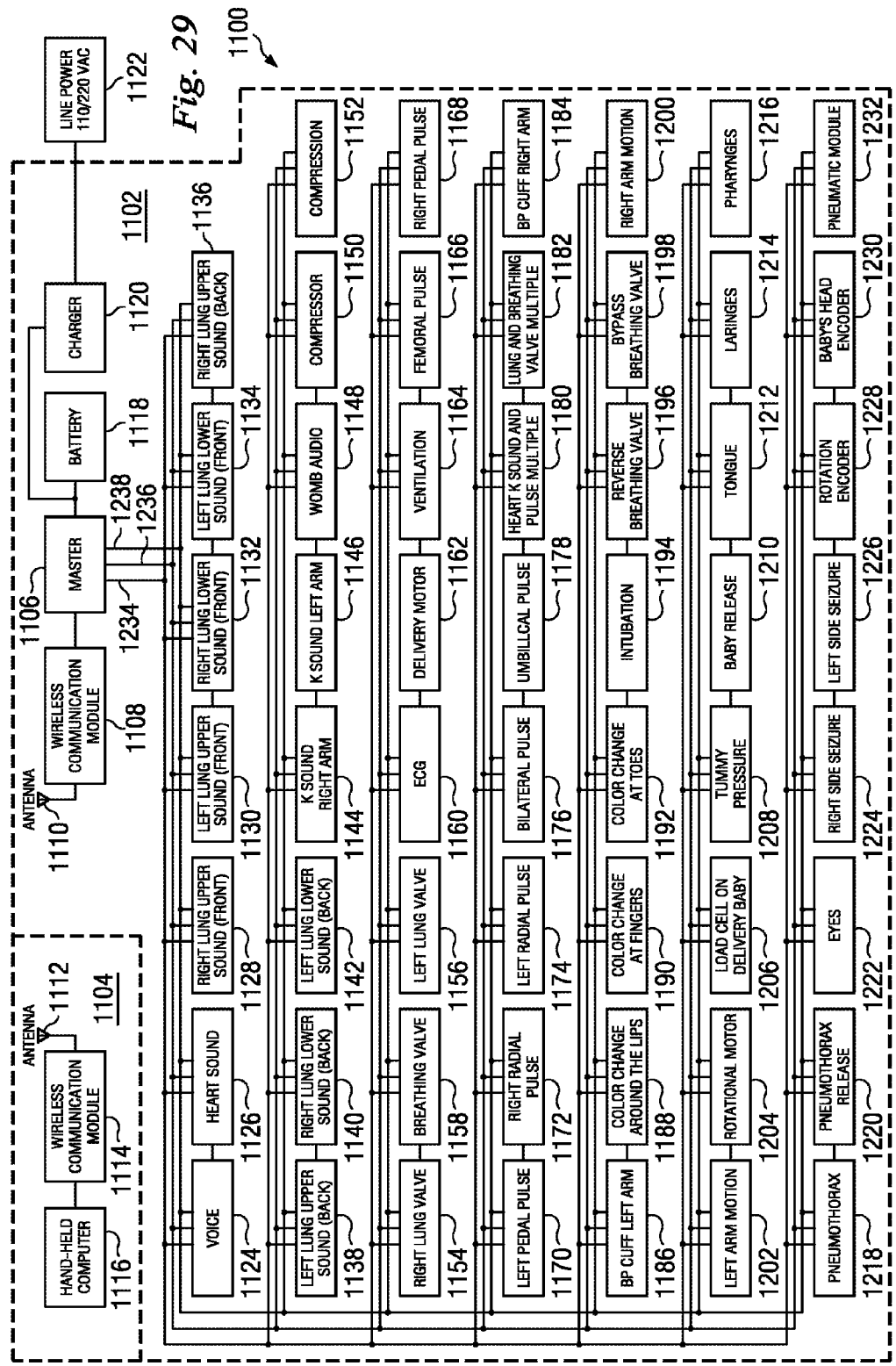
FIG. 29 is a diagrammatic schematic view of a patient simulator system according to one embodiment of the present disclosure.

FIG. 29 is a diagrammatic schematic view of a patient simulator system 1100 according to one embodiment of the present disclosure. The patient simulator system 1100 includes a patient simulator 1102 and a control system 1104. The patient simulator 1102 includes a plurality of modules for performing the various functions of the simulator. In some embodiments, each of the modules controls a particular function or group of functions of the simulator 1102. In that regard, the modules are appropriately sized for positioning within various portions of the simulator 1102. In some embodiments, the modules are positioned throughout the simulator adjacent to the region or area of the simulator 1102 related to the module's specific function or the associated body part of the simulator. Accordingly, the modules are distributed throughout the simulator rather than being grouped onto a single motherboard. In some embodiments, each of the modules is in communication with a master module 1106. As will be described in greater detail with respect to FIG. 32 below, in some embodiments the master module 1106 is configured to provide and control the power delivered to the modules and facilitate communication with and among the modules.

In the current embodiment, the patient simulator 1102 is in wireless communication with the control system 1104. In that regard, the patient simulator 1102 includes a wireless communication module 1108 and an antenna 1110. The wireless communication module 1108 and antenna 1110 are in communication with an antenna 1112 and a wireless communication module 1114 of the control system 1104. In the current embodiment the wireless communication module 1114 is connected to or in communication with a computer system 1116. In that regard, the computer system 1116 is a laptop or tablet PC in some instances. Generally, the computer system 1116, or the control system 1104 as a whole, is any combination of hardware and software capable of controlling or defining various factors and/or functions of the patient simulator 1102.

In that regard, the computer system 1116 or the control system 1104 comprises one or more of a microprocessor, an input device, a storage device, a video controller, a system memory, a display, and a communication device all interconnected by one or more buses. The storage device could be a floppy drive, hard drive, CD-ROM, optical drive, or any other form of storage device. In addition, the storage device may be capable of receiving a floppy disk, CD-ROM, DVD-ROM, or any other form of computer-readable medium that may contain computer-executable instructions. Further communication device could be a modem, network card, or any other device to enable the system to communicate with other devices including the simulator 1102. It is understood that any system could represent a plurality of interconnected (whether by intranet or Internet) computer systems, including without limitation, personal computers, mainframes, PDAs, and cell phones.

A computer system typically includes at least hardware capable of executing machine readable instructions, as well as the software for executing acts (typically machine-readable instructions) that produce a desired result. In addition, a computer system may include hybrids of hardware and software, as well as computer sub-systems. Hardware generally includes at least processor-capable platforms, such as client-machines (also known as personal computers or servers), and hand-held processing devices (such as smart phones, personal digital assistants (PDAs), or personal computing devices (PCDs), for example). Further, hardware may include any physical device that is capable of storing machine-readable instructions, such as memory or other data storage devices. Other forms of hardware include hardware sub-systems, including transfer devices such as modems, modem cards, ports, and port cards, for example.

Software includes any machine code stored in any memory medium, such as RAM or ROM, and machine code stored on other devices (such as floppy disks, flash memory, or a CD ROM, for example). Software may include source or object code, for example. In addition, software encompasses any set of instructions capable of being executed in a client machine or server. Combinations of software and hardware could also be used for providing enhanced functionality and performance for certain embodiments of the present disclosure. One example is to directly manufacture software functions into a silicon chip. Accordingly, it should be understood that combinations of hardware and software are also included within the definition of a computer system and are thus envisioned by the present disclosure as possible equivalent structures and equivalent methods.

Computer-readable mediums include passive data storage, such as a random access memory (RAM) as well as semi-permanent data storage such as a compact disk read only memory (CD-ROM). In addition, an embodiment of the present disclosure may be embodied in the RAM of a computer to transform a standard computer into a new specific computing machine. Data structures are defined organizations of data that may enable an embodiment of the present disclosure. For example, a data structure may provide an organization of data, or an organization of executable code. Data signals could be carried across transmission mediums and store and transport various data structures, and, thus, may be used to transport information in some embodiments of the present disclosure.

The system may be designed to work on any specific architecture. For example, the system may be executed on a single computer, local area networks, client-server networks, wide area networks, internets, hand-held and other portable and wireless devices and networks. A database may be any standard or proprietary database software, such as Oracle, Microsoft Access, SyBase, or DBase II, for example. The database may have fields, records, data, and other database elements that may be associated through database specific software. Additionally, data may be mapped. Mapping is the process of associating one data entry with another data entry. For example, the data contained in the location of a character file can be mapped to a field in a second table. The physical location of the database is not limiting, and the database may be distributed. For example, the database may exist remotely from the server, and run on a separate platform. Further, the database may be accessible across the Internet. Note that more than one database may be implemented.

The wireless communication between communication modules 1108 and 1114 is performed using any wireless protocol capable of transferring data between the patient simulator 1102 and the control system 1104. In one particular embodiment, the wireless protocol between the communication modules 1108 and 1114 utilizes the 802.15 protocol. In other embodiments, the wireless communication utilizes other communication protocols including, but not limited to other IEEE 802 protocols and telecommunication network protocols.

The patient simulator 1102 includes a power supply 1118. In the present embodiment, the power supply 1118 is a rechargeable battery. In that regard, the power supply 1118 is connected to a charger 1120. The charger 1120 is configured to recharge the power supply 1118. In that regard, the charger 1120 is configured for communication with an external power supply 1122. In the current embodiment, the external power supply 1122 is a wall outlet or standard line power supply. In other embodiments, the external power supply 1122 is configured for wireless communication with the charger 1120 or power supply 1118 such that the power supply 1118 may be recharged wirelessly, such as by inductive coupling or other wireless charging means. In some embodiments, the charger 1120 comprises a backup power supply.

As mentioned above, the patient simulator 1102 includes a plurality of modules for controlling the various features and functions of the simulator. In that regard, various modules may be combined to create a simulator with specific features as desired by a customer or user. In this manner, the modules included in the patient simulator 1102 may be selected based on the intended use of the simulator. The modular nature of the function-specific modules allows the simulator 1102 to include those features that a customer desires initially in any combination, but also allows a customer to add additional features or disable included features later. One specific combination of available modules for use in the simulator 1102 will now be described with respect to FIG. 29. However, no limitation is intended thereby. In that regard, it is understood that the patient simulator 1102 may include additional, fewer, or other combinations of modules in other embodiments. Various combinations of the modules illustrated in FIG. 29 are particularly suited for use in different types of patient simulators. For example, in some instances combinations of modules are selected for use in a maternal simulator for simulating a birthing sequence including the birthing of a fetal simulator. In other embodiments, combinations of modules are selected for use in patient simulators of various sizes and ages from neonatal to full grown adult and therebetween. Accordingly, a patient simulator system according to the present disclosure may include some or all of the modules illustrated in FIG. 29.

The patient simulator 1102 includes a voice module 1124. The voice module 1124 is in communication with the master module 1106, which is in communication with the control system 1104. The voice module 1124 is an audio module configured to emit sounds simulating a patient's voice. In that regard, the particular sounds emitted by the voice module 1124 are controlled in some embodiments by a user through the control system 1104. In some embodiments, the control system 1104 includes a plurality of stored or prerecorded sounds that may be selected from and played back by the voice module 1124.

In some embodiments, the sounds include one or more of various answers to questions medical personnel might ask a patient and/or sounds a patient might make. For example, the answers may include various complaints (e.g., "ankle broken", "arm broken", "blood in toilet", "can't catch breath", "can't move", "can't move legs", "chest hurts", "coughing up blood", "elephant on chest", "feel dizzy", "feel nauseous", "feel weak", "heart beating fast", "heart pounding", "heart trying to jump", "hurt all over", "hurts when breathing", "I've been cut", "jaw hurts", "left arm hurts", "leg is broken", "passing blood", "peeing blood", "pooping blood", "puking blood", "short of breath", "shoulder hurts", "somebody shot me", "stomach hurts", "worst headache", and/or other complaints), confused answers (e.g., "Are you a doctor?", "I don't remember", "What happened?", "Who are you?", and/or other confused answers), location answers (e.g., "in my arm", "in my chest", "in my leg", "in my shoulder", "left side", "right side", and/or other location answers), descriptive answers (e.g., "a little bit", "a lot", "I can't move it", "it's dull", "it's sharp", "not pain . . . pressure", "pain in center chest", "sharp tearing pain", and/or other descriptive answers), evasive answers (e.g., "I feel fine", "take me to a hospital", and/or other evasive answers), generic answers (e.g., "yes", "no", "maybe", and/or other generic answers), history answers (e.g., "asthma", "diabetes", "emphysema", "had heart attack", "high blood pressure", and/or other history answers), occurrence answers (e.g., "once", "twice", "three times", "four times", "since last night", "since this morning", "since this afternoon", and/or other occurrence answers). In addition to the answers and responses noted above, the sounds include coughing, gagging, choking, moaning, screaming, and/or other sounds a patient makes. In that regard, each of the sounds may have different levels or types. For example, in some instances the sounds include different severity of coughs, gags, moaning, screaming, and/or other sounds.

In some embodiments, the control system 1104 is in communication with the voice module 1124 such that a user or teacher speaks into a microphone or other sound communication device associated with the control system and the teacher's words or sounds are emitted from the voice module 1124. In some embodiments, the user or teacher's input may be conditioned using audio amplifiers or sound boards to alter the sound of the voice emitted from the voice module 1124. For example, in some embodiments the input sound is conditioned to simulate a hoarse patient, a patient with a blocked air passage, or other mental or physical medical condition of the patient. In that regard, the teacher may selectively activate various types of audio conditioning based on a desired effect. The voice module 1124 and the corresponding voice simulation are utilized as part of an overall medical scenario simulation in some embodiments.

The patient simulator 1102 also includes a heart sound module 1126. The heart sound module 1126 is an audio module configured to emit sounds to simulate the natural sounds of a patient's heart. In that regard, the sounds of the heart sound module 1126 include one or more of sounds to simulate the patient's heart rate and cardiac rhythm (e.g., sinus, atrial tachycardia, multifocal atrial tachycardia, atrial flutter, atrial fibrillation, junctional, idioventricular, ventricular tachycardia (uni.), ventricular tachycardia (multi.), supraventricular tachycardia, ventricular flutter, ventricular fibrillation, agonal, asystole, LBBB, RBBB, $1^{st}$ degree AVB, $2^{nd}$ degree AVB (Type I), $2^{nd}$ degree AVB (Type II), $3^{rd}$ degree AVB, Q-wave infarction, ST segment elevation, ST segment depression, T-wave inversion, atrial paced, AV sequential paced, vent. Pacemaker (artificial), and/or other cardiac rhythms). Further, the heart sounds may be normal, distant, non-existent, include a systolic murmur, S3, and/or S4. The control system 1104 and/or a user utilizing the control system determines what heart sounds and at what rate the sounds are produced in some embodiments. The sounds produced by the heart sound module 1126 are detectable via use of a stethoscope in some instances. In some embodiments, at least a portion of the heart sound module 1126—such as a speaker—is positioned within the simulator 1102 where the natural heart would be.

The patient simulator 1102 also includes lung sound modules 1128, 1130, 1132, 1134, 1136, 1138, 1140, and 1142. In particular, lung sound module 1128 is utilized to simulate sounds of the upper right lung towards the front of the simulator 1102; lung sound module 1130 is utilized to simulate sounds of the upper left lung towards the front of the simulator; lung sound module 1132 is utilized to simulate sounds of the lower right lung towards the front of the simulator 1102; lung sound module 1134 is utilized to simulate sounds of the lower left lung towards the front of the simulator 1102; lung sound module 1136 is utilized to simulate sounds of the upper right lung towards the back of the simulator; lung sound module 1138 is utilized to simulate sounds of the upper left lung towards the back of the simulator; lung sound module 1140 is utilized to simulate sounds of the lower right lung towards the back of the simulator 1102; lung sound module 1142 is utilized to simulate sounds of the lower left lung towards the front of the simulator 1102.

Each of the lung sound modules 1128, 1130, 1132, 1134, 1136, 1138, 1140, and 1142 is an audio module configured to produce sounds to simulate the natural sounds of a patient's lungs. In that regard, the lung sound modules 1128, 1130, 1132, 1134, 1136, 1138, 1140, and 1142 are configured to produce one or more of the following lung sounds in some embodiments: normal, none, wheezing, inspiration squeaks, crackles, rails, and/or other lung sounds. Further, the combination of lung sound modules 1128, 1130, 1132, 1134, 1136, 1138, 1140, and 1142 are utilized to simulate respiratory patterns including, but not limited to normal, Kussmaul's, Cheyne-Stokes, Biot's, apneusic, and/or other respiratory patterns. The combination of lung sound modules 1128, 1130, 1132, 1134, 1136, 1138, 1140, and 1142 are also utilized to simulate the respiratory rate of the patient. In that regard, the respiratory rate may be set at a constant rate and/or be set to change over time.

The patient simulator 1102 also includes a K-sound module 1144 for the right arm of the simulator and a K-sound module 1146 for the left arm of the simulator. Each of the K-sound modules 1144 and 1446 are configured to produce a simulated K-sound (Korotkoff sound). In that regard, the K-sound modules 1144 and 1146 are utilized to allow a user to take the blood pressure of the patient simulator 1102. Accordingly, the K-sounds produced by the modules 1144 and 1146 are determined based on a simulated heart rate and blood pressure. In some instances, the heart rate and blood pressure of the patient simulator 1102 are provided by a user or teacher via the control system 1104. The patient simulator 1102 also includes a womb audio module 1148 to simulate the sounds of the fetus within the womb of the mother. For example, in some embodiments the womb audio module 1148 is configured to simulate the heart beat of the fetus within the womb.

The patient simulator 1102 also includes a compressor 1150. The compressor 1150 is utilized to provide a compressed air supply to the various pneumatic devices of the simulator 1102. For example, in some embodiments the compressor 1150 is utilized to provide air to modules for simulating the lungs, pulses, contractions, tummy pressure, seizures, eye dilation, blinking, and/or other aspects of the patient simulator 1102. In some embodiments, the compressor 1150 provides pressurized air to one or more air reservoirs or accumulators that are then connected to the various pneumatic modules of the simulator 1102. In that regard, the air reservoirs may maintain different air pressures such that different pneumatic modules are connected to the air reservoir with the appropriate air pressure for its application. In some instances, the pneumatic modules of the patient simulator 1102 that utilize the compressor 1150 are configured to run at a relatively low air pressure, e.g., less than 10 psi in some embodiments and less than 5 psi in other embodiments. In some instances, the simulator 1102 includes two accumulators with one of the accumulators maintaining an air pressure of approximately 5 psi and the other accumulator maintaining an air pressure of approximately 1 psi. In other embodiments, the accumulators maintain other air pressures. Generally, however, the patient simulator 1102 and its associated components are configured to operate at low pressures, which helps prevent the introduction of water into the simulator associated with high pressure systems. The introduction of water into the simulator that results from using high pressure systems can cause damage to the simulator, increase the maintenance costs, and require additional components to remove or limit the amount of water within the simulator.

Further, the compressor 1150 is sized to fit entirely within the simulator 1102. In that regard, the compressor 1150 operates quietly so as not to interfere with the other simulation aspects of the simulator 1102. Accordingly, in some instances a muffler system is utilized to minimize the noise generated by the compressor 1150. The muffler system is utilized on the input, output, and/or both sides of the compressor in some embodiments. Further, the compressor 1150 is self-cooling in some instances. In one such embodiment, the compressor 1150 includes a plurality of metal pipes surrounding at least the compressor motor that intake air is passed through. The intake air passing through the metal pipes helps to dissipate the heat generated by the compressor 1150. Accordingly, the compressor 1150 is able to operate entirely within the simulator 1102 without overheating or disturbing the other simulation aspects of the simulator. This allows the simulator 1102 to be fully functional without attachment to a noisy, external, high pressure compressor.

The patient simulator 1102 also includes a compression module 1152. The compression module 1152 is configured to monitor the force of chest compressions applied to the simulator 1102. In that regard, the compression module 1152 is configured to monitor the pressure applied and based on that pressure determine whether the pressure is too high, too low, or within the desired range. The compression module 1152 is in communication with the master module 1106, such that the determination of whether the correct pressure is being applied is relayed to the control system 1104. In some embodiments, the simulator 1102 will trend towards recovery or further complications based on whether the correct pressure is applied. For example, if the chest compressions are within the desired range of pressures then the patient simulator may show signs of recovery. On the other hand, if the chest compressions are outside the desired range of pressures then the patient simulator may develop additional problems or symptoms and/or make it more difficult to recover the simulator from the present symptoms.

The patient simulator 1102 also includes a right lung valve 1154, a left lung valve 1156, and a breathing valve 1158. Together the right lung valve 1154, the left lung valve 1156, and the breathing valve 1158 control the flow of air into and out of the lungs of the simulator 1102. In that regard, each of the valves 1154, 1156, and 1158 comprise a pneumatic valve. In some embodiments, the breathing valve 1158 is utilized to control the respiratory rate of the simulator 1102. In that regard, the breathing valve 1158 opens and closes in order for the lungs to inflate and deflate at the desired rate. The right lung valve 1154 and the left lung valve 1156 are utilized to selectively disable the right and/or left lungs, respectively. Accordingly, in some embodiments when the right lung valve is opened it closes a 3-way air pilot valve such that air cannot flow from the breathing valve into the right lung. In such instances, air flows from the breathing valve solely into the left lung. Factors such as disablement of the lungs, respiratory rate, respiratory pattern, inspiratory rate, and/or disablement of the left or right lung is controlled by the valves 1154, 1156, and 1158 based on signals received from the control system 1104 via the master module 1106.

The patient simulator 1102 also includes an ECG module 1160. The ECG module is configured to emit an electrical signal that simulates the electrical activity of the heart of the simulator 1102. In some embodiments, the ECG modules are configured to provide signals associated with each of the 12 leads such that a 12-lead ECG signal is available to the user. In some embodiments, the ECG module 1160 is configured to emit signals that simulate the presence of a myocardial infarction in various parts of the heart. In some embodiments, the position of the myocardial infarction is selected via the control system 1104. Accordingly, the ECG module is utilized to train users to identify the onset of heart attacks and/or the associated symptoms identifiable via an ECG. The electrical signal of the ECG module is detectable by standard ECG equipment.

The patient simulator 1102 also includes a delivery motor module 1162. The delivery motor module 1162 is utilized to control the delivery of the fetus or baby from the simulator 1102 in embodiments where the simulator is a birthing simulator. In that regard, the delivery motor module 1162 is utilized to control the position of the baby within the mother simulator. Upon activation by the delivery motor module 1162, the delivery mechanism urges the baby out of the mother's womb. In some embodiments, the delivery mechanism will deliver the baby at least partially out of the mother's womb where the user completes delivery of the baby. In some embodiments, the delivery mechanism rotates the baby as it travels down the birth canal.

The patient simulator 1102 also includes a ventilation module 1164. The ventilation module 1164 is configured to monitor the use of a ventilation device applied to the simulator 1102. The ventilation device is a bag-valve mask in some instances. In other instances, the ventilation device is a user's mouth, such as in mouth-to-mouth resuscitation. The ventilation module 1164 is configured to monitor the pressure applied by the ventilation device and based on that pressure determine whether the pressure is too high, too low, or within the desired range. The ventilation module 1164 is in communication with the master module 1106, such that the determination of whether the correct pressure is being applied is relayed to the control system 1104. In some embodiments, the simulator 1102 will trend towards recovery or further complications based on whether the correct pressure is applied. For example, if the ventilation is within the desired range of pressures then the patient simulator may show signs of recovery. On the other hand, if the ventilation is outside the desired range of pressures then the patient simulator may develop additional problems or symptoms and/or make it more difficult to recover the simulator from the present symptoms.

The patient simulator 1102 also includes a femoral pulse module 1166. The femoral pulse module 1166 is a pneumatic module for simulating the femoral pulse of the simulator 1102. The patient simulator 1102 also includes a right pedal pulse module 1168 and a left pedal pulse module 1170. The left and right pedal pulse modules 1168, 1170 are configured to simulate the pedal pulses of the simulator 1102. In that regard, in some embodiments the pedal pulse modules 1168, 1170 are electrical modules configured to simulate the pedal pulses. In other embodiments, the pedal pulse modules 1168, 1170 are pneumatic modules configured to simulate the pedal pulses. The patient simulator 1102 also includes a right radial pulse module 1172 and a left radial pulse module 1174. The right and left radial pulse modules 1172, 1174 are pneumatic modules for simulating the radial pulses of the simulator 1102. The patient simulator 1102 also includes a bilateral pulse module 1176. The patient simulator 1102 also includes an umbilical pulse module 1178. The patient simulator 1102 also includes a multifunction module 1180 configured for simulating heart sounds, k-sounds, and/or pulses of the simulator. The patient simulator 1102 also includes multifunction module 1182 for use as a lung valve and/or breathing valve in the simulator 1102.

The patient simulator 1102 also includes a right blood pressure cuff module 1184 and a left blood pressure cuff module 1186. The left and right blood pressure cuff modules 1184 and 1186 are pressure modules configured to allow a user to take a simulated blood pressure of the patient simulator 1102. The blood pressure cuff modules 1184 and 1186 are configured for use with standard blood pressure monitors in some embodiments.

The patient simulator 1102 also includes a plurality of color change modules 1188, 1190, and 1192. In that regard, the color change module 1188 is configured for controlling color change around the lips of the simulator 1102; the color change module 1190 is configured for controlling color change around the fingers of the simulator; and the color change module 1192 is configured for controlling color change around the toes of the simulator. The color change modules 1188, 1190, and 1192 are utilized in some embodiments to simulate cyanosis of the patient simulator. Accordingly, the color change modules 1188, 1190, and 1192 are configured to simulate different levels of cyanosis of the patient simulator 1102. In that regard, the degree of cyanosis is determined by the control system 1104 and/or a user of the control system 1104 in some embodiments. The degree of cyanosis may trend—increase and/or decrease—based on a variety of parameters including the efficacy of any treatments administered. In some embodiments, the trending is controlled manually via the control system 1104. In other embodiments, the trending is at least partially controlled by a physiological simulator software application of the control system 1104.

The patient simulator 1102 also includes an intubation module 1194. The intubation module 1194 is configured to monitor intubation of the patient simulator 1102. In that regard, the depth of proper intubation for the patient simulator 1102 will depend on the size and/or age of the patient simulator. In that regard, the intubation module 1194 is associated with a particular size of patient simulator to determine the proper intubation depth. In some embodiments, the intubation module 1194 utilizes an optical sensor to monitor the depth of an intubation tube within the trachea of the patient simulator 1102. In some embodiments, the intubation module 1194 utilizes a pair of optical sensors spaced apart from one another to define the acceptable range of intubation depths. The first optical sensor is utilized to detect the presence of an intubation tube as it reaches the beginning of the acceptable range of depths. The second optical sensor is utilized to detect when the intubation tube has been advanced beyond the acceptable range of depths. In some embodiments, the patient simulator 1102 also includes a reverse breathing valve module 1196 and a bypass breathing valve module 1198.

The patient simulator 1102 also includes a right arm motion module 1200 and a left arm motion module 1202. The right and left arm motion modules 1200 and 1202 are configured to activate movement of the left and right arms of the simulator 1102. In some embodiments, the right and left arm modules 1200 and 1202 are particularly suited for use in a newborn sized simulator. In some embodiments, the right and left arm motion modules 1200 and 1202 comprise pneumatic modules that are utilized to inflate and deflate air bags associated with the arms of the simulator. In that regard, in some instances the air bags comprise accordion bags such that as the bags are filled with air they expand outwardly in a predetermined profile. By inflating and deflating the bags with the modules, the arms of the simulator are moved. The bags are associated with a pivot assembly positioned adjacent the simulator's elbow in some instances. In one particular embodiment, inflation and deflation of the bags causes the simulator's arm to bend or straighten via the pivot assembly. As movement of the arms is actuated by a pneumatic module and the inflation and deflation of air bags, a user can restrain movement of the arms without causing physical damage to the simulator in contrast to some mechanically actuated systems. In some embodiments, the arm motion modules are configured to activate a mechanical system or motor for moving the simulator's arms. In some embodiments, the mechanical system includes a safety to prevent damage to the arm motion modules and associated components if and when the intended arm motion is restricted by a user.

In some embodiments, the patient simulator 1102 includes left and right leg motion modules that operate in a similar manner to the arm motion modules. In that regard, the right and left leg motion modules are configured to activate movement of the left and right legs of the simulator 1102. In some embodiments, the right and left leg modules are particularly suited for use in a newborn sized simulator. In some embodiments, the right and left leg motion modules comprise pneumatic modules that are utilized to inflate and deflate air bags associated with the legs of the simulator. In that regard, in some instances the air bags comprise accordion bags such that as the bags are filled with air they expand outwardly to a predetermined profile. By inflating and deflating the bags with the modules, the legs of the simulator are moved. The bags are associated with a pivot assembly positioned adjacent the simulator's knee in some instances. In one particular embodiment, inflation and deflation of the bags causes the simulator's leg to bend or straighten via the pivot assembly. As movement of the legs is actuated by a pneumatic module and the inflation and deflation of air bags, a user can restrain movement of the legs without causing physical damage to the simulator, in contrast to some mechanically actuated systems. In some embodiments, the leg motion modules are configured to activate a mechanical system or motor for moving the simulator's legs. In some embodiments, the mechanical system includes a safety to prevent damage to the leg motion modules and associated components if and when the intended leg motion is restricted by a user.

The patient simulator 1102 also includes a rotation module 1204. The rotation module 1204 is configured to rotate the fetus or baby within the mother simulator. Particularly, the rotation module 1204 is configured to actuate a motor or other device for controlling the rotation of the baby as it travels within the birth canal of the mother simulator. The patient simulator 1102 also includes a load cell module 1206. In some embodiments, the load cell module is positioned on a delivery mechanism of the mother simulator and is configured to monitor the amount of pressure being exerted on the baby during birthing. In that regard, the load cell module is positioned adjacent the attachment point of the baby to the delivery mechanism in some embodiments. In other embodiments, the load cell module is positioned within or on the baby itself. Generally, the signals generated by the load cell are communicated to the control system 1104 via the master module 1106. Based on the sensed pressures or forces on the load cell, a determination can be made regarding whether the amount of force being used in removing the baby from the birth canal is within a desired range.

The patient simulator 1102 also includes a tummy pressure module 1208. The tummy pressure module 1208 is utilized to control the firmness of the mother simulator's tummy. In that regard, the tummy pressure module 1208 is configured to sense the amount of pressure within the mother's tummy. Based on a desired pressure, the tummy pressure module 1208 determines whether pressure in the tummy should be increased, decreased, or remain the same. If the pressure should be increased, then the tummy pressure module 1208 activates the flow of air to the tummy through a pneumatic valve. In some embodiments, the tummy pressure module 1208 is in communication with an air reservoir or compressor for providing the air flow to the tummy. If the pressure should be decreased, then the tummy pressure module 1208 activates the release of air from the tummy. The desired pressure is provided by the control system 1104 in some instances. In that regard, a user or teacher can define the tummy pressure via the control system 1104 in some embodiments.

The patient simulator 1102 also includes a baby release module 1210. The baby release module 1210 is configured to selectively release the baby from the delivery mechanism within the maternal simulator. In that regard, the baby release module 1210 is remotely activated by a user or teacher via the control system 1104 in some instances. In other instances, the baby release module 1210 is activated based on the position of the delivery mechanism and/or baby within the birth canal. That is, once the baby reaches a certain position and/or orientation with the birth canal the baby release module activates to release the engagement between the delivery mechanism and the baby.

The patient simulator 1102 also includes a tongue control module 1212. The tongue control module 1212 is a pneumatic module configured to selectively inflate and/or deflate the tongue to partially obstruct an airway of the simulator 1102. In that regard, the tongue control module 1212 is controlled via the control system 1104 in some instances. Accordingly, a user or teacher can partially block or unblock the airway as desired. The patient simulator 1102 also includes a larynges control module 1214 and a pharynges control module 1216. The larynges control module 1214 is configured to open and close the larynx to partially obstruct the airway of the simulator. Similarly, the pharynges control module 1216 is configured to urge the posterior wall of the pharynx anteriorly to partially obstruct the airway of the simulator. The larynges control module 1214 and the pharynges control module 1216 are also controlled via the control system 1104 in some instances. Accordingly, a user or teacher can also partially block or unblock the airway as desired with these features as well.

The patient simulator 1102 also includes a pneumothorax module 1218 and a pneumothorax release module 1220. The pneumothorax module 1218 is configured to simulate the presence of a pneumothorax (collapsed lung) in the left lung or the right lung. The pneumothorax release module 1220 is configured to return the simulator 1102 to normal lung condition without a pneumothorax. The onset and alleviation of the pneumothorax condition is controlled via the control system 1104.

The patient simulator 1102 also includes eye module 1222. The eye module 1222 is configured to control the patient's simulated eyes including blinking and pupil dilation. The eye module 1222 includes a plurality of modules for controlling these functions in some embodiments. For example, see FIGS. 46-49 and accompanying description for one such embodiment. In some embodiments, the pupil dilation of each of the simulator's eyes is controlled at least partially based on the amount of light received by an optical sensor positioned within the eye. The maximum size of the pupil and/or the rate of change or dilation of the pupil are controlled by the control system 1104 in some instances. Similarly, the rate, pattern, and speed of blinking are controlled by the control system 1104 in some instances. In some instances the rate of blinking ranges from 5 blinks per minute to 30 blinks per minute. However, ranges outside of this are used in some embodiments. Further, the eyes can be maintained in an open position or a closed position. The speed of the blinks can be controlled as well. In some instances, the speed of each blink from open to closed to open is approximately 200 ms. However, the speed of the blinks can be increased or decreased as desired in some embodiments.

The patient simulator 1102 also includes a right side seizure module 1224 and a left side seizure module 1226. The right and left seizure modules 1224 and 1226 are configured to simulate a seizure of the patient on the corresponding sides of the patient's body. Accordingly, the seizure modules 1224 and 1226 are configured to cause shaking and/or convulsing in some embodiments. Also, the seizure modules 1224 and 1226 are used together in some instances to simulate a full body seizure. In some instances activation of the seizure modules 1224 and 1226 is controlled via the control system 1104.

The patient simulator 1102 also includes a rotational module 1228 and a positional module 1230. The rotational module 1228 and the positional module 1230 are configured to provide positional data regarding the baby within the birthing canal of a maternal simulator. In that regard, the rotational module 1228 and positional module 1230 are particularly configured to monitor the relative rotation of the baby within the birth canal. In some embodiments, the rotational module 1228 is positioned on the delivery mechanism of the maternal simulator and the positional module 1230 is positioned within a portion of the baby. In some instances, the positional module 1230 is positioned within the head of the baby. The rotation of the baby is determined by comparing the relative rotation of the positional module 1230 on the baby to the rotational module 1228. In some instances, the rotational module 1230 is substantially fixed rotationally. Based on the relative rotation of the module 1230 compared to the module 1228 the rotational position of the baby can be determined. The rotational data from the modules 1228 and 1230 is communicated to the control system 1104 in some embodiments. In one such embodiment, a user or teacher utilizes the positional and rotational information to determine when to release the baby from the delivery mechanism of the maternal simulator. In other embodiments, the control system 1104 automatically releases the baby from the delivery mechanism based on a correct orientation and position of the baby within the birth canal. The patient simulator 1102 also includes a pneumatic module 1232. The pneumatic module 1232 is configured to control a pneumatically actuated portion of the simulator 1102.

Each of the various modules is connected to the master module 1106 via a power wire 1234, a ground wire 1236, and a 2-way communication wire 1238. In that regard, the master module 1106 can control the activation, deactivation, and power consumption of each of the modules. In some embodiments, the master module 1106 is controlled via a software program of the control system 1104. In other embodiments, the modules are directly connected to a power supply. In some embodiments, the master module 1106 is in wireless communication with one or more of the modules. In some embodiments, communication to one or more of the modules is 1-way communication. In some embodiments, the modules themselves are interconnected via the communication wire 1238 or an additional communication wire. In that regard, in some instances a non-master module acts as a master module for a subset of modules.

Figure 30:
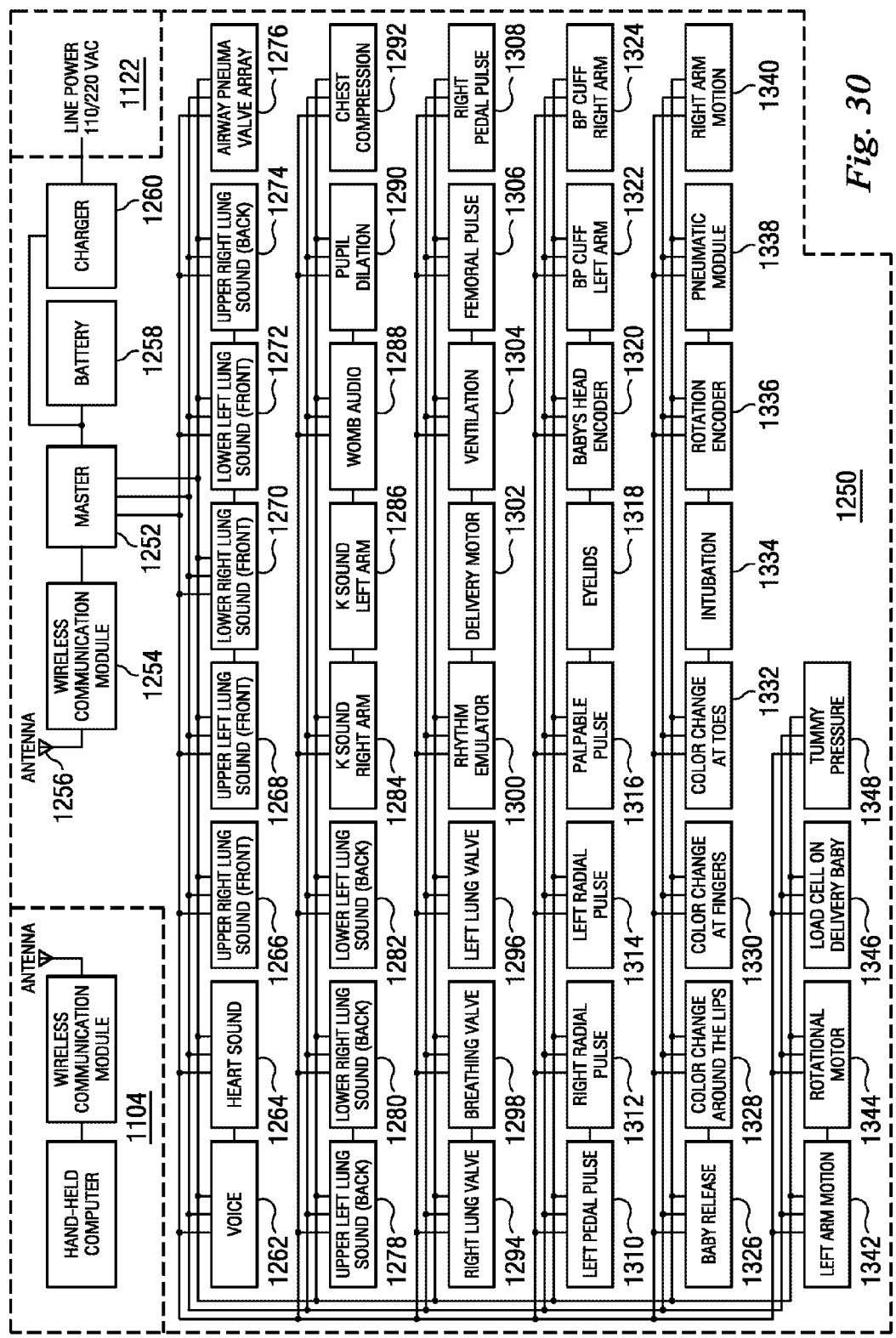
FIG. 30 is a diagrammatic schematic view of a patient simulator system according to another embodiment of the present disclosure.

Referring now to FIG. 30, shown therein is a diagrammatic schematic view of a patient simulator 1250 according to one embodiment of the present disclosure incorporating aspects of the patient simulator system 1100 described above. For example, the patient simulator 1250 is in communication with a control system 1104 and a power source 1122.

The patient simulator 1250 is particularly suited for simulating a birthing sequence. In that regard, the patient simulator 1250 includes a maternal simulator in some embodiments. In some embodiments, the patient simulator 1250 has a fetal simulator associated therewith for performing simulated deliveries. The patient simulator 1250 includes a plurality of modules for performing the various functions of the simulator. In some embodiments, each of the modules controls a particular function or group of functions of the simulator 1250. In that regard, the modules are appropriately sized for positioning within various portions of the simulator 1250. In some embodiments, the modules are positioned throughout the simulator adjacent to the region or area of the simulator 1250 related to the module's specific function or the associated body part of the simulator. Accordingly, the modules are distributed throughout the simulator rather than being grouped onto a single motherboard. In some embodiments, each of the modules is in communication with a master module 1252. In some embodiments the master module 1252 is configured to provide and control the power delivered to the modules and facilitate communication with and among the modules.

In the current embodiment, the patient simulator 1250 is shown in wireless communication with the control system 1104. In that regard, the patient simulator 1250 includes a wireless communication module 1254 and an antenna 1256 similar to those described above with respect to FIG. 29. The patient simulator 1250 also includes a power supply 1258. In the present embodiment, the power supply 1258 is a rechargeable battery. In that regard, the power supply 1258 is connected to a charger 1260. The charger 1260 is configured to recharge the power supply 1258. In that regard, the charger 1260 is configured for communication with an external power supply 1122. In the current embodiment, the external power supply 1122 is a wall outlet or standard line power supply. In other embodiments, the external power supply 1122 is configured for wireless communication with the charger 1260 or power supply 1258 such that the power supply may be recharged wirelessly, such as by inductive coupling or other wireless charging means. In some embodiments, the charger 1260 comprises a backup power supply.

The patient simulator 1250 includes a voice module 1262. The voice module 1262 is in communication with the master module 1252, which is in communication with the control system 1104. The voice module 1262 is an audio module configured to emit sounds simulating a patient's voice. In that regard, the particular sounds emitted by the voice module 1262 are controlled in some embodiments by a user through the control system 1104. In some embodiments, the control system 1104 includes a plurality of stored or prerecorded sounds that may be selected from and played back by the voice module 1262 as discussed above in greater detail with respect to FIG. 29. In some embodiments, the control system 1104 is in communication with the voice module 1262 such that a user or teacher speaks into a microphone or other sound communication device associated with the control system and the teacher's words or sounds are emitted from the voice module 1262. In some embodiments, the user or teacher's input may be conditioned using audio amplifiers or sound boards to alter the sound of the voice emitted from the voice module 1262. For example, in some embodiments the input sound is conditioned to simulate a hoarse patient, a patient with a blocked air passage, or other mental or physical medical condition of the patient. In that regard, the teacher may selectively activate various types of audio conditioning based on a desired effect. The voice module 1262 and the corresponding voice simulation are utilized as part of an overall medical scenario simulation in some embodiments.

The patient simulator 1250 also includes a heart sound module 1264. The heart sound module 1264 is an audio module configured to emit sounds to simulate the natural sounds of a patient's heart. In that regard, the sounds of the heart sound module 1264 include one or more of sounds to simulate the patient's heart rate and cardiac rhythm (e.g., sinus, atrial tachycardia, multifocal atrial tachycardia, atrial flutter, atrial fibrillation, junctional, idioventricular, ventricular tachycardia (uni.), ventricular tachycardia (multi.), supraventricular tachycardia, ventricular flutter, ventricular fibrillation, agonal, asystole, LBBB, RBBB, $1^{st}$ degree AVB, $2^{nd}$ degree AVB (Type I), $2^{nd}$ degree AVB (Type II), $3^{rd}$ degree AVB, Q-wave infarction, ST segment elevation, ST segment depression, T-wave inversion, atrial paced, AV sequential paced, vent. Pacemaker (artificial), and/or other cardiac rhythms). Further, the heart sounds may be normal, distant, non-existent, include a systolic murmur, S3, and/or S4. The control system 1104 and/or a user utilizing the control system determines what heart sounds and at what rate the sounds are produced in some embodiments. The sounds produced by the heart sound module 1264 are detectable via use of a stethoscope in some instances. In some embodiments, at least a portion of the heart sound module 1264—such as a speaker—is positioned within the simulator 1250 where the natural heart would be.

The patient simulator 1250 also includes lung sound modules 1266, 1268, 1270, 1272, 1274, 1278, 1280, and 1282. In particular, lung sound module 1266 is utilized to simulate sounds of the upper right lung towards the front of the simulator 1250; lung sound module 1268 is utilized to simulate sounds of the upper left lung towards the front of the simulator; lung sound module 1270 is utilized to simulate sounds of the lower right lung towards the front of the simulator; lung sound module 1272 is utilized to simulate sounds of the lower left lung towards the front of the simulator; lung sound module 1274 is utilized to simulate sounds of the upper right lung towards the back of the simulator; lung sound module 1278 is utilized to simulate sounds of the upper left lung towards the back of the simulator; lung sound module 1280 is utilized to simulate sounds of the lower right lung towards the back of the simulator; lung sound module 1282 is utilized to simulate sounds of the lower left lung towards the front of the simulator.

Each of the lung sound modules 1266, 1268, 1270, 1272, 1274, 1278, 1280, and 1282 is an audio module configured to produce sounds to simulate the natural sounds of a patient's lungs. In that regard, the lung sound modules 1266, 1268, 1270, 1272, 1274, 1278, 1280, and 1282 are configured to produce one or more of the following lung sounds in some embodiments: normal, none, wheezing, inspiration squeaks, crackles, rails, and/or other lung sounds. Further, the combination of lung sound modules 1266, 1268, 1270, 1272, 1274, 1278, 1280, and 1282 are utilized to simulate respiratory patterns including, but not limited to normal, Kussmaul's, Cheyne-Stokes, Biot's, apneusic, and/or other respiratory patterns. The combination of lung sound modules 1266, 1268, 1270, 1272, 1274, 1278, 1280, and 1282 are also utilized to simulate the respiratory rate of the patient. In that regard, the respiratory rate may be set at a constant rate and/or be set to change over time.

The patient simulator 1250 also includes a valve array module 1276. The valve array module includes a plurality of pneumatic valves and is configured to control aspects of the breathing system. In some embodiments, the valve array module 1276 is configured to control the simulation of a pneumothorax condition in the left or right lung of the simulator 1250.

The patient simulator 1250 also includes a K-sound module 1284 for the right arm of the simulator and a K-sound module 1286 for the left arm of the simulator. Each of the K-sound modules 1284 and 1286 are configured to produce a simulated K-sound (Korotkoff sound). In that regard, the K-sound modules 1284 and 1286 are utilized to allow a user to take the blood pressure of the patient simulator 1250 in some embodiments. Accordingly, the K-sounds produced by the modules 1284 and 1286 are determined based on a simulated heart rate and blood pressure. In some instances, the heart rate and blood pressure of the patient simulator 1250 are provided by a user or teacher via the control system 1104.

The patient simulator 1250 also includes a womb audio module 1288 to simulate the sounds of the fetus within the womb of the mother. In some embodiments the womb audio module 1148 is configured to simulate the heart beat of the fetus within the womb. The patient simulator also includes a pupil dilation module 1290. The pupil dilation module 1290 is configured to control the dilation of the pupils of the simulator's eyes. In some embodiments, the pupil dilation of each of the simulator's eyes is controlled at least partially based on the amount of light received by an optical sensor positioned within the eye. Further, the maximum size of the pupil and/or the rate of change or dilation of the pupil are controlled by the control system 1104 in some instances. In some instances the parameters of the pupil dilation are selected to simulate a specific medical condition.

The patient simulator 1250 also includes a compression module 1292. The compression module 1292 is configured to monitor the force of chest compressions applied to the simulator 1250. In that regard, the compression module 1292 is configured to monitor the pressure applied and based on that pressure determine whether the pressure is too high, too low, or within the desired range. The compression module 1292 is in communication with the master module 1252, such that the determination of whether the correct pressure is being applied is relayed to the control system 1104. In some embodiments, the simulator 1250 will trend towards recovery or further complications based on whether the correct pressure is applied. For example, if the chest compressions are within the desired range of pressures then the patient simulator may show signs of recovery. On the other hand, if the chest compressions are outside the desired range of pressures then the patient simulator may develop additional problems or symptoms and/or make it more difficult to recover the simulator from the present symptoms.

The patient simulator 1250 also includes a right lung valve 1294, a left lung valve 1296, and a breathing valve 1298. Together the right lung valve 1294, the left lung valve 1296, and the breathing valve 1298 control the flow of air into and out of the lungs of the simulator 1250. In that regard, each of the valves 1294, 1296, and 1298 comprise a pneumatic valve. In some embodiments, the breathing valve 1298 is utilized to control the respiratory rate of the simulator 1250. In that regard, the breathing valve 1298 opens and closes in order for the lungs to inflate and deflate at the desired rate. The right lung valve 1294 and the left lung valve 1296 are utilized to selectively disable the right and/or left lungs, respectively. Accordingly, in some embodiments when the right lung valve 1294 is opened it closes a 3-way air pilot valve such that air cannot flow from the breathing valve into the right lung. In such instances, air flows from the breathing valve solely into the left lung. The left lung valve 1296 operates in a similar manner in some embodiments. Factors such as disablement of the lungs, respiratory rate, respiratory pattern, inspiratory rate, and/or disablement of the left or right lung are controlled by the valves 1294, 1296, and 1298 based on signals received from the control system 1104 via the master module 1252.

The patient simulator 1250 also includes an ECG module 1300 or rhythm emulator. The ECG module is configured to emit an electrical signal that simulates the electrical activity of the heart of the simulator 1250. In some embodiments, the ECG modules are configured to provide signals associated with each of the 12 leads such that a 12-lead ECG signal is available to the user. In some embodiments, the ECG module 1300 is configured to emit signals that simulate the presence of a myocardial infarction in various parts of the heart. In some embodiments, the position of the myocardial infarction is selected via the control system 1104. Accordingly, the ECG module is utilized to train users to identify the onset of heart attacks and/or the associated symptoms identifiable via an ECG. The electrical signal of the ECG module is detectable by standard ECG equipment.

The patient simulator 1250 also includes a delivery motor module 1302. The delivery motor module 1302 is utilized to control the delivery of the fetus or baby from the simulator 1250. In that regard, the delivery motor module 1302 is utilized to control the position of the baby within the mother simulator. Upon activation by the delivery motor module 1302, the delivery mechanism urges the baby out of the mother's womb. In some embodiments, the delivery mechanism will deliver the baby at least partially out of the mother's womb where the user completes delivery of the baby. In some embodiments, the delivery mechanism rotates the baby as it travels down the birth canal.

The patient simulator 1250 also includes a ventilation module 1304. The ventilation module 1304 is configured to monitor the use of a ventilation device applied to the simulator 1250. The ventilation device is a bag-valve mask in some instances. In other instances, the ventilation device is a user's mouth, such as in mouth-to-mouth resuscitation. The ventilation module 1304 is configured to monitor the pressure applied by the ventilation device and based on that pressure determine whether the pressure is too high, too low, or within the desired range. The ventilation module 1304 is in communication with the master module 1252, such that the determination of whether the correct pressure is being applied is relayed to the control system 1104. In some embodiments, the simulator 1250 will trend towards recovery or further complications based on whether the correct pressure is applied. For example, if the ventilation is within the desired range of pressures then the patient simulator may show signs of recovery. On the other hand, if the ventilation is outside the desired range of pressures then the patient simulator may develop additional problems or symptoms and/or make it more difficult to recover the simulator from the present symptoms.

The patient simulator 1250 also includes a femoral pulse module 1306. The femoral pulse module 1306 is a pneumatic module for simulating the femoral pulse of the simulator 1250. The patient simulator 1250 also includes a right pedal pulse module 1308 and a left pedal pulse module 1310. The left and right pedal pulse modules 1308, 1310 are configured to simulate the pedal pulses of the simulator 1250. In that regard, in some embodiments the pedal pulse modules 1308, 1310 are electrical modules configured to simulate the pedal pulses. In other embodiments, the pedal pulse modules 1308, 1310 are pneumatic modules configured to simulate the pedal pulses. The patient simulator 1250 also includes a right radial pulse module 1312 and a left radial pulse module 1314. The right and left radial pulse modules 1312, 1314 are pneumatic modules for simulating the radial pulses of the simulator 1250. The patient simulator 1250 also includes a palpable pulse module 1316.

The patient simulator 1250 also includes eyelid module 1318. The eyelid module 1318 is configured to control the blinking of the patient's simulated eyes. The rate, pattern, and speed of blinking are controlled by the control system 1104 in some instances. In some instances the rate of blinking ranges from 5 blinks per minute to 30 blinks per minute. In other embodiments, ranges outside of this are used. Further, the eyes can be maintained in an open position or a closed position. The speed of the blinks can be controlled as well. In some instances, the elapsed time or speed of each blink from open to closed to open is approximately 200 ms. However, the speed of the blinks can be increased or decreased as desired in some embodiments.

The patient simulator 1250 also includes an encoder module 1320 and an encoder module 1336. The encoder modules 1320 and 1336 are configured to provide positional data regarding the baby within the birthing canal of a maternal simulator. In that regard, the encoder modules 1320 and 1336 are configured to monitor the relative rotation of the baby within the birth canal in some instances. In some embodiments, the encoder module 1336 is positioned on the delivery mechanism of the maternal simulator and the encoder module 1320 is positioned within a portion of the baby or fetal simulator. In some instances, the encoder module 1320 is positioned within the head of the baby. The rotation of the baby is determined by comparing the relative rotation of the encoder module 1320 on the baby to the encoder module 1336. In some instances, the module 1336 is substantially fixed rotationally. Based on the relative rotation of the module 1320 compared to the module 1336 the rotational position of the baby can be determined. In some embodiments, the modules 1320 and 1336 are optical devices. The rotational data from the modules 1320 and 1336 is communicated to the control system 1104 in some embodiments. In one such embodiment, a user or teacher utilizes the positional and rotational information to determine when to release the baby from the delivery mechanism of the maternal simulator. In other embodiments, the control system 1104 automatically releases the baby from the delivery mechanism based on a correct orientation and position of the baby within the birth canal.

The patient simulator 1250 also includes a left blood pressure cuff module 1322 and a right blood pressure cuff module 1324. The left and right blood pressure cuff modules 1322 and 1324 are pressure modules configured to allow a user to take a simulated blood pressure of the patient simulator 1250. The blood pressure cuff modules 1322 and 1324 are configured for use with standard blood pressure monitors in some embodiments.

The patient simulator 1250 also includes a baby release module 1326. The baby release module 1326 is configured to selectively release the baby from the delivery mechanism within the maternal simulator. In that regard, the baby release module 1326 is remotely activated by a user or teacher via the control system 1104 in some instances. In other instances, the baby release module 1326 is activated based on the position of the delivery mechanism and/or baby within the birth canal. That is, once the baby reaches a certain position and/or orientation with the birth canal the baby release module activates to release the engagement between the delivery mechanism and the baby.

The patient simulator 1250 also includes a plurality of color change modules 1328, 1330, and 1332. In that regard, the color change module 1328 is configured for controlling color change around the lips of the simulator 1250; the color change module 1330 is configured for controlling color change around the fingers of the simulator; and the color change module 1332 is configured for controlling color change around the toes of the simulator. The color change modules 1328, 1330, and 1332 are utilized in some embodiments to simulate cyanosis of the patient simulator. Accordingly, the color change modules 1328, 1330, and 1332 are configured to simulate different levels of cyanosis of the patient simulator 1250. In that regard, the degree of cyanosis is determined by the control system 1104 and/or a user of the control system 1104 in some embodiments. The degree of cyanosis may trend—increase and/or decrease—based on a variety of parameters including the efficacy of any treatments administered. In some embodiments, the trending is controlled manually via the control system 1104. In other embodiments, the trending is at least partially controlled by a physiological simulator software application of the control system 1104.

The patient simulator 1250 also includes an intubation module 1334. The intubation module 1334 is configured to monitor intubation of the patient simulator 1250. In that regard, the depth of proper intubation for the patient simulator 1250 will depend on the size and/or age of the patient simulator. In that regard, the intubation module 1334 is associated with a particular size of patient simulator to determine the proper intubation depth. In some embodiments, the intubation module 1334 utilizes an optical sensor to monitor the depth of an intubation tube within the trachea of the patient simulator 1250. In some embodiments, the intubation module 1334 utilizes a pair of optical sensors spaced apart from one another to define the acceptable range of intubation depths. The first optical sensor is utilized to detect the presence of an intubation tube as it reaches the beginning of the acceptable range of depths. The second optical sensor is utilized to detect when the intubation tube has been advanced beyond the acceptable range of depths. In some embodiments, the patient simulator 1250 also includes a pneumatic module 1338 for controlling a pneumatic device of the simulator.

The patient simulator 1250 also includes a right arm motion module 1340 and a left arm motion module 1342. The right and left arm motion modules 1340 and 1342 are configured to activate movement of the left and right arms of the simulator 1250. In some embodiments, the right and left arm modules 1340 and 1342 are used in the fetal simulator. In other embodiments, the right and left arm modules 1340 and 1342 are used in both the maternal simulator and the fetal simulator. In some embodiments, the right and left arm motion modules 1340 and 1342 comprise pneumatic modules that are utilized to inflate and deflate air bags associated with the arms of the simulator. In that regard, in some instances the air bags comprise accordion bags such that as the bags are filled with air they expand outwardly in a predetermined profile. By inflating and deflating the bags with the modules, the arms of the simulator are moved. The bags are associated with a pivot assembly positioned adjacent the simulator's elbow in some instances. In one particular embodiment, inflation and deflation of the bags causes the simulator's arm to bend or straighten via the pivot assembly. As movement of the arms is actuated by a pneumatic module and the inflation and deflation of air bags, a user can restrain movement of the arms without causing physical damage to the simulator in contrast to some mechanically actuated systems. In some embodiments, the arm motion modules are configured to activate a mechanical system or motor for moving the simulator's arms. In some embodiments, the mechanical system includes a safety to prevent damage to the arm motion modules and associated components if and when the intended arm motion is restricted by a user.

The patient simulator 1250 also includes a rotation module 1344. The rotation module 1344 is configured to rotate the fetus or baby within the mother simulator. Particularly, the rotation module 1344 is configured to actuate a motor or other device for controlling the rotation of the baby as it travels within the birth canal of the mother simulator. The patient simulator 1250 also includes a load cell module 1346. In some embodiments, the load cell module is positioned on a delivery mechanism of the mother simulator and is configured to monitor the amount of pressure being exerted on the baby during birthing. In that regard, the load cell module is positioned adjacent the attachment point of the baby to the delivery mechanism in some embodiments. In other embodiments, the load cell module is positioned within or on the baby itself. Generally, the signals generated by the load cell are communicated to the control system 1104 via the master module 1252. Based on the sensed pressures or forces on the load cell, a determination can be made regarding whether the amount of force being used in removing the baby from the birth canal is within a desired range.

Finally, the patient simulator 1250 also includes a tummy pressure module 1348. The tummy pressure module 1348 is utilized to control the firmness of the mother simulator's tummy. In that regard, the tummy pressure module 1348 is configured to sense the amount of pressure within the mother's tummy. Based on a desired pressure, the tummy pressure module 1348 determines whether pressure in the tummy should be increased, decreased, or remain the same. If the pressure should be increased, then the tummy pressure module 1348 activates the flow of air to the tummy through a pneumatic valve. In some embodiments, the tummy pressure module 1348 is in communication with an air reservoir or compressor for providing the air flow to the tummy. If the pressure should be decreased, then the tummy pressure module 1348 activates the release of air from the tummy. The desired pressure is provided by the control system 1104 in some instances. In that regard, a user or teacher can define the tummy pressure via the control system 1104 in some embodiments.

Each of the various modules of the simulator 1250 is connected to the master module 1252 via a power wire, a ground wire, and/or a 2-way communication wire. Accordingly, the master module 1252 is utilized to control the activation, deactivation, and power consumption of the modules in some embodiments. In some embodiments, the master module 1252 is controlled or directed via a software program of the control system 1104. In some embodiments, the master module 1252 is in wireless communication with one or more of the modules. In some embodiments, the modules themselves are interconnected via the communication wire or an additional communication wire. In that regard, in some instances a non-master module acts as a master module for a subset of modules.

In some embodiments, the patient simulator 1250 also includes a compressor. The compressor is utilized to provide a compressed air supply to the various pneumatic devices and modules of the simulator 1250. For example, in some embodiments the compressor is utilized to provide air to modules for simulating the lungs, pulses, contractions, tummy pressure, seizures, eye dilation, blinking, and/or other aspects of the patient simulator 1250. In some embodiments, the compressor provides pressurized air to one or more air reservoirs or accumulators that are then connected to the various pneumatic modules of the simulator 1250. In that regard, the air reservoirs may maintain different air pressures such that different pneumatic modules are connected to the air reservoir with the appropriate air pressure for its application. In some instances, the pneumatic modules of the patient simulator 1250 that utilize the compressor are configured to run at a relatively low air pressure, e.g., less than 10 psi in some embodiments and less than 5 psi in other embodiments. In some instances, the simulator 1250 includes two accumulators with one of the accumulators maintaining an air pressure of approximately 5 psi and the other accumulator maintaining an air pressure of approximately 1 psi. In other embodiments, the accumulators maintain other air pressures. Generally, however, the patient simulator 1250 and its associated components are configured to operate at low pressures, which helps prevent the introduction of water into the simulator associated with high pressure systems. The introduction of water into the simulator that results from using high pressure systems can cause damage to the simulator, increase the maintenance costs, and require additional components to remove or limit the amount of water within the simulator.

Further, the compressor is sized to fit entirely within the simulator 1250 in some embodiments. In that regard, the compressor operates quietly so as not to interfere with the other simulation aspects of the simulator 1250 and, in particular, the audible simulation aspects. Accordingly, in some instances a muffler system is utilized to minimize the noise generated by the compressor. The muffler system is utilized on the input, output, and/or both sides of the compressor in some embodiments. Further, the compressor is self-cooling in some instances. In one such embodiment, the compressor includes a plurality of metal pipes surrounding at least the compressor motor that intake air is passed through. The intake air passing through the metal pipes helps to dissipate the heat generated by the compressor. Accordingly, the compressor is able to operate entirely within the simulator 1250 without overheating or disturbing the other simulation aspects of the simulator. This allows the simulator 1250 to be fully functional without attachment to a noisy, external, high pressure compressor.

Figure 31:
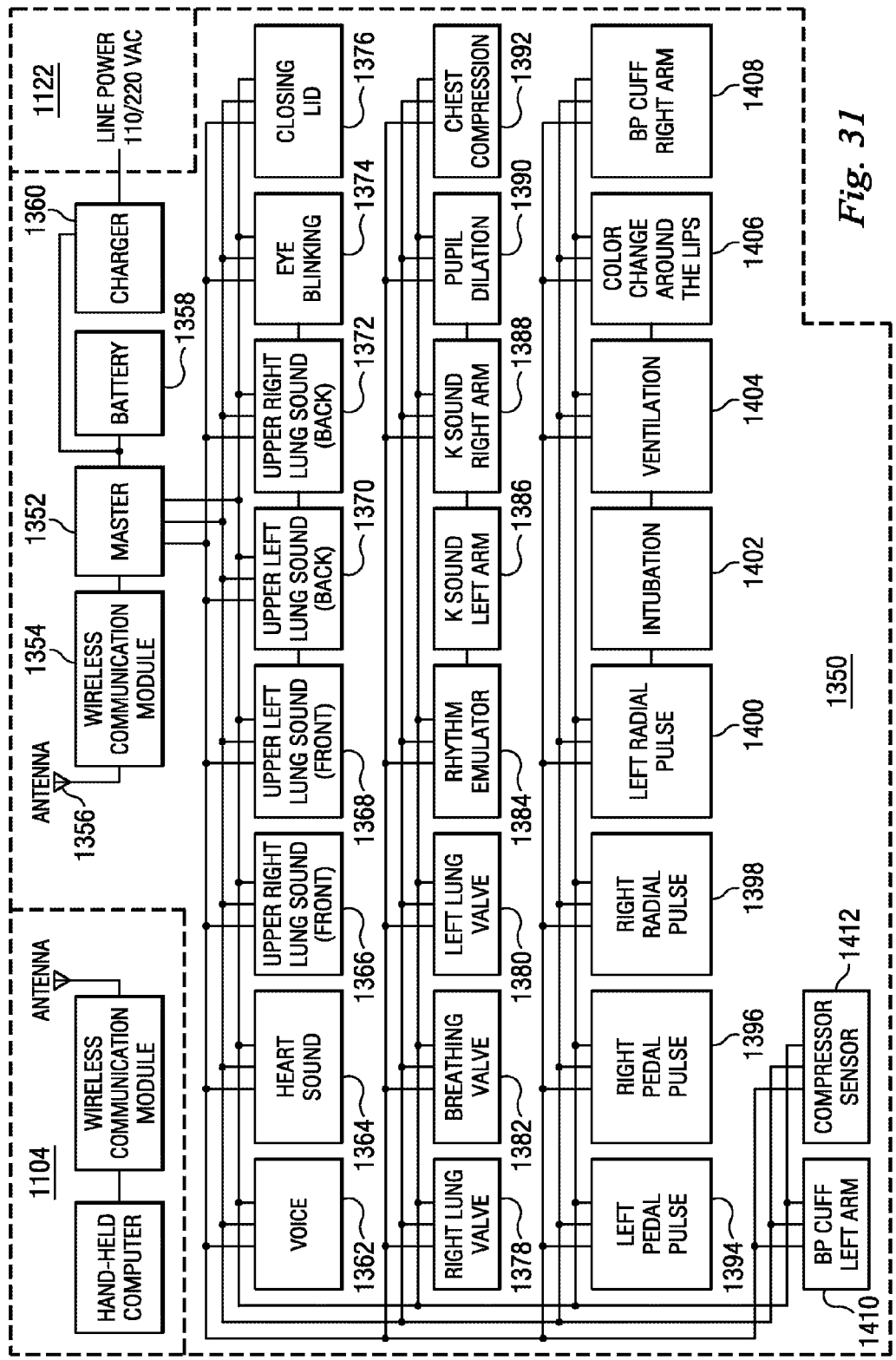
FIG. 31 is a diagrammatic schematic view of a patient simulator system according to another embodiment of the present disclosure.

Referring now to FIG. 31, shown therein is a diagrammatic schematic view of a patient simulator 1350 according to another embodiment of the present disclosure incorporating aspects of the patient simulator system 1100 described above. For example, the patient simulator 1350 is in communication with a control system 1104 and a power source 1122. The patient simulator 1350 is approximately the size of a five-year old in some embodiments. The patient simulator 1350 includes a plurality of modules for performing the various functions of the simulator. In some embodiments, each of the modules controls a particular function or group of functions of the simulator 1350. In that regard, the modules are appropriately sized for positioning within various portions of the simulator 1350. In some embodiments, the modules are positioned throughout the simulator adjacent to the region or area of the simulator 1350 related to the module's specific function or the associated body part of the simulator. Accordingly, the modules are distributed throughout the simulator rather than being grouped onto a single motherboard. In some embodiments, each of the modules is in communication with a master module 1352. In some embodiments the master module 1352 is configured to provide and control the power delivered to the modules and facilitate communication with and among the modules.

In the current embodiment, the patient simulator 1350 is shown in wireless communication with the control system 1104. In that regard, the patient simulator 1350 includes a wireless communication module 1354 and an antenna 1356 similar to those described above with respect to FIGS. 29 and 30. The patient simulator 1350 also includes a power supply 1358. In the present embodiment, the power supply 1238 is a rechargeable battery. In that regard, the power supply 1358 is connected to a charger 1360. The charger 1360 is configured to recharge the power supply 1358. In that regard, the charger 1360 is configured for communication with an external power supply 1122. In the current embodiment, the external power supply 1122 is a wall outlet or standard line power supply. In other embodiments, the external power supply 1122 is configured for wireless communication with the charger 1360 or power supply 1358 such that the power supply may be recharged wirelessly, such as by inductive coupling or other wireless charging means. In some embodiments, the charger 1360 comprises a backup power supply.

The patient simulator 1350 includes a voice module 1362. The voice module 1362 is in communication with the master module 1352, which is in communication with the control system 1104. The voice module 1362 is an audio module configured to emit sounds simulating a patient's voice. In that regard, the particular sounds emitted by the voice module 1362 are controlled in some embodiments by a user through the control system 1104. In some embodiments, the control system 1104 includes a plurality of stored or prerecorded sounds that may be selected from and played back by the voice module 1362 as discussed above in greater detail with respect to FIG. 29. In some embodiments, the control system 1104 is in communication with the voice module 1362 such that a user or teacher speaks into a microphone or other sound communication device associated with the control system and the teacher's words or sounds are emitted from the voice module 1362. In some embodiments, the user or teacher's input may be conditioned using audio amplifiers or sound boards to alter the sound of the voice emitted from the voice module 1362. For example, in some embodiments the input sound is conditioned to simulate a hoarse patient, a patient with a blocked air passage, or other mental or physical medical condition of the patient. In that regard, the teacher may selectively activate various types of audio conditioning based on a desired effect. The voice module 1362 and the corresponding voice simulation are utilized as part of an overall medical scenario simulation in some embodiments.

The patient simulator 1350 also includes a heart sound module 1364. The heart sound module 1364 is an audio module configured to emit sounds to simulate the natural sounds of a patient's heart. In that regard, the sounds of the heart sound module 1364 include one or more of sounds to simulate the patient's heart rate and cardiac rhythm (e.g., sinus, atrial tachycardia, multifocal atrial tachycardia, atrial flutter, atrial fibrillation, junctional, idioventricular, ventricular tachycardia (uni.), ventricular tachycardia (multi.), supraventricular tachycardia, ventricular flutter, ventricular fibrillation, agonal, asystole, LBBB, RBBB, $1^{st}$ degree AVB, $2^{nd}$ degree AVB (Type I), $2^{nd}$ degree AVB (Type II), $3^{rd}$ degree AVB, Q-wave infarction, ST segment elevation, ST segment depression, T-wave inversion, atrial paced, AV sequential paced, vent. Pacemaker (artificial), and/or other cardiac rhythms). Further, the heart sounds may be normal, distant, non-existent, include a systolic murmur, S3, and/or S4. The control system 1104 and/or a user utilizing the control system determines what heart sounds and at what rate the sounds are produced in some embodiments. The sounds produced by the heart sound module 1364 are detectable via use of a stethoscope in some instances. In some embodiments, at least a portion of the heart sound module 1364—such as a speaker—is positioned within the simulator 1350 where the natural heart would be.

The patient simulator 1350 also includes lung sound modules 1366, 1368, 1370, and 1372. In particular, lung sound module 1366 is utilized to simulate sounds of the upper right lung towards the front of the simulator 1350; lung sound module 1368 is utilized to simulate sounds of the upper left lung towards the front of the simulator; lung sound module 1370 is utilized to simulate sounds of the upper left lung towards the back of the simulator; lung sound module 1372 is utilized to simulate sounds of the upper right lung towards the back of the simulator. Each of the lung sound modules 1366, 1368, 1370, and 1372 is an audio module configured to produce sounds to simulate the natural sounds of a patient's lungs. In that regard, the lung sound modules 1366, 1368, 1370, and 1372 are configured to produce one or more of the following lung sounds in some embodiments: normal, none, wheezing, inspiration squeaks, crackles, rails, and/or other lung sounds. Further, the combination of lung sound modules 1366, 1368, 1370, and 1372 are utilized to simulate respiratory patterns including, but not limited to normal, Kussmaul's, Cheyne-Stokes, Biot's, apneusic, and/or other respiratory patterns. The combination of lung sound modules 1366, 1368, 1370, and 1372 are also utilized to simulate the respiratory rate of the patient. In that regard, the respiratory rate may be set at a constant rate and/or be set to change over time.

The patient simulator 1350 also includes opening module 1374 and closing module 1376. The opening and closing modules 1374 and 1376 are configured to control the blinking of the patient's simulated eyes. In particular, the opening module 1374 is utilized to open the eyelid of the simulator and the closing module 1376 is utilized to close the eyelid. Accordingly, with the eyelid open the closing module 1376 is activated followed by the opening module 1374 being activated to simulate the patient blinking. The rate, pattern, and speed of blinking are controlled by the control system 1104 in some instances. In some instances the rate of blinking ranges from 5 blinks per minute to 30 blinks per minute. In other embodiments, ranges outside of this are used. Further, the eyes can be maintained in an open position or a closed position. The speed of the blinks can be controlled as well. In some instances, the elapsed time or speed of each blink from open to closed to open is approximately 200 ms (e.g., approximately 100 ms to close and approximately 100 ms to reopen). However, the speed of the blinks can be increased or decreased as desired in some embodiments.

The patient simulator 1350 also includes a right lung valve 1378, a left lung valve 1380, and a breathing valve 1382. Together the right lung valve 1378, the left lung valve 1380, and the breathing valve 1382 control the flow of air into and out of the lungs of the simulator 1350. In that regard, each of the valves 1378, 1380, and 1382 comprise a pneumatic valve. In some embodiments, the breathing valve 1382 is utilized to control the respiratory rate of the simulator 1350. In that regard, the breathing valve 1382 opens and closes in order for the lungs to inflate and deflate at the desired rate. The right lung valve 1378 and the left lung valve 1380 are utilized to selectively disable the right and/or left lungs, respectively. Accordingly, in some embodiments when the right lung valve 1378 is opened it closes a 3-way air pilot valve such that air cannot flow from the breathing valve into the right lung. In such instances, air flows from the breathing valve solely into the left lung. The left lung valve 1380 operates in a similar manner in some embodiments. Factors such as disablement of the lungs, respiratory rate, respiratory pattern, inspiratory rate, and/or disablement of the left or right lung are controlled by the valves 1378, 1380, and 1382 based on signals received from the control system 1104 via the master module 1352.

The patient simulator 1350 also includes an ECG module 1384 or rhythm emulator. The ECG module is configured to emit an electrical signal that simulates the electrical activity of the heart of the simulator 1350. In some embodiments, the ECG module is configured to provide signals associated with each of the 12 leads such that a 12-lead ECG signal is available to the user. In some embodiments, the ECG module 1300 is configured to emit signals that simulate the presence of a myocardial infarction in various parts of the heart. In some embodiments, the position of the myocardial infarction is selected via the control system 1104. Accordingly, the ECG module is utilized to train users to identify the onset of heart attacks and/or the associated symptoms identifiable via an ECG. The electrical signal of the ECG module is detectable by standard ECG equipment.

The patient simulator 1350 also includes a K-sound module 1386 for the left arm of the simulator and a K-sound module 1388 for the right arm of the simulator. Each of the K-sound modules 1386 and 1388 are configured to produce a simulated K-sound (Korotkoff sound). In that regard, the K-sound modules 1386 and 1388 are utilized to allow a user to take the blood pressure of the patient simulator 1350 in some embodiments. Accordingly, the K-sounds produced by the modules 1386 and 1388 are determined based on a simulated heart rate and blood pressure. In some instances, the heart rate and blood pressure of the patient simulator 1350 are provided by a user or teacher via the control system 1104.

The patient simulator also includes a pupil dilation module 1390. The pupil dilation module 1390 is configured to control the dilation of the pupils of the simulator's eyes. In some embodiments, the pupil dilation of each of the simulator's eyes is controlled at least partially based on the amount of light received by an optical sensor positioned within the eye. Further, the maximum size of the pupil and/or the rate of change or dilation of the pupil are controlled by the control system 1104 in some instances. In some instances the parameters of the pupil dilation are selected to simulate a specific medical condition.

The patient simulator 1350 also includes a compression module 1392. The compression module 1392 is configured to monitor the force of chest compressions applied to the simulator 1350. In that regard, the compression module 1392 is configured to monitor the pressure applied and based on that pressure determine whether the pressure is too high, too low, or within the desired range. The compression module 1392 is in communication with the master module 1352, such that the determination of whether the correct pressure is being applied is relayed to the control system 1104. In some embodiments, the simulator 1350 will trend towards recovery or further complications based on whether the correct pressure is applied. For example, if the chest compressions are within the desired range of pressures then the patient simulator may show signs of recovery. On the other hand, if the chest compressions are outside the desired range of pressures then the patient simulator may develop additional problems or symptoms and/or make it more difficult to recover the simulator from the present symptoms.

The patient simulator 1350 also includes a left pedal pulse module 1394 and a right pedal pulse module 1396. The left and right pedal pulse modules 1394, 1396 are configured to simulate the pedal pulses of the simulator 1350. In that regard, in some embodiments the pedal pulse modules 1394, 1396 are electrical modules configured to simulate the pedal pulses. In other embodiments, the pedal pulse modules 1394, 1396 are pneumatic modules configured to simulate the pedal pulses. The patient simulator 1350 also includes a right radial pulse module 1398 and a left radial pulse module 1400. The right and left radial pulse modules 1398, 1400 are pneumatic modules for simulating the radial pulses of the simulator 1350.

The patient simulator 1350 also includes an intubation module 1402. The intubation module 1402 is configured to monitor intubation of the patient simulator 1350. In that regard, the depth of proper intubation for the patient simulator 1350 will depend on the size and/or age of the patient simulator. Accordingly, in the present embodiment where the simulator is approximately the size of a five-year old the intubation module 1402 is configured to determine the proper intubation depth for a five-year old. In some embodiments, the intubation module 1334 utilizes an optical sensor to monitor the depth of an intubation tube within the trachea of the patient simulator 1350. In some embodiments, the intubation module 1334 utilizes a pair of optical sensors spaced apart from one another to define the acceptable range of intubation depths. The first optical sensor is utilized to detect the presence of an intubation tube as it reaches the beginning of the acceptable range of depths. The second optical sensor is utilized to detect when the intubation tube has been advanced beyond the acceptable range of depths.

The patient simulator 1350 also includes a ventilation module 1404. The ventilation module 1404 is configured to monitor the use of a ventilation device applied to the simulator 1350. The ventilation device is a bag-valve mask in some instances. In other instances, the ventilation device is a user's mouth, such as in mouth-to-mouth resuscitation. The ventilation module 1404 is configured to monitor the pressure applied by the ventilation device and based on that pressure determine whether the pressure is too high, too low, or within the desired range. The ventilation module 1404 is in communication with the master module 1352, such that the determination of whether the correct pressure is being applied is relayed to the control system 1104. In some embodiments, the simulator 1350 will trend towards recovery or further complications based on whether the correct pressure is applied. For example, if the ventilation is within the desired range of pressures then the patient simulator may show signs of recovery. On the other hand, if the ventilation is outside the desired range of pressures then the patient simulator may develop additional problems or symptoms and/or make it more difficult to recover the simulator from the present symptoms.

The patient simulator 1350 also includes a color change modules 1406. The color change module 1406 is configured for controlling color change around the lips of the simulator 1350. The color change module 1406 is utilized in some embodiments to simulate cyanosis of the patient simulator 1350. Accordingly, the color change module 1406 is configured to simulate different levels of cyanosis of the patient simulator 1350. In that regard, the degree of cyanosis is determined by the control system 1104 and/or a user of the control system 1104 in some embodiments. The degree of cyanosis may trend—increase and/or decrease—based on a variety of parameters including the efficacy of any treatments administered. In some embodiments, the trending is controlled manually via the control system 1104. In other embodiments, the trending is at least partially controlled by a physiological simulator software application of the control system 1104.

The patient simulator 1350 also includes a right blood pressure cuff module 1408 and a left blood pressure cuff module 1410. The left and right blood pressure cuff modules 1408 and 1410 are pressure modules configured to allow a user to take a simulated blood pressure of the patient simulator 1350. The blood pressure cuff modules 1408 and 1410 are configured for use with standard blood pressure monitors in some embodiments.

In some embodiments, the patient simulator 1350 also includes a compressor module 1412 for controlling a compressor of the simulator 1350. Generally, the compressor is utilized to provide a compressed air supply to the various pneumatic devices and modules of the simulator 1350. For example, in some embodiments the compressor is utilized to provide air to modules for simulating the lungs, pulses, contractions, tummy pressure, seizures, eye dilation, blinking, and/or other aspects of the patient simulator 1350. In some embodiments, the compressor provides pressurized air to one or more air reservoirs or accumulators that are then connected to the various pneumatic modules of the simulator 1350. In that regard, the air reservoirs may maintain different air pressures such that different pneumatic modules are connected to the air reservoir with the appropriate air pressure for its application. In some instances, the pneumatic modules of the patient simulator 1350 that utilize the compressor are configured to run at a relatively low air pressure, e.g., less than 10 psi in some embodiments and less than 5 psi in other embodiments. In some instances, the simulator 1350 includes two accumulators with one of the accumulators maintaining an air pressure of approximately 5 psi and the other accumulator maintaining an air pressure of approximately 1 psi. In other embodiments, the accumulators maintain other air pressures. Generally, however, the patient simulator 1350 and its associated components are configured to operate at low pressures, which helps prevent the introduction of water into the simulator associated with high pressure systems. The introduction of water into the simulator that results from using high pressure systems can cause damage to the simulator, increase the maintenance costs, and require additional components to remove or limit the amount of water within the simulator.

Further, the compressor is sized to fit entirely within the simulator 1350 in some embodiments. In that regard, the compressor operates quietly so as not to interfere with the other simulation aspects of the simulator 1350 and, in particular, the audible simulation aspects. Accordingly, in some instances a muffler system is utilized to minimize the noise generated by the compressor. The muffler system is utilized on the input, output, and/or both sides of the compressor in some embodiments. Further, the compressor is self-cooling in some instances. In one such embodiment, the compressor includes a plurality of metal pipes surrounding at least the compressor motor that intake air is passed through. The intake air passing through the metal pipes helps to dissipate the heat generated by the compressor. Accordingly, the compressor is able to operate entirely within the simulator 1350 without overheating or disturbing the other simulation aspects of the simulator. This allows the simulator 1350 to be fully functional without attachment to a noisy, external, high pressure compressor.

Each of the various modules of the simulator 1350 is connected to the master module 1252 via a power wire, a ground wire, and/or a 2-way communication wire. Accordingly, the master module 1252 is utilized to control the activation, deactivation, and power consumption of the modules in some embodiments. In some embodiments, the master module 1252 is controlled or directed via a software program of the control system 1104. In some embodiments, the master module 1252 is in wireless communication with one or more of the modules. In some embodiments, the modules themselves are interconnected via the communication wire or an additional communication wire. In that regard, in some instances a non-master module acts as a master module for a subset of modules.

As described above, each of the simulators 1102, 1250, and 1350 comprise a plurality of modules each adapted for performing various functions of the simulator. In some embodiments, different modules are similar modules programmed for different purposes. In that regard, in some instances the plurality of modules are derived from common set of base modules. In some instances, the base modules include master modules, interface modules, pneumatic modules, audio modules, sensor modules, and driver modules. These various base modules are adapted or programmed for the various specific purposes of the simulators and modules as described herein. In that regard, it should be noted that modules are created for the desired or intended functions of the simulators and may include modules not specifically described herein. These base modules will now be described in greater detail.

Figure 32:
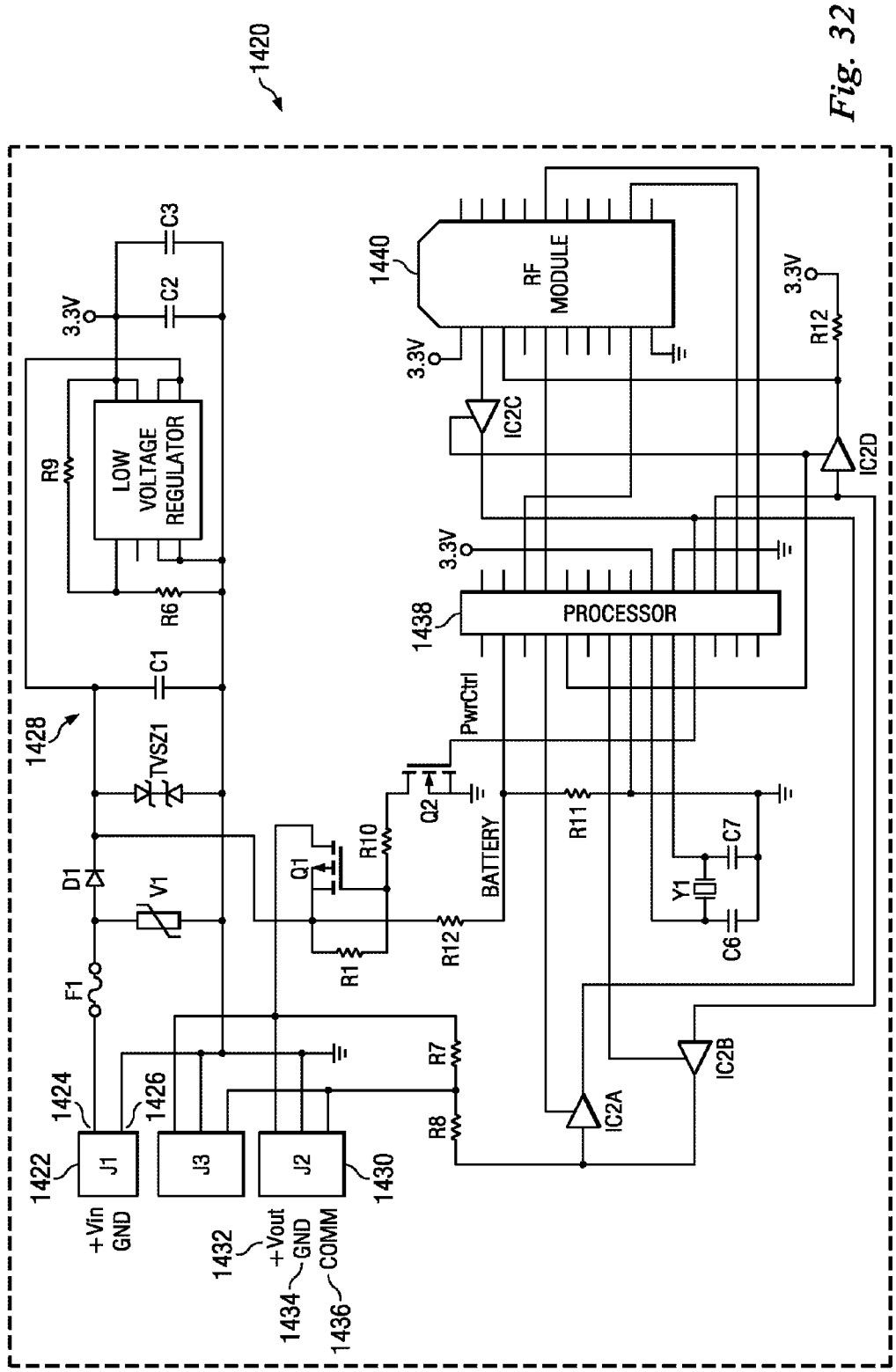
FIG. 32 is a diagrammatic schematic view of a master module for use in a patient simulator system according to one embodiment of the present disclosure.

Referring now to FIG. 32, shown therein is a diagrammatic schematic view of a master module 1420 for use in a patient simulator according to one embodiment of the present disclosure. In some instances the master module 1420 is utilized as the master modules 1106, 1252, and/or 1352 of the simulators described above. In that regard, the master module 1420 is configured to interface with the various modules of the simulators and the control system. Specifically, the master module 1420 links the various modules together and transfers information and signals between the various modules and between the modules and the control system. In that regard, the master module 1420 is configured to receive commands from the control system and relay those commands to the modules. In some instances communication between the master module 1420 and the control system is accomplished in 100 ms or less such that the commands of the control system are executed in approximately real time and on demand. The master module 1420 is configured to receive information from and/or monitor the modules and relay that information to the control system. In that regard, the master module 1420 monitors and/or reads some of the sensor modules constantly. The frequency of the monitoring and/or reading is determined by the specific function being monitored. Some of the modules are monitored many times per second, while other modules are monitored less frequently. Monitoring the modules includes obtaining sensor data from the modules (e.g., amount of compression or ventilation) as well as general information regarding the module (e.g., on/off, connected or not connected, etc.). The general information including the status and/or the presence of modules within the simulator is available to the user via the control system in some embodiments. In that regard, modules of the simulator are activated and deactivated via the control system in some instances.

As shown in FIG. 32, the master module 1420 includes an input 1422. The input 1422 includes a power supply input 1424 and a ground 1426. In some embodiments, the power supply input 1424 is configured to receive power from a battery located within the simulator. Accordingly, the power supply input 1424 is configured to receive direct current power in such embodiments. In other embodiments, the power supply input 1424 is configured to receive alternating current power, such as from a wall outlet. The master module 1420 also includes a low voltage regulator 1428 that regulates the power received from the power supply input 1424. The master module 1420 also includes an output 1430. The output 1430 is utilized to connect the master module 1420 to the other modules of the simulator. As discussed above the connection between the master module 1420 and the other modules includes a power supply, a ground, and a 2-way communication cable. Accordingly, the output 1430 includes a power output 1432, a ground 1434, and a communication output 1436. The master module 1420 also includes a processor 1438 for processing the various information requests, data transfers, and other functions performed by the master module. Finally, the master module 1420 includes a communication device 1440. In the current embodiment, the communication device 1440 comprises an RF module. In other embodiments, the communication device 1440 may be any other type of communication module that facilitates communication with the control system including both wireless and wired communication systems.

Figure 33:
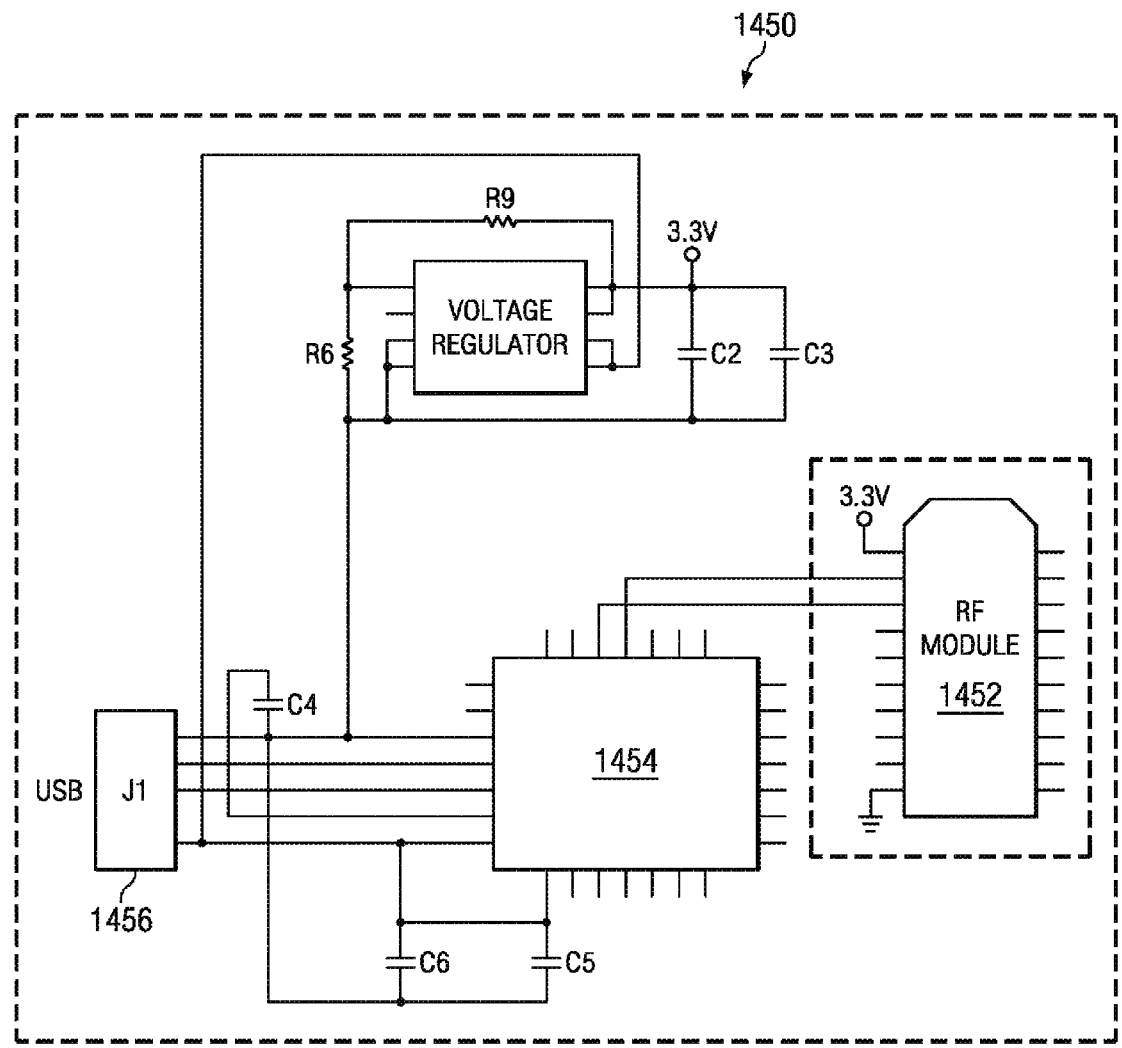
FIG. 33 is a diagrammatic schematic view of a communication module for use in a patient simulator system according to one embodiment of the present disclosure.

Referring now to FIG. 33, shown therein is a diagrammatic schematic view of a communication module 1450 for use in a patient simulator system according to one embodiment of the present disclosure. The communication module 1450 is configured to communicate with the communication device 1440 of the master module 1420 in some embodiments. In that regard, the communication device 1440 is configured for use as a part of or a link to the control system. In the current embodiment, the communication device 1440 includes an RF module 1452 for communicating the RF module of the master module 1420. The communication device 1440 also includes a processor 1454 and an output 1456. In some embodiments, the processor 1454 is configured to convert the signals received via RF module 1452 into an output form for transmission out the output 1456. In the present embodiment, the output 1456 is a USB connector that is or may be connected to a computer system of the control system.

Figure 34:
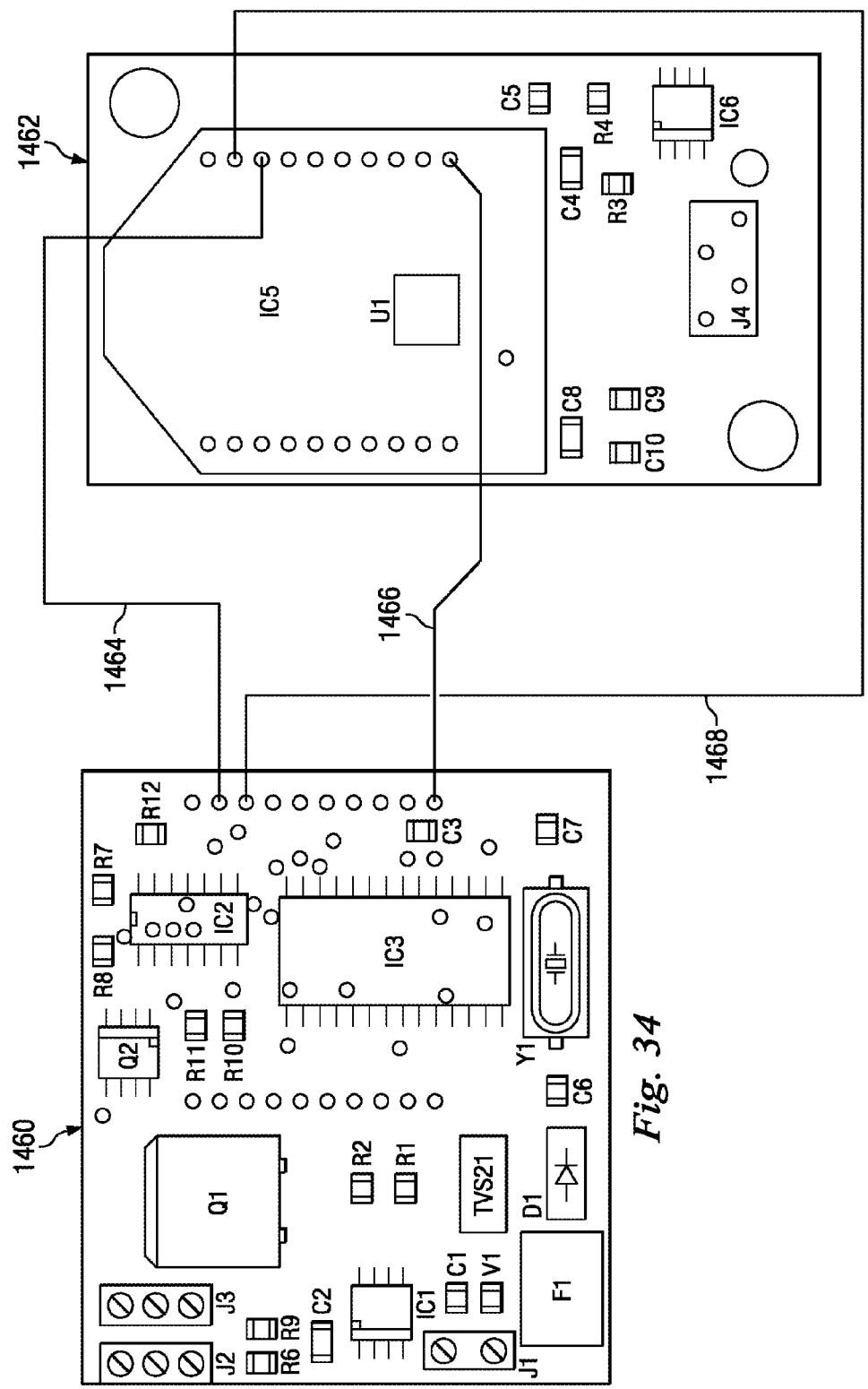
FIG. 34 is a diagrammatic schematic view of a communication module for use in a patient simulator system according to another embodiment of the present disclosure.

Referring now to FIG. 34, shown therein is a diagrammatic schematic view of a communication module 1460 for use in a patient simulator system according to another embodiment of the present disclosure. The communication module 1460 is configured to communicate with a master module 1462 of the simulator in some embodiments. In that regard, the communication device 1460 is configured for use as a part of or a link to a control system. In the current embodiment, the communication device 1460 is hard wired to the master module 1462 via lines 1464, 1466, and 1468. In the present embodiment, the communication module 1460 provides a USB output connector that is or may be connected to a computer system of the control system.

Figure 35:
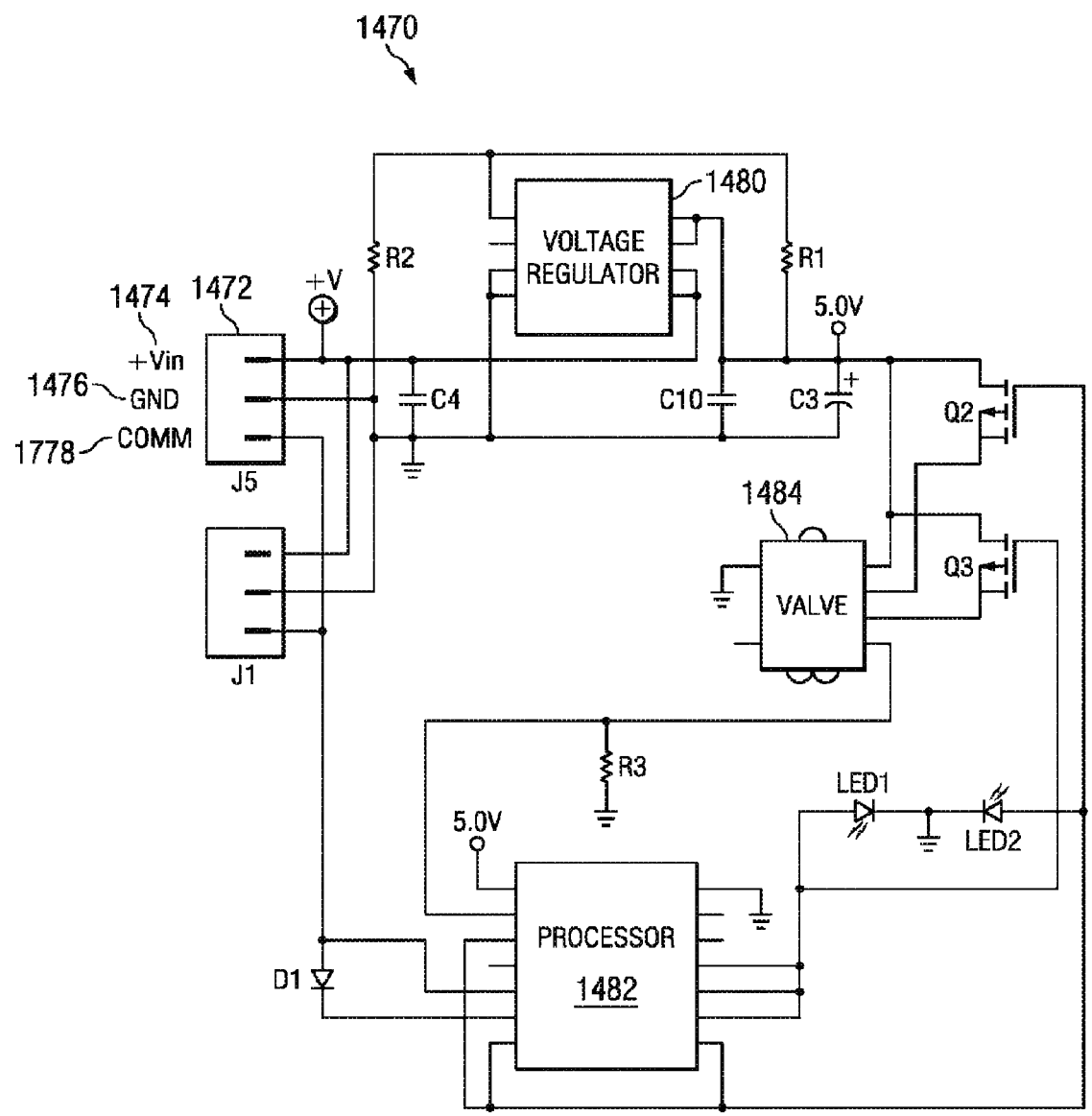
FIG. 35 is a diagrammatic schematic view of a pneumatic module for use in a patient simulator system according to one embodiment of the present disclosure.

Referring now to FIG. 35, shown therein is a diagrammatic schematic view of a pneumatic module 1470 for use in a patient simulator system according to one embodiment of the present disclosure. The pneumatic module 1470 includes an input 1472. The input 1472 is configured to connect the pneumatic module 1470 to a master module, such as master module 1420. In that regard, the input 1472 includes a power input 1474, a ground 1476, and a communication input 1478. Accordingly, the input 1472 is in communication with the output 1430 of the master module 1420. The communication input 1478 also serves as a communication output for 2-way communication between the pneumatic module 1470 and the master module 1420. The pneumatic module 1470 also includes a voltage regulator 1480 and a processor 1482. The processor 1482 is programmed differently depending on the particular function of the pneumatic module 1470. For example, in some instances the pneumatic module 1470 is programmed to serve as a breathing valve module, lung valve module, larynges module, pharynges module, pneumothorax module, pneumothorax release module, tongue module, arm motion module, baby release module, eye blinking module, eye closing module, pupil dilation module, seizure module, pulse module, color change module, tummy valve module, and/or other modules for use in a simulator. Depending on the programming of the processor 1482 and the signals received from the master module 1420, an output 1484 of the pneumatic module 1470 causes an associated valve to either be opened or closed.

Figure 36:
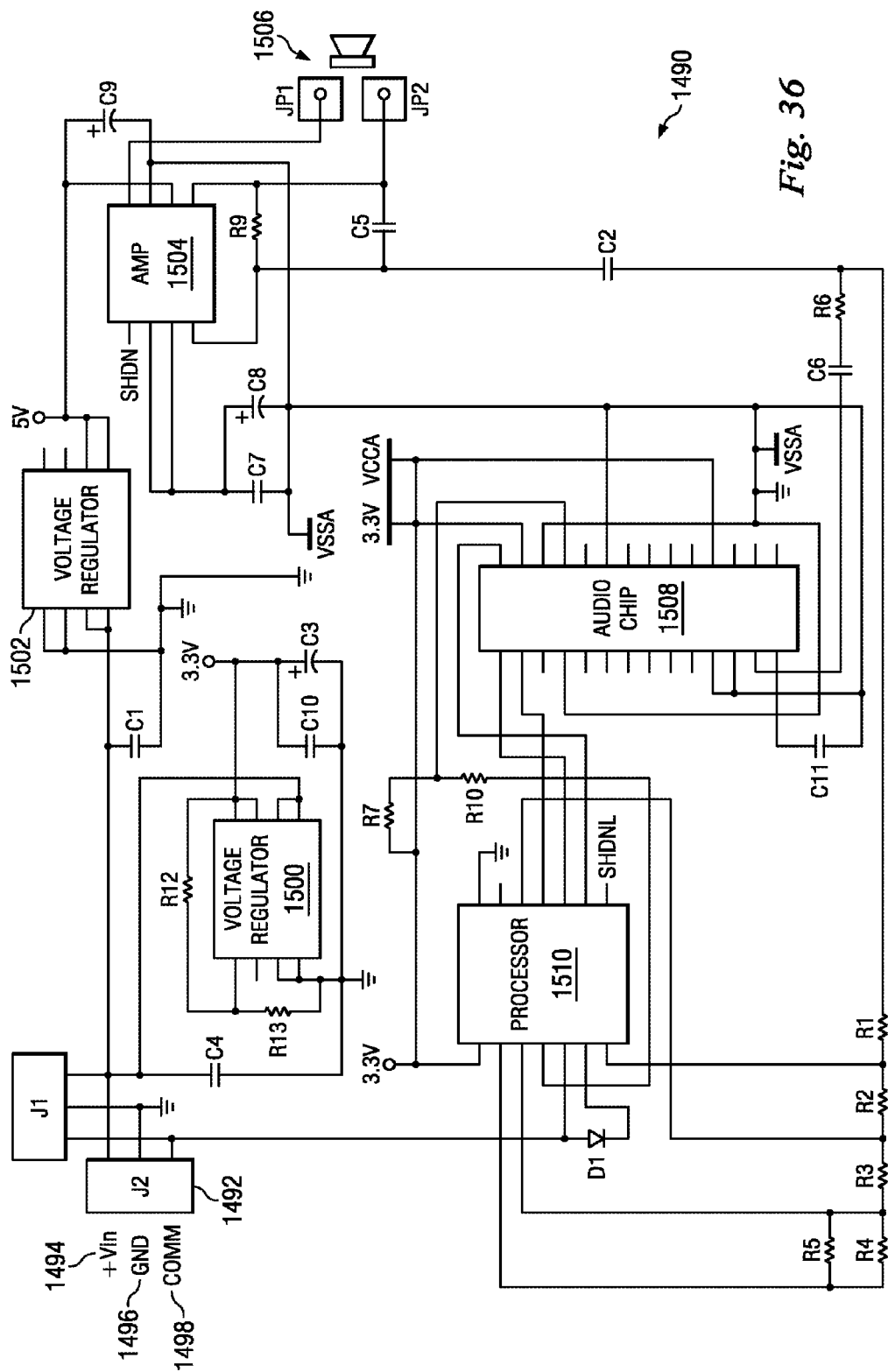
FIG. 36 is a diagrammatic schematic view of an audio module for use in a patient simulator system according to one embodiment of the present disclosure.

Referring now to FIG. 36, shown therein is a diagrammatic schematic view of an audio module 1490 for use in a patient simulator according to one embodiment of the present disclosure. The audio module 1490 includes an input

1492. The input 1492 is configured to connect the audio module 1490 to a master module, such as master module 1420. In that regard, the input 1492 includes a power input 1494, a ground 1496, and a communication input 1498. Accordingly, the input 1492 is in communication with the output 1430 of the master module 1420. The communication input 1498 also serves as a communication output for 2-way communication between the audio module 1490 and the master module 1420 in some embodiments. The audio module 1490 includes a voltage regulator 1500 and a voltage regulator 1502. The voltage regulator 1502 is configured to provide power to an amplifier 1504, which drives an audio output or speaker 1506. The audio module 1490 also includes an audio chip 1508 and a processor 1510. The audio chip 1508 and/or the processor 1510 are programmed differently depending on the particular function of the audio module 1490. For example, in some instances the audio module 1490 is configured to serve as a lung sound module, heart sound module, K-sound module, voice module, womb sound module, and/or other sound modules for use in a simulator. The audio chip 1508 and/or the processor 1510 are configured for the particular function of the audio module 1490. In some embodiments, the audio module 1490 includes memory associated with the audio chip 1508 or the processor 1510 that includes a plurality of prerecorded sounds thereon. The audio module 1470 selectively plays the prerecorded sounds in such embodiments. In some embodiments, the playing of the prerecorded sounds is determined at least in part by signals received from the control system via the master module 1420.

Figure 37:
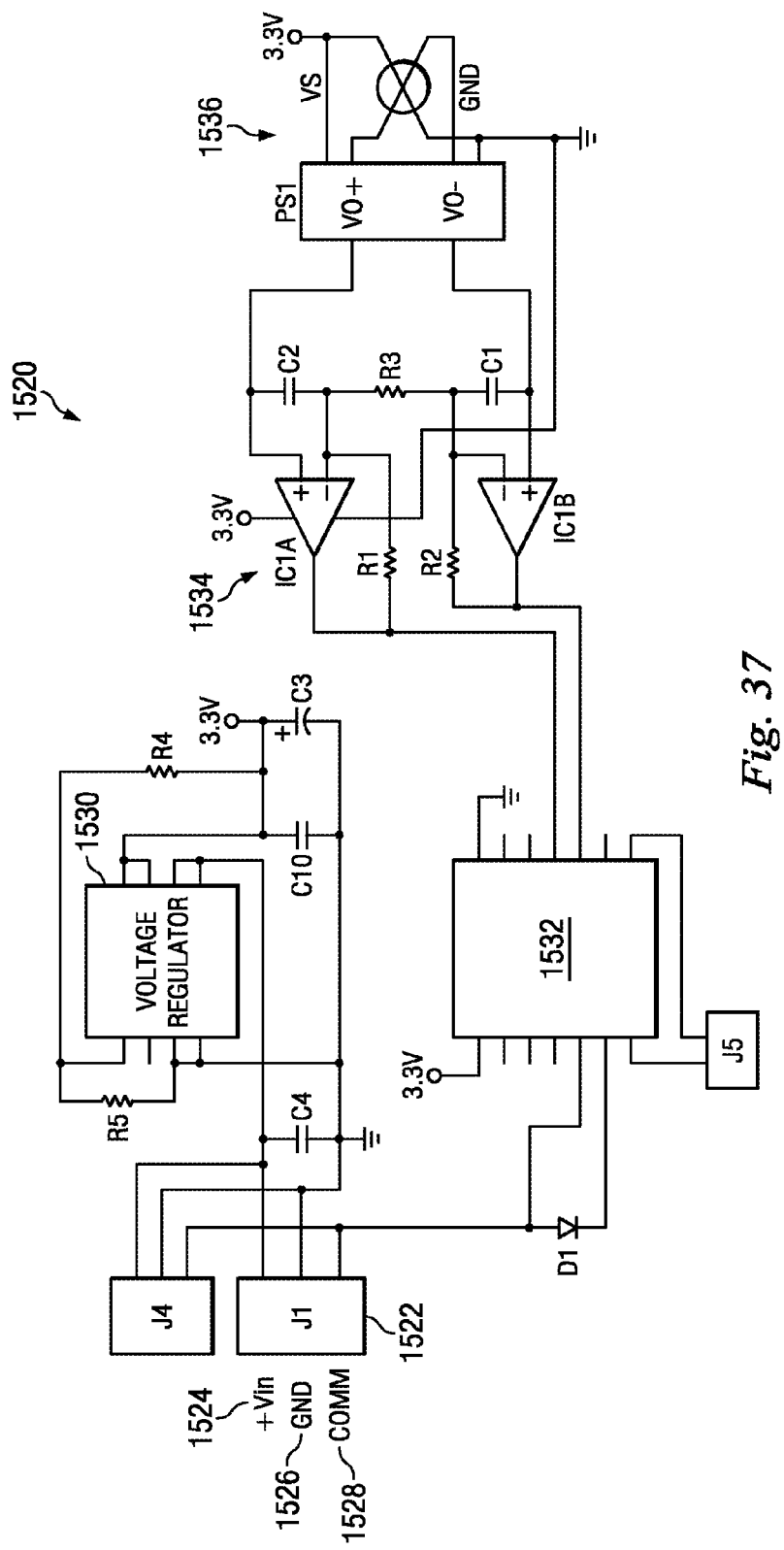
FIG. 37 is a diagrammatic schematic view of a sensing module for use in a patient simulator system according to one embodiment of the present disclosure.

Referring now to FIG. 37, shown therein is a diagrammatic schematic view of a sensing module 1520 for use in a patient simulator according to one embodiment of the present disclosure. The sensing module 1520 includes an input 1522. The input 1522 is configured to connect the sensing module 1520 to a master module, such as master module 1420. In that regard, the input 1522 includes a power input 1524, a ground 1526, and a communication input 1528. Accordingly, the input 1522 is in communication with the output 1430 of the master module 1420. The communication input 1528 also serves as a communication output for 2-way communication between the sensing module 1520 and the master module 1420 in some embodiments. The sensing module 1520 includes a voltage regulator 1530 and a processor 1532. In some instances the voltage regulator 1530 is configured to provide power to an amplifier 1534. The amplifier 1534 is used in some embodiments to amplify the signal received from a sensor 1536. In other embodiments, the amplifier 1534 is used to drive the sensor 1536. The sensor 1536 is used to monitor a parameter associated with the various functions of the simulator. Accordingly, in some embodiments the sensor 1536 is a force sensor, load sensor, position sensor, optical sensor, temperature sensor, pH sensor, and/or other sensor for use in the simulator. In that regard, the amplifier 1534 and/or the processor 1532 are programmed differently depending on the particular function of the sensing module 1520. For example, in some instances the sensing module 1520 is configured to serve as a breathing valve module, blood pressure module, compressor module, ventilation module, compression module, load cell module, pulse module, other sensing module, and/or part thereof for use in a simulator.

Figure 38:
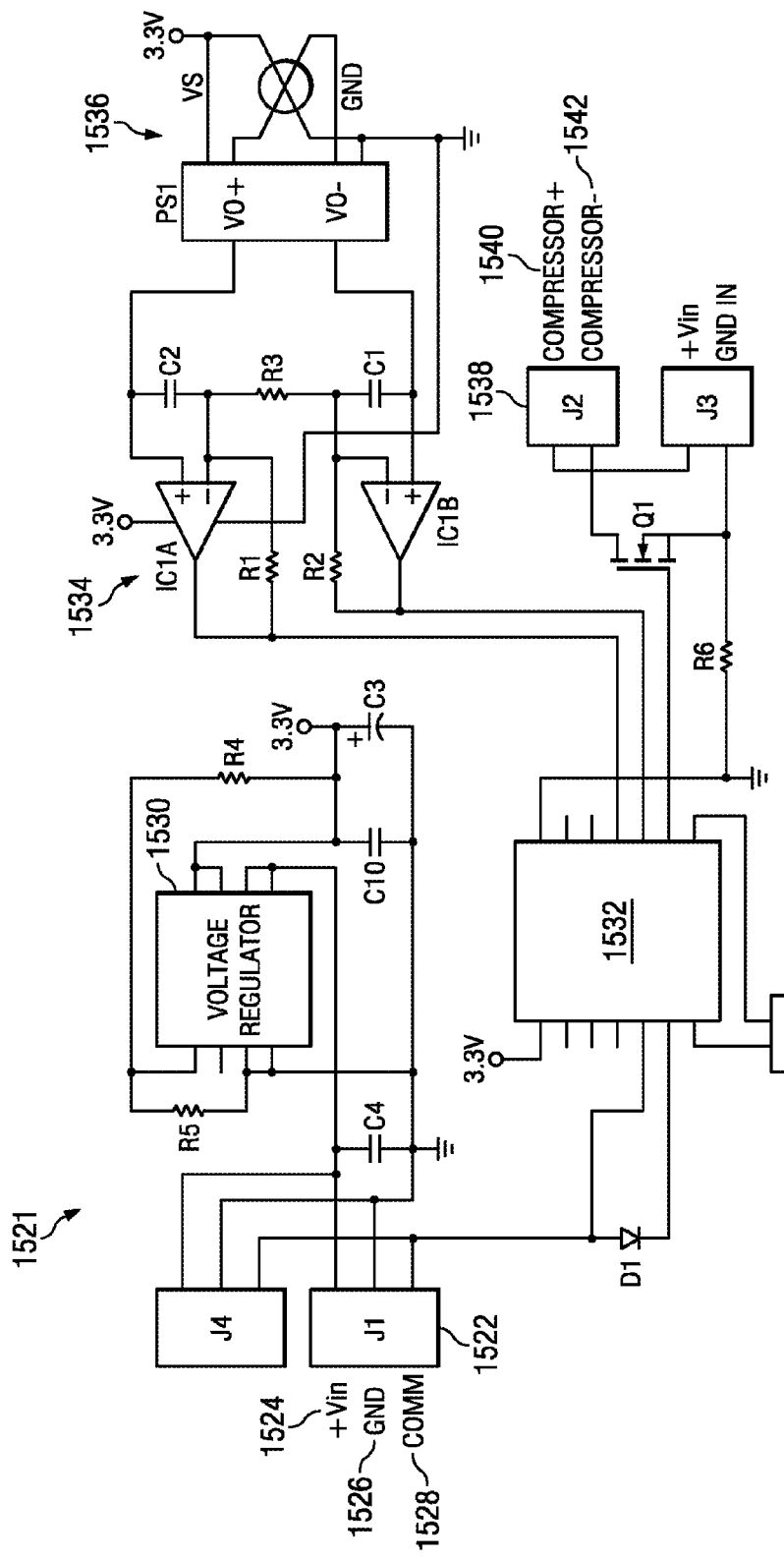
FIG. 38 is a diagrammatic schematic view of a sensing driver module for use in a patient simulator system according to one embodiment of the present disclosure.

Referring now to FIG. 38, shown therein is a diagrammatic schematic view of a sensing driver module 1521 for use in a patient simulator according to one embodiment of the present disclosure. In some aspects the sensing driver module 1521 is similar to the sensing module 1520 described above with respect to FIG. 37. However, in addition to the sensing aspects of the sensing module 1520, the sensing driver module 1521 includes a driver 1538. In that regard, the sensing driver module 1521 is configured to drive or actuate a device based on the sensed parameters of the module. For example, in the current embodiment the driver 1538 is configured to drive a compressor of the simulator. In that regard the sensing driver module 1521 may be utilized to maintain a desired air pressure within a reservoir supplied by the compressor. Accordingly, the sensor 1536 is utilized to monitor the pressure within the reservoir and then based on the sensed pressure the driver 1538 can be activated to adjust the pressure in the reservoir to the desired pressure. In that regard, the driver 1538 includes a first output 1540 for activating the compressor to increase the pressure and a second output 1542 for reducing the pressure. In other embodiments, the driver 1538 drives devices other than a compressor, including mechanical actuators, pneumatic actuators, electrical actuators, and/or other components of the simulator. In that regard, the sensing driver module 1520 is configured to serve as a breathing valve module, blood pressure module, compressor module, ventilation module, compression module, load cell module, pulse module, other sensing driver module, and/or part thereof for use in a simulator.

Figure 39:
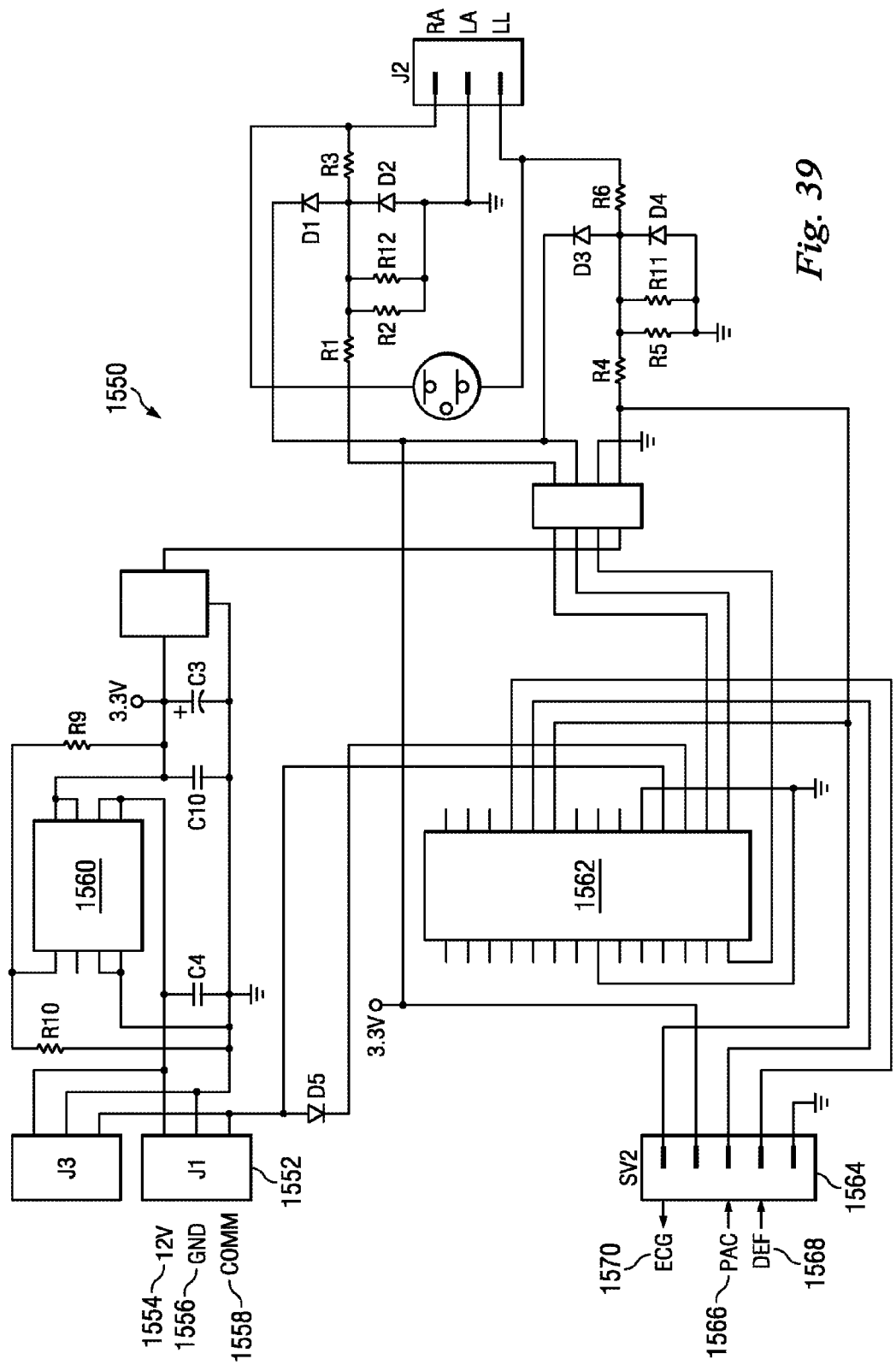
FIG. 39 is a diagrammatic schematic view of an ECG module for use in a patient simulator system according to one embodiment of the present disclosure.

Referring now to FIG. 39, shown therein is a diagrammatic schematic view of an ECG module 1550 for use in a patient simulator according to one embodiment of the present disclosure. The ECG module 1550 includes an input 1552. The input 1552 is configured to connect the ECG module 1550 to a master module, such as master module 1420. In that regard, the input 1552 includes a power input 1554, a ground 1556, and a communication input 1558. Accordingly, the input 1552 is in communication with the output 1430 of the master module 1420. The communication input 1558 also serves as a communication output for 2-way communication between the ECG module 1550 and the master module 1420 in some embodiments. The ECG module 1550 includes a voltage regulator 1560 and a processor 1562. The ECG module 1550 is configured to emit electrical signals that simulate the electrical activity of the heart of the simulator. In some embodiments, the ECG module is configured to provide signals associated with each of the 12 leads such that a 12-lead ECG signal is provided by the simulator. In some embodiments, the ECG module is configured to emit signals that simulate the presence of a myocardial infarction in various parts of the heart. In some embodiments, the position of the myocardial infarction is selected via the control system. The processor 1562 is programmed to execute each of the desired ECG simulations. The ECG module is utilized to train users to identify the onset of heart attacks and/or the associated symptoms identifiable via an ECG. The electrical signal of the ECG module is detectable by standard ECG equipment. In some embodiments the electrical signal of the ECG module is an analog signal. The ECG module 1550 also includes an input/output connector 1564. The input/output connector 1564 connects the ECG module 1550 to a pacer/defib module, such as pacer/defib module 1580 described with respect to FIG. 40 below. Generally, the input/output connector 1564 is configured to receive pacer info 1566 and defib info 1568 from the pacer/defib module 1580 and output ECG data or signals 1570 to the pacer/defib module.

Figure 40:
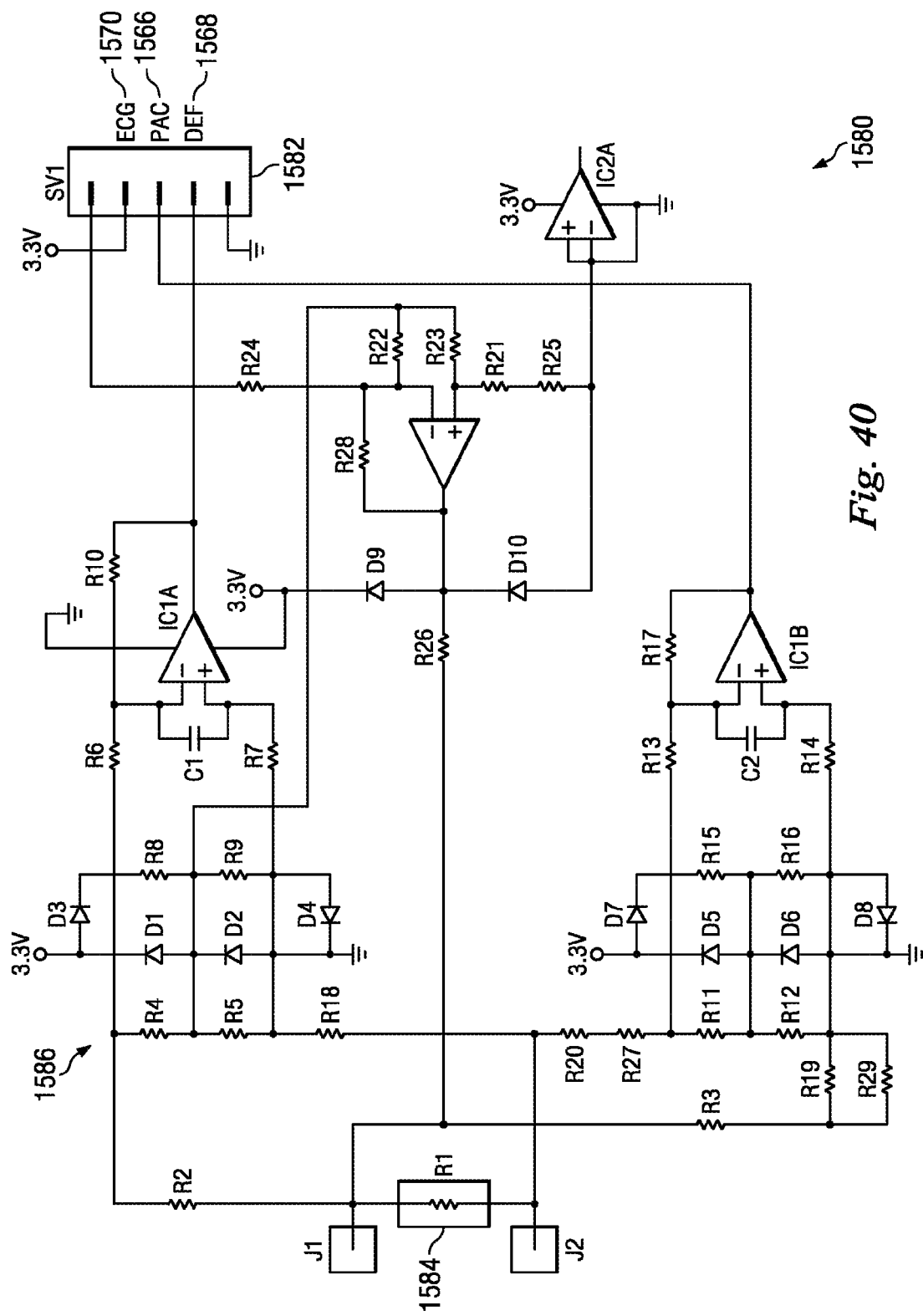
FIG. 40 is a diagrammatic schematic view of a Pacer/Defib module for use in a patient simulator system according to one embodiment of the present disclosure.

Referring now to FIG. 40, shown therein is a diagrammatic schematic view of a Pacer/Defib module 1580 for use in a patient simulator according to one embodiment of the present disclosure. The pacer/defib module 1580 is configured to allow external pacing and defibrillation from the same location. The pacer/defib module 1580 includes an input/output connector 1582. The input/output connector 1564 is configured to send pacer info 1566 and defib info 1568 to the ECG module 1550 and receive ECG data or signals 1570 from the ECG module. The pacer/defib module 1580 is configured to simulate the natural resistance of patient. To that end, the pacer/defib module 1580 includes a resistor 1584 sized to simulate the resistance of the patient. In that regard, the resistance of the resistor 1584 may vary depending on the size, age, and/or other characteristics of the simulator. The pacer/defib module 1580 also includes circuitry 1586 for conditioning the analog signal created by the pacer/defib module 1580.

Figure 41:
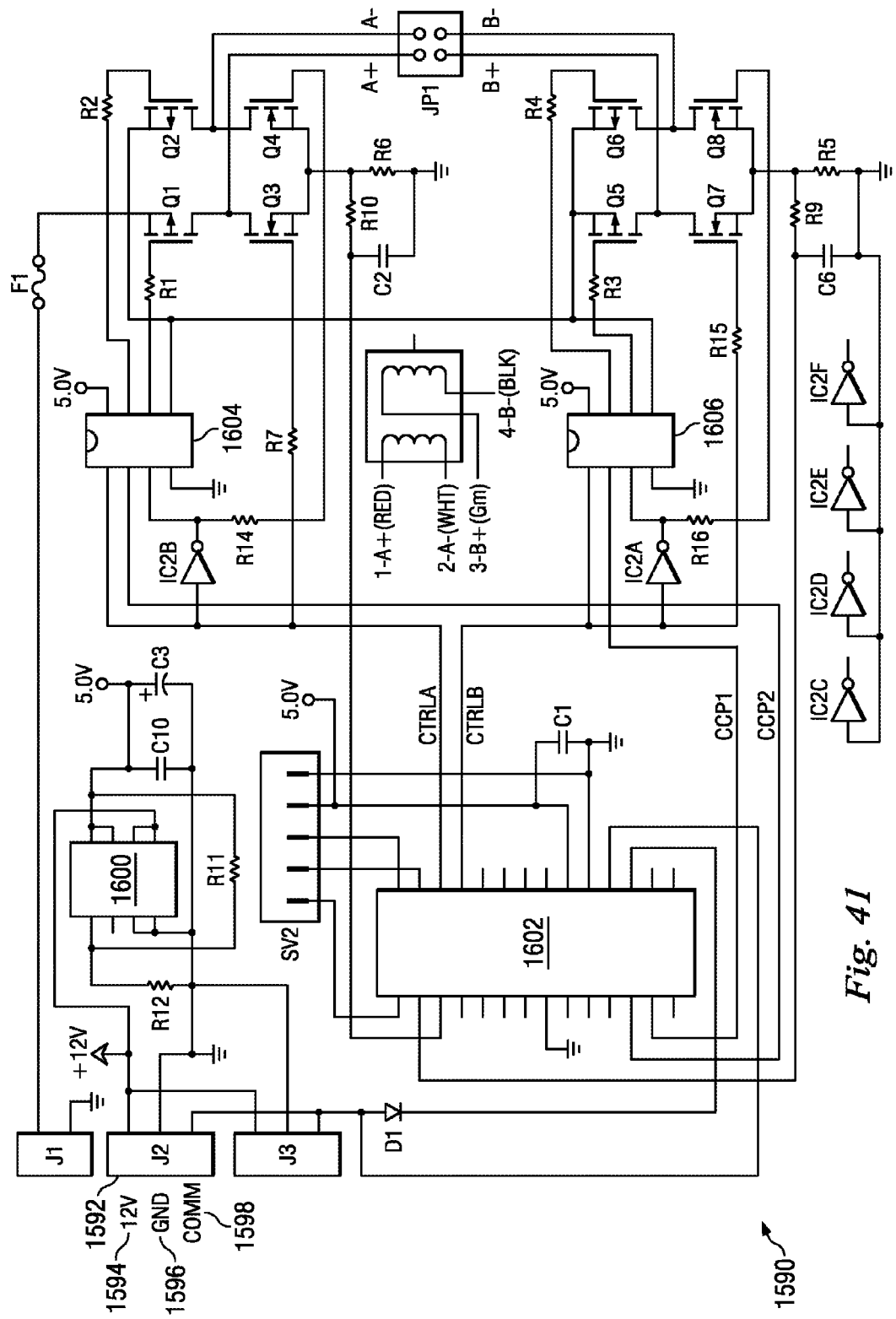
FIG. 41 is a diagrammatic schematic view of a motor driver module for use in a patient simulator system according to one embodiment of the present disclosure.

Referring now to FIG. 41, shown therein is a diagrammatic schematic view of a motor driver module 1590 for use in a patient simulator system according to one embodiment of the present disclosure. The motor driver module 1590 includes an input 1592. The input 1592 is configured to connect the motor driver module 1590 to a master module, such as master module 1420. In that regard, the input 1592 includes a power input 1594, a ground 1596, and a communication input 1598. Accordingly, the input 1592 is in communication with the output 1430 of the master module 1420. The communication input 1598 also serves as a communication output for 2-way communication between the motor driver module 1590 and the master module 1420 in some embodiments. The motor driver module 1590 includes a voltage regulator 1600 and a processor 1602. The processor 1602 is programmed to control drivers 1604 and 1606. The drivers 1604 and 1606 are configured to actuate a motor. In that regard, the drivers 1604 and 1606 are configured to drive motors for use in translation, rotation, and vibrations. Accordingly, in some embodiments the motor driver module 1590 is configured for use as a delivery module, a rotation module, a seizure module, a vibration module, and/or other module associated with a motor of the simulator.

Figure 42:
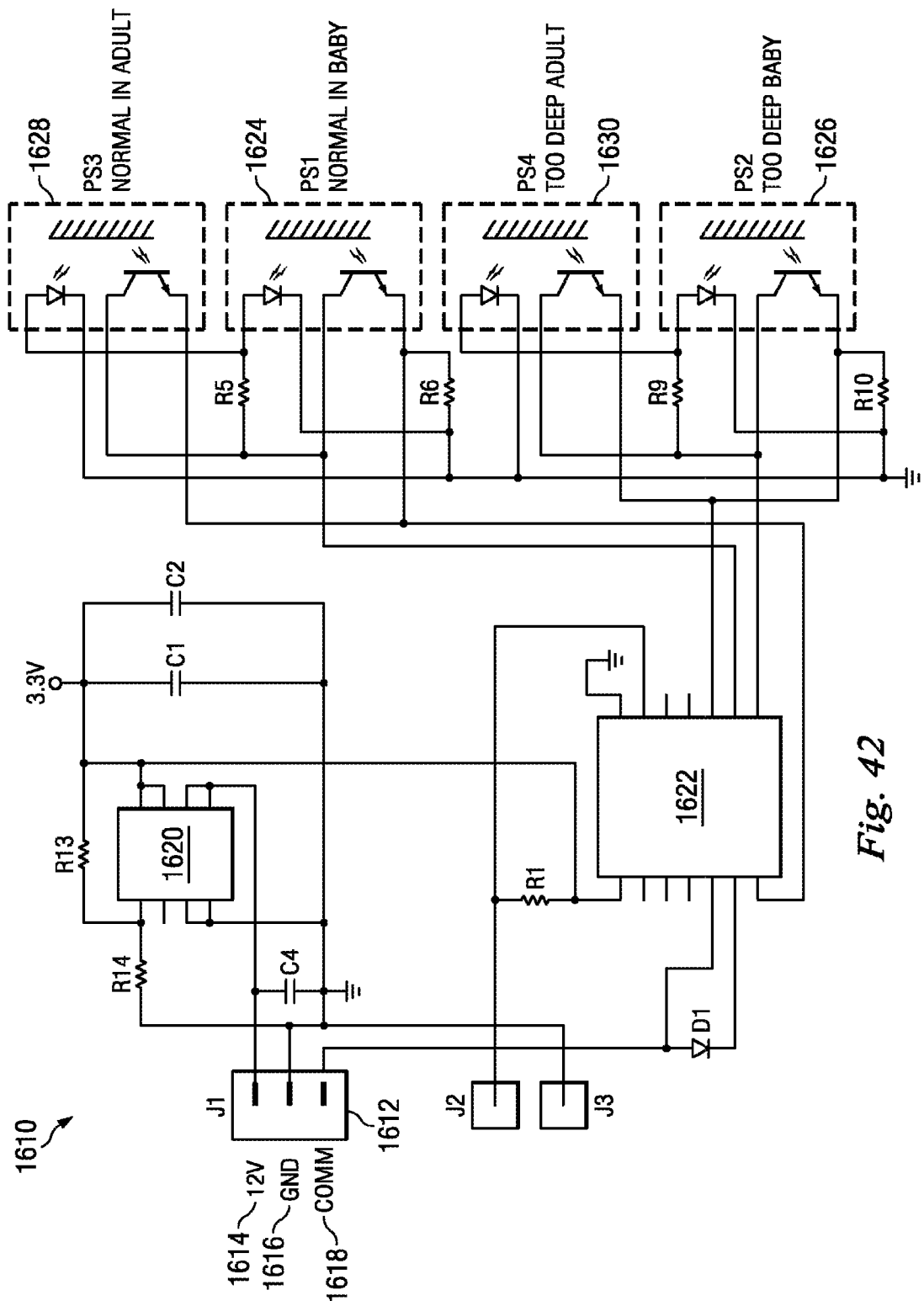
FIG. 42 is a diagrammatic schematic view of an intubation module for use in a patient simulator system according to one embodiment of the present disclosure.

Referring now to FIG. 42, shown therein is a diagrammatic schematic view of an intubation module 1610 for use in a patient simulator system according to one embodiment of the present disclosure. The intubation module 1610 includes an input 1612. The input 1612 is configured to connect the intubation module 1610 to a master module, such as master module 1420. In that regard, the input 1612 includes a power input 1614, a ground 1616, and a communication input 1618. Accordingly, the input 1612 is in communication with the output 1430 of the master module 1420. The communication input 1618 also serves as a communication output for 2-way communication between the intubation module 1610 and the master module 1420 in some embodiments. The intubation module 1610 includes a voltage regulator 1620 and a processor 1622. The intubation module 1610 is configured to monitor intubation of the patient simulator. In that regard, the depth of proper intubation for the patient simulator will depend on the size and/or age of the patient simulator. Accordingly, in the current embodiment the intubation module 1610 includes a first pair of optical sensors 1624 and 1626 for monitoring intubation in a baby and a second pair of optical sensors 1628 and 1630 for monitoring intubation in an adult. In other embodiments, other ages of simulator are accounted for. Only one pair of optical sensors is activated. The activated pair is chosen based on the size of the simulator in which the intubation module 1610 is being utilized. In other embodiments, the intubation module 1610 includes only a single pair of optical sensors spaced appropriately for the size and/or age of the patient simulator. The intubation module 1610 utilizes the optical sensors to monitor the depth of an intubation tube within the trachea of the patient simulator. In that regard, the optical sensors 1624 and 1628 are utilized to detect the presence of an intubation tube as it reaches the beginning or minimum of the acceptable range of depths. The optical sensors 1626 and 1630 are utilized to detect when the intubation tube has been advanced beyond the maximum acceptable range of intubation depths.

Figure 43:
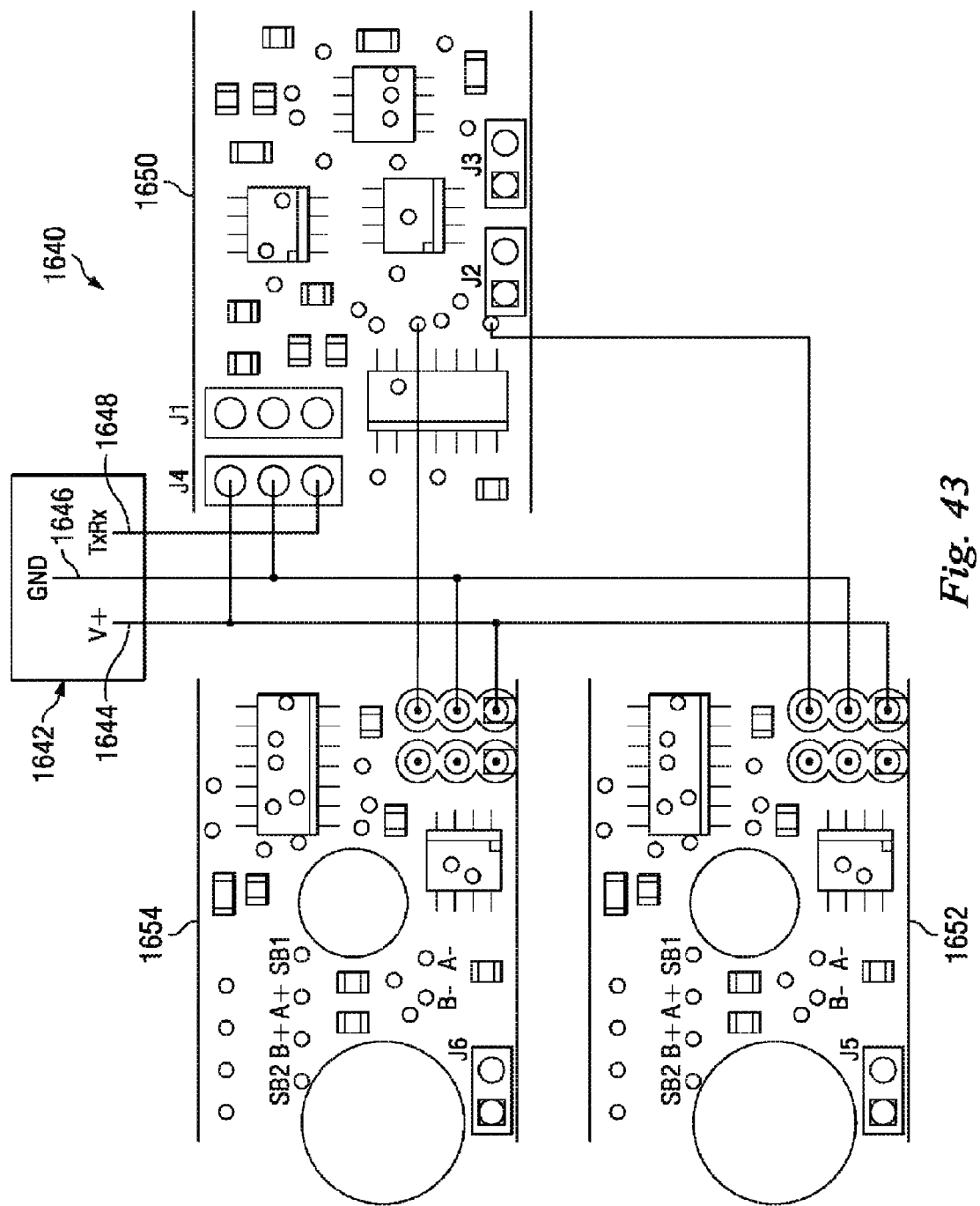
FIG. 43 is a diagrammatic schematic view of an inflation/deflation module for use in a patient simulator system according to one embodiment of the present disclosure.

Referring now to FIG. 43, shown therein is a diagrammatic schematic view of an inflation/deflation module 1640 for use in a patient simulator according to one embodiment of the present disclosure. In some embodiments the inflation/deflation module 1640 is utilized to simulate a pregnant mother's tummy. The inflation/deflation module 1640 includes an input 1642. The input 1642 is configured to connect the inflation/deflation module 1640 to a master module, such as master module 1420. In that regard, the input 1642 includes a power input 1644, a ground 1646, and a communication input 1648. Accordingly, the input 1642 is in communication with the output 1430 of the master module 1420. The communication input 1648 also serves as a communication output for 2-way communication between the inflation/deflation module 1640 and the master module 1420 in some embodiments. The inflation/deflation module 1640 includes a pressure sensing module 1650, an inflation module 1652, and a deflation module 1654. The inflation and deflation modules 1652 and 1654 comprise pneumatic valves in some embodiments. The inflation/deflation module 1640 is configured to monitor the pressure within a reservoir of the simulator using the pressure sensing module 1650 and then adjust the pressure to the desired pressure using the inflation and deflation modules 1652 and 1654.

Figure 44:
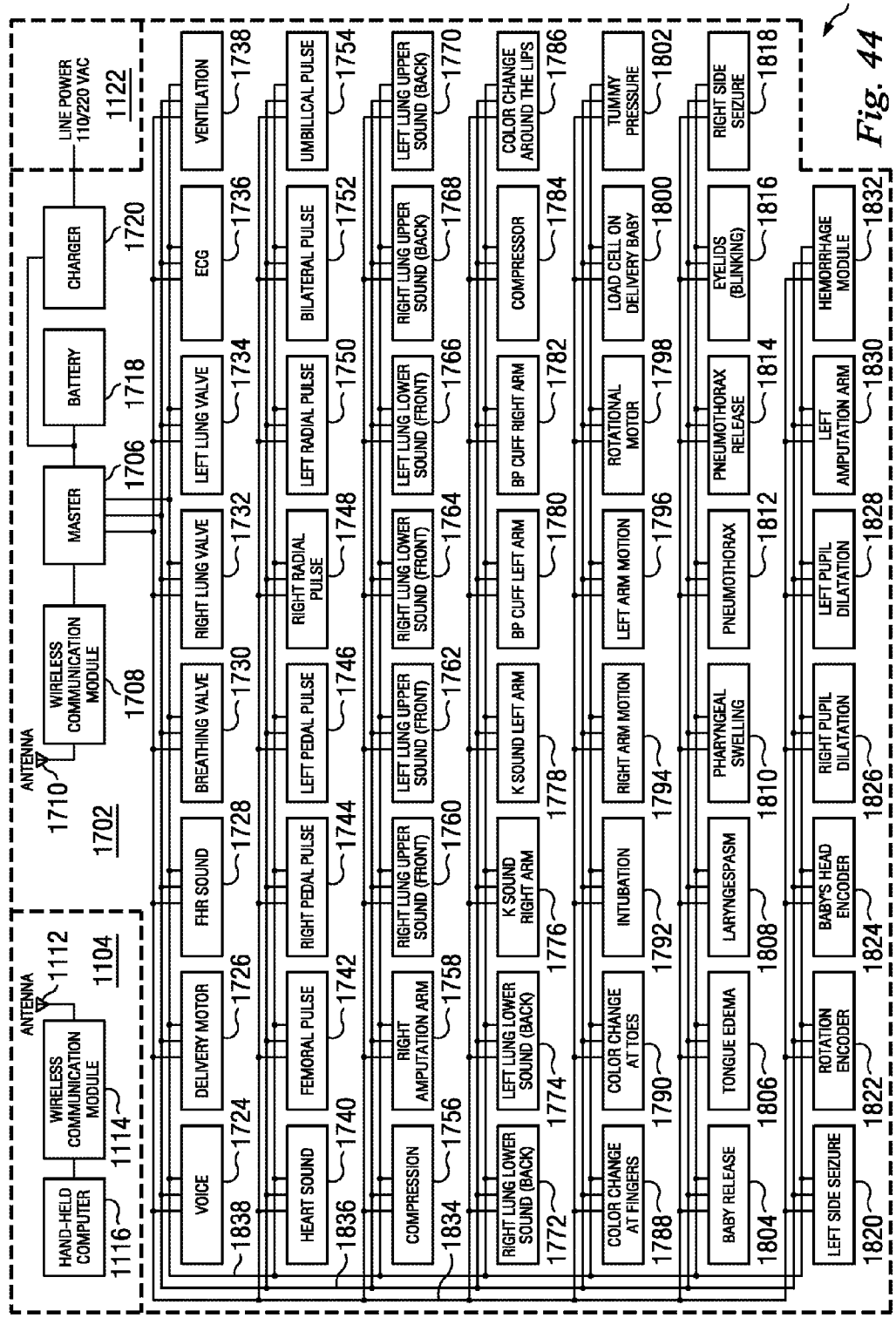
FIG. 44 is a diagrammatic schematic view of a patient simulator system according to one embodiment of the present disclosure.

Referring now to FIG. 44, shown therein is a diagrammatic schematic view of a patient simulator system 1700 according to one embodiment of the present disclosure. The patient simulator system 1700 includes a patient simulator 1702 and a control system 1104. The control system 1104 may be substantially similar to the control system described above with respect to FIG. 29. The patient simulator 1702 includes a plurality of modules for performing the various functions of the simulator. In some embodiments, each of the modules controls a particular function or group of functions of the simulator 1702. In that regard, the modules are appropriately sized for positioning within various portions of the simulator 1702. In some embodiments, the modules are positioned throughout the simulator adjacent to the region or area of the simulator 1702 related to the module's specific function or the associated body part of the simulator. Accordingly, the modules are distributed throughout the simulator rather than being grouped onto a single motherboard. In some embodiments, each of the modules is in communication with a master module 1706. In some embodiments the master module 1706 is configured to provide and control the power delivered to the modules and facilitate communication with and among the modules.

In the current embodiment, the patient simulator 1702 is in wireless communication with the control system 1104. In that regard, the patient simulator 1702 includes a wireless communication module 1708 and an antenna 1710. The wireless communication module 1708 and antenna 1710 are in communication with an antenna 1112 and a wireless communication module 1114 of the control system 1104. In the current embodiment the wireless communication module 1114 is connected to or in communication with a computer system 1116. In that regard, the computer system 1116 is a laptop or tablet PC in some instances. Generally, the computer system 1116, or the control system 1104 as a whole, is any combination of hardware and software capable of controlling or defining various factors and/or functions of the patient simulator 1702 through the master module 1706.

According to the present disclosure, various modules may be combined to create a simulator with specific features as desired by a customer or user. In this manner, some or all of the modules included in the patient simulator 1702 may be selected based on the intended use of the simulator. The modular nature of the modules allows the simulator 1702 to include the combination features that a customer desires initially, but also allows a customer to add additional features or disable included features later. One specific combination of available modules for use in the simulator 1702 will now be described. However, no limitation is intended thereby. In that regard, it is understood that simulators according to the present disclosure may include additional, fewer, or other combinations of modules. Various combinations of the modules are particularly suited for use in different types of patient simulators. Accordingly, in some embodiments a patient simulator system is created by combining modules having the desired features of the completed simulator. In some instances, the modules are configured for plug-n-play with the master module 1706 of the simulator 1702 such that modules may be added or removed as desired. Similarly, in some embodiments the control system 1104 is configured to activate or deactivate modules within the simulator 1702 as desired by a user. In some embodiments, the control system 1104 is configured to provide data regarding the modules present in the simulator, the modules available for use with the simulator but not present in the simulator, and/or the status (activated or not) of present modules.

The patient simulator 1702 includes a voice module 1724. The voice module 1724 is in communication with the master module 1706, which is in communication with the control system 1104. The voice module 1724 is an audio module configured to emit sounds simulating a patient's voice. In that regard, the particular sounds emitted by the voice module 1724 are controlled in some embodiments by a user through the control system 1104. In some embodiments, the control system 1104 includes a plurality of stored or prerecorded sounds that may be selected from and played back by the voice module 1724.

In some embodiments, the sounds include one or more of various answers to questions medical personnel might ask a patient and/or sounds a patient might make. For example, the answers may include various complaints (e.g., "ankle broken", "arm broken", "blood in toilet", "can't catch breath", "can't move", "can't move legs", "chest hurts", "coughing up blood", "elephant on chest", "feel dizzy", "feel nauseous", "feel weak", "heart beating fast", "heart pounding", "heart trying to jump", "hurt all over", "hurts when breathing", "I've been cut", "jaw hurts", "left arm hurts", "leg is broken", "passing blood", "peeing blood", "pooping blood", "puking blood", "short of breath", "shoulder hurts", "somebody shot me", "stomach hurts", "worst headache", and/or other complaints), confused answers (e.g., "Are you a doctor?", "I don't remember", "What happened?", "Who are you?", and/or other confused answers), location answers (e.g., "in my arm", "in my chest", "in my leg", "in my shoulder", "left side", "right side", and/or other location answers), descriptive answers (e.g., "a little bit", "a lot", "I can't move it", "it's dull", "it's sharp", "not pain . . . pressure", "pain in center chest", "sharp tearing pain", and/or other descriptive answers), evasive answers (e.g., "I feel fine", "take me to a hospital", and/or other evasive answers), generic answers (e.g., "yes", "no", "maybe", and/or other generic answers), history answers (e.g., "asthma", "diabetes", "emphysema", "had heart attack", "high blood pressure", and/or other history answers), occurrence answers (e.g., "once", "twice", "three times", "four times", "since last night", "since this morning", "since this afternoon", and/or other occurrence answers). In addition to the answers and responses noted above, the sounds include coughing, gagging, choking, moaning, screaming, and/or other sounds a patient makes. In that regard, each of the sounds may have different levels or types. For example, in some instances the sounds include different severity of coughs, gags, moaning, screaming, and/or other sounds.

In some embodiments, the control system 1104 is in communication with the voice module 1724 such that a user or teacher speaks into a microphone or other sound communication device associated with the control system and the teacher's words or sounds are emitted from the voice module 1724. In some embodiments, the user or teacher's input may be conditioned using audio amplifiers or sound boards to alter the sound of the voice emitted from the voice module 1724. For example, in some embodiments the input sound is conditioned to simulate a hoarse patient, a patient with a blocked air passage, or other mental or physical medical condition of the patient. In that regard, the teacher may selectively activate various types of audio conditioning based on a desired effect. The voice module 1724 and the corresponding voice simulation are utilized as part of an overall medical scenario simulation in some embodiments.

The patient simulator 1702 also includes a delivery motor module 1726. The delivery motor module 1726 is utilized to control the delivery of the fetus or baby from the simulator 1702 in embodiments where the simulator is a birthing simulator. In that regard, the delivery motor module 1726 is utilized to control the position of the baby within the mother simulator. Upon activation by the delivery motor module 1726, the delivery mechanism urges the baby out of the mother's womb. In some embodiments, the delivery mechanism will deliver the baby at least partially out of the mother's womb where the user completes delivery of the baby. In some embodiments, the delivery mechanism rotates the baby as it travels down the birth canal. Generally, the delivery motor module 1726 is configured to translate the baby along the birth canal. In that regard, the number of turns of the motor relative to a starting point is utilized to determine the precise translational position of the baby within the maternal simulator in some instances.

The patient simulator 1702 also includes a womb audio module 1728 to simulate the sounds of the fetus within the womb of the mother. For example, in some embodiments the womb audio module 1728 is an audio module configured to simulate the heart beat of the fetus within the womb. In that regard, the audio module produces a fetal heart sound as would be heard by someone using an ordinary stethoscope placed onto the mother's abdomen in an effort to hear the fetus's heart rate. In some embodiments, the fetal heart rate and its rates of change are synchronized with maternal contractions during a simulation. The phasing of changes in heart rate and contractions is used to assess the condition of the fetus in utero. Such phasing produces patterns that are evaluated to assess the condition of the fetus. The phasing patterns include periodic accelerations, late decelerations, and/or variable decelerations for example. In some embodiments, at a speaker of the womb audio module 1728 is located within the fetus and responds to commands from the Instructor through the master module 1706 located in maternal simulator. In some embodiments, the power and logic for the module 1728 are positioned adjacent the connection between the fetus and the birthing mechanism.

The patient simulator 1702 also includes a breathing valve 1730, a right lung valve 1732, and a left lung valve 1734. Together the breathing valve 1730, right lung valve 1732, and the left lung valve 1734 control the flow of air into and out of the lungs of the simulator 1702. In that regard, each of the valves 1730, 1732, and 1734 comprise a pneumatic valve. In some embodiments, the breathing valve 1730 is utilized to control the respiratory rate of the simulator 1702. In that regard, the breathing valve 1730 opens and closes in order for the lungs to inflate and deflate at the desired rate. The right lung valve 1732 and the left lung valve 1734 are utilized to selectively disable the right and/or left lungs, respectively. Accordingly, in some embodiments when the right lung valve is opened it closes a 3-way air pilot valve such that air cannot flow from the breathing valve into the right lung. In such instances, air flows from the breathing valve solely into the left lung. Factors such as disablement of the lungs, respiratory rate, respiratory pattern, inspiratory rate, and/or disablement of the left or right lung is controlled by the valves 1730, 1732, and 1734 based on signals received from the control system 1104 via the master module 1706.

The patient simulator 1702 also includes an ECG module 1736. The ECG module 1736 is configured to emit an electrical signal that simulates the electrical activity of the heart of the simulator 1702. In some embodiments, the ECG module 1736 is configured to provide signals associated with each of the 12 leads such that a 12-lead ECG signal is available to the user. In some embodiments, the ECG module 1736 is configured to emit signals that simulate the presence of a myocardial infarction in various parts of the heart. In some embodiments, the position of the myocardial infarction is selected via the control system 1104. Accordingly, the ECG module is utilized to train users to identify the onset of heart attacks and/or the associated symptoms identifiable via an ECG. The electrical signal of the ECG module is detectable by standard ECG equipment. Further, in some embodiments the ECG module 1736 is utilized in combination with a pacer/defib module. For example, in some instances the ECG module 1736 is used in combination with a pacer/defib module such as that described with respect to FIG. 40 above.

The patient simulator 1702 also includes a ventilation module 1738. The ventilation module 1738 is configured to monitor the use of a ventilation device applied to the simulator 1738. The ventilation device is a bag-valve mask in some instances. In other instances, the ventilation device is a user's mouth, such as in mouth-to-mouth resuscitation. The ventilation module 1738 is configured to monitor the pressure applied by the ventilation device and based on that pressure determine whether the pressure is too high, too low, or within the desired range. The ventilation module 1738 is in communication with the master module 1706, such that the determination of whether the correct pressure is being applied is relayed to the control system 1104. In some embodiments, the simulator 1702 will trend towards recovery or further complications based on whether the correct pressure is applied. For example, if the ventilation is within the desired range of pressures then the patient simulator may show signs of recovery. On the other hand, if the ventilation is outside the desired range of pressures then the patient simulator may develop additional problems or symptoms and/or make it more difficult to recover the simulator from the present symptoms.

The patient simulator 1702 also includes a heart sound module 1740. The heart sound module 1740 is an audio module configured to emit sounds to simulate the natural sounds of a patient's heart. In that regard, the sounds of the heart sound module 1740 include one or more of sounds to simulate the patient's heart rate and cardiac rhythm (e.g., sinus, atrial tachycardia, multifocal atrial tachycardia, atrial flutter, atrial fibrillation, junctional, idioventricular, ventricular tachycardia (uni.), ventricular tachycardia (multi.), supraventricular tachycardia, ventricular flutter, ventricular fibrillation, agonal, asystole, LBBB, RBBB, $1^{st}$ degree AVB, $2^{nd}$ degree AVB (Type I), $2^{nd}$ degree AVB (Type II), $3^{rd}$ degree AVB, Q-wave infarction, ST segment elevation, ST segment depression, T-wave inversion, atrial paced, AV sequential paced, vent. Pacemaker (artificial), and/or other cardiac rhythms). Further, the heart sounds may be normal, distant, non-existent, include a systolic murmur, S3, and/or S4. The control system 1104 and/or a user utilizing the control system determines what heart sounds and at what rate the sounds are produced in some embodiments. The sounds produced by the heart sound module 1740 are detectable via use of a stethoscope in some instances. In some embodiments, at least a portion of the heart sound module 1740—such as a speaker—is positioned within the simulator 1102 where the natural heart would be.

The patient simulator 1702 also includes a femoral pulse module 1742. The femoral pulse module 1742 is a pneumatic module for simulating the femoral pulse of the simulator 1702. The patient simulator 1702 also includes a right pedal pulse module 1744 and a left pedal pulse module 1746. The left and right pedal pulse modules 1744, 1746 are configured to simulate the pedal pulses in the feet of the simulator 1702. In that regard, in some embodiments the pedal pulse modules 1744, 1746 are electrical modules configured to simulate the pedal pulses. In other embodiments, the pedal pulse modules 1744, 1746 are pneumatic modules configured to simulate the pedal pulses. The patient simulator 1702 also includes a right radial pulse module 1748 and a left radial pulse module 1750. The right and left radial pulse modules 1748, 1750 are pneumatic modules for simulating the radial pulses of the simulator 1702. The patient simulator 1702 also includes a bilateral pulse module 1752 for simulating the bilateral pulse of the simulator. The patient simulator 1702 also includes an umbilical pulse module 1754 for simulating the umbilical pulse between a maternal simulator and associate fetal simulator.

The patient simulator 1702 also includes a compression module 1756. The compression module 1756 is configured to monitor the force of chest compressions applied to the simulator 1702. In that regard, the compression module 1756 is configured to monitor the pressure applied and based on that pressure determine whether the pressure is too high, too low, or within the desired range. The compression module 1756 is in communication with the master module 1706, such that the determination of whether the correct pressure is being applied is relayed to the control system 1704. In some embodiments, the simulator 1702 will trend towards recovery or further complications based on whether the correct pressure is applied. For example, if the chest compressions are within the desired range of pressures then the patient simulator may show signs of recovery. On the other hand, if the chest compressions are outside the desired range of pressures then the patient simulator may develop additional problems or symptoms and/or make it more difficult to recover the simulator from the present symptoms.

The patient simulator 1702 also includes a right amputation arm module 1758 and a left amputation arm module

1830. The amputation arm modules 1758 and 1830 are configured to work with an arm that simulates a severed arm, as might be seen in a war zone or car accident. In other embodiments, the patient simulator 1702 includes similar amputation modules for use with severed legs. The amputation modules 1758 and 1830 are configured to spurt simulated blood as a function of the selected heart rate and blood pressure of the simulator 1702. The arm of the simulator 1702 contains a bladder that is filled with the simulated blood. The amputation modules 1758 and 1830 include connections for pneumatic pressure and electrical power. The power selectively activates a pneumatic valve to start/stop bleeding as a function of the simulator's heart rate. The strength or amount of the arterial spurting is controlled by selecting the length of the time the valve is open and/or by selecting the pressure in the line connected to the bladder. The longer the valve is open and the greater the pressure, the more blood will spurt from the arm. The bleeding can be stopped by the application of a conventional tourniquet to severed arm. In some embodiments, a flexible tube is positioned under the skin of the simulator in the area where a tourniquet should be placed. If a user properly places the tourniquet then the flexible tube will be closed and the bleeding stops. However, if the tourniquet is not properly positioned or positioned property but without sufficient tension to close the tube, then the simulator 1702 continues to bleed.

The patient simulator 1702 also includes lung sound modules 1760, 1762, 1764, 1766, 1768, 1770, 1772, and 1774. In particular, lung sound module 1760 is utilized to simulate sounds of the upper right lung towards the front of the simulator 1702; lung sound module 1762 is utilized to simulate sounds of the upper left lung towards the front of the simulator; lung sound module 1764 is utilized to simulate sounds of the lower right lung towards the front of the simulator; lung sound module 1766 is utilized to simulate sounds of the lower left lung towards the front of the simulator; lung sound module 1768 is utilized to simulate sounds of the upper right lung towards the back of the simulator; lung sound module 1770 is utilized to simulate sounds of the upper left lung towards the back of the simulator; lung sound module 1772 is utilized to simulate sounds of the lower right lung towards the back of the simulator; lung sound module 1774 is utilized to simulate sounds of the lower left lung towards the front of the simulator.

Each of the lung sound modules 1760, 1762, 1764, 1766, 1768, 1770, 1772, and 1774 is an audio module configured to produce sounds to simulate the natural sounds of a patient's lungs. In that regard, the lung sound modules 1760, 1762, 1764, 1766, 1768, 1770, 1772, and 1774 are configured to produce one or more of the following lung sounds in some embodiments: normal, none, wheezing, inspiration squeaks, crackles, rails, and/or other lung sounds. Further, the combination of lung sound modules 1760, 1762, 1764, 1766, 1768, 1770, 1772, and 1774 are utilized to simulate respiratory patterns including, but not limited to normal, Kussmaul's, Cheyne-Stokes, Biot's, apneusic, and/or other respiratory patterns. The combination of lung sound modules 1760, 1762, 1764, 1766, 1768, 1770, 1772, and 1774 are also utilized to simulate the respiratory rate of the patient. In that regard, the respiratory rate may be set at a constant rate and/or be set to change over time.

The patient simulator 1102 also includes a K-sound module 1776 for the right arm of the simulator and a K-sound module 1778 for the left arm of the simulator. Each of the K-sound modules 1776 and 1778 are configured to produce a simulated K-sound (Korotkoff sound). In that regard, the K-sound modules 1776 and 1778 are utilized to allow a user to take the blood pressure of the patient simulator 1702 in some embodiments. In that regard, the K-sound modules 1776 and 1778 are configured to produce the associated K-sounds when a user is taking the blood pressure of the simulator 1702. In some embodiments, the determination of what K-sounds are to be produced is at least partially determined by the pressure measurements of a blood pressure cuff module of the simulator 1702. Further, the K-sounds produced by the modules 1776 and 1778 are determined based on a simulated heart rate and blood pressure. In some instances, the heart rate and blood pressure of the patient simulator 1702 are provided by a user or teacher via the control system 1104.

The patient simulator 1702 also includes a left blood pressure cuff module 1780 and a right blood pressure cuff module 1782. The left and right blood pressure cuff modules 1780 and 1782 are pressure modules configured to allow a user to take a simulated blood pressure of the patient simulator 1702. The blood pressure cuff modules 1780 and 1782 are configured for use with standard blood pressure monitors in some embodiments.

The patient simulator 1702 also includes a compressor module 1784. The compressor module 1784 is configured to control a compressor of the simulator 1702. The compressor is utilized to provide a compressed air supply to the various pneumatic devices of the simulator 1702. For example, in some embodiments the compressor is utilized to provide air to modules for simulating the lungs, pulses, contractions, tummy pressure, seizures, eye dilation, blinking, and/or other aspects of the patient simulator 1702. In some embodiments, the compressor provides pressurized air to one or more air reservoirs or accumulators that are then connected to the various pneumatic modules of the simulator 1702. In that regard, the air reservoirs may maintain different air pressures such that different pneumatic modules are connected to the air reservoir with the appropriate air pressure for its application. In some instances, the pneumatic modules of the patient simulator 1702 that utilize the compressor are configured to run at a relatively low air pressure, e.g., less than 10 psi in some embodiments and less than 5 psi in other embodiments. In some instances, the simulator 1702 includes two accumulators with one of the accumulators maintaining an air pressure of approximately 5 psi and the other accumulator maintaining an air pressure of approximately 1 psi. In other embodiments, the accumulators maintain other air pressures. Generally, however, the patient simulator 1702 and its associated components are configured to operate at low pressures, which helps prevent the introduction of water into the simulator associated with high pressure systems. The introduction of water into the simulator that results from using high pressure systems can cause damage to the simulator, increase the maintenance costs, and require additional components to remove or limit the amount of water within the simulator.

Further, the compressor is sized to fit entirely within the simulator 1702. In that regard, the compressor operates quietly so as not to interfere with the other simulation aspects of the simulator 1702. Accordingly, in some instances a muffler system is utilized to minimize the noise generated by the compressor. The muffler system is utilized on the input, output, and/or both sides of the compressor in some embodiments. Further, the compressor is self-cooling in some instances. In one such embodiment, the compressor includes a plurality of metal pipes surrounding at least the compressor motor that intake air is passed through. The intake air passing through the metal pipes helps to dissipate the heat generated by the compressor. Accordingly, the compressor is able to operate entirely within the simulator 1702 without overheating or disturbing the other simulation aspects of the simulator. This allows the simulator 1702 to be fully functional without attachment to a noisy, external, high pressure compressor.

The patient simulator 1702 also includes a plurality of color change modules 1786, 1788, and 1790. In that regard, the color change module 1786 is configured for controlling color change around the lips of the simulator 1702; the color change module 1788 is configured for controlling color change around the fingers of the simulator; and the color change module 1790 is configured for controlling color change around the toes of the simulator. The color change modules 1786, 1788, and 1790 are utilized in some embodiments to simulate cyanosis of the patient simulator. Accordingly, the color change modules 1786, 1788, and 1790 are configured to simulate different levels of cyanosis of the patient simulator 1702. In that regard, the degree of cyanosis is determined by the control system 1104 and/or a user of the control system 1104 in some embodiments. The degree of cyanosis may trend—increase and/or decrease—based on a variety of parameters including the efficacy of any treatments administered. In some embodiments, the trending is controlled manually via the control system 1104. In other embodiments, the trending is at least partially controlled by a physiological simulator software application of the control system 1104.

The patient simulator 1702 also includes an intubation module 1792. The intubation module 1792 is configured to monitor intubation of the patient simulator 1702. In that regard, the depth of proper intubation for the patient simulator 1702 will depend on the size and/or age of the patient simulator. In that regard, the intubation module 1792 is associated with a particular size of patient simulator to determine the proper intubation depth. In some embodiments, the intubation module 1792 utilizes an optical sensor to monitor the depth of an intubation tube within the trachea of the patient simulator 1702. In some embodiments, the intubation module 1792 utilizes a pair of optical sensors spaced apart from one another to define the acceptable range of intubation depths. The first optical sensor is utilized to detect the presence of an intubation tube as it reaches the beginning of the acceptable range of depths. The second optical sensor is utilized to detect when the intubation tube has been advanced beyond the acceptable range of depths.

The patient simulator 1702 also includes a right arm motion module 1794 and a left arm motion module 1796. The right and left arm motion modules 1794 and 1796 are configured to activate movement of the left and right arms of the simulator 1702. In some embodiments, the right and left arm modules 1794 and 1796 are particularly suited for use in a newborn sized simulator. In some embodiments, the right and left arm motion modules 1794 and 1796 comprise pneumatic modules that are utilized to inflate and deflate air bags associated with the arms of the simulator. In that regard, in some instances the air bags comprise accordion bags such that as the bags are filled with air they expand outwardly in a predetermined profile. By inflating and deflating the bags with the modules, the arms of the simulator are moved. The bags are associated with a pivot assembly positioned adjacent the simulator's elbow in some instances. In one particular embodiment, inflation and deflation of the bags causes the simulator's arm to bend or straighten via the pivot assembly. As movement of the arms is actuated by a pneumatic module and the inflation and deflation of air bags, a user can restrain movement of the arms without causing physical damage to the simulator in contrast to some mechanically actuated systems. In some embodiments, the arm motion modules are configured to activate a mechanical system or motor for moving the simulator's arms. In some embodiments, the mechanical system includes a safety to prevent damage to the arm motion modules and associated components if and when the intended arm motion is restricted by a user.

The patient simulator 1702 also includes a rotation module 1798. The rotation module 1798 is configured to rotate the fetus or baby within the mother simulator. Particularly, the rotation module 1798 is configured to actuate a motor or other device for controlling the rotation of the baby as it travels within the birth canal of the mother simulator. The patient simulator 1702 also includes a load cell module 180. In some embodiments, the load cell module 1800 is positioned on a delivery mechanism of the mother simulator and is configured to monitor the amount of pressure being exerted on the baby during birthing. In that regard, the load cell module 1800 is positioned adjacent the attachment point of the baby to the delivery mechanism in some embodiments. In other embodiments, the load cell module 1800 is positioned within or on the baby itself. Generally, the signals generated by the load cell are communicated to the control system 1104 via the master module 1706. Based on the sensed pressures or forces as measured by the load cell, a determination can be made regarding whether the amount of force being used in birthing the baby are within the desired range.

The patient simulator 1702 also includes a tummy pressure module 1802. The tummy pressure module 1802 is utilized to control the firmness of the mother simulator's tummy. In that regard, the tummy pressure module 1802 is configured to sense the amount of pressure within the mother's tummy. Based on a desired pressure, the tummy pressure module 1802 determines whether pressure in the tummy should be increased, decreased, or remain the same. If the pressure should be increased, then the tummy pressure module 1802 activates the flow of air to the tummy through a pneumatic valve. In some embodiments, the tummy pressure module 1802 is in communication with an air reservoir or compressor for providing the air flow to the tummy. If the pressure should be decreased, then the tummy pressure module 1802 activates the release of air from the tummy. The desired pressure is provided by the control system 1104 in some instances. In that regard, a user or teacher can define the tummy pressure via the control system 1104 in some embodiments.

The patient simulator 1702 also includes a baby release module 1804. The baby release module 1804 is configured to selectively release the baby from the delivery mechanism within the maternal simulator. In that regard, the baby release module 1804 is remotely activated by a user or teacher via the control system 1104 in some instances. In other instances, the baby release module 1804 is activated based on the position of the delivery mechanism and/or baby within the birth canal. That is, once the baby reaches a certain position and/or orientation with the birth canal the baby release module activates to release the engagement between the delivery mechanism and the baby.

The patient simulator 1702 also includes a tongue control module 1806. The tongue control module 1806 is a pneumatic module configured to selectively inflate and/or deflate the tongue to partially obstruct an airway of the simulator 1702. In that regard, the tongue control module 1806 is controlled via the control system 1104 in some instances.

Accordingly, a user or teacher can partially block or unblock the airway as desired. The patient simulator 1702 also includes a larynges control module 1808 and a pharynges control module 1810. The larynges control module 1214 is configured to open and close the larynx to partially obstruct the airway of the simulator, to simulate a laryngespasm. Similarly, the pharynges control module 1216 is configured to urge the posterior wall of the pharynx anteriorly to partially obstruct the airway of the simulator, to simulate pharyngeal swelling. The larynges control module 1808 and the pharynges control module 1810 are also controlled via the control system 1104 in some instances. Accordingly, a user or teacher can also partially block or unblock the airway as desired with these features as well.

The patient simulator 1702 also includes a pneumothorax module 1812 and a pneumothorax release module 1814. The pneumothorax module 1812 is configured to simulate the presence of a pneumothorax (collapsed lung) in the left lung or the right lung. The pneumothorax release module 1814 is configured to return the simulator 1702 to normal lung condition without a pneumothorax. The onset and alleviation of the pneumothorax condition is controlled via the control system 1104.

The patient simulator 1702 also includes eyelid module 1816. The eyelid module 1816 is configured to control the blinking of the patient's eyes. In some embodiments, the eyelid module 1816 includes modules for controlling the opening and closing of the eyelids to simulate blinking. Similarly, the rate, pattern, and speed of blinking are controlled by the control system 1104 in some instances. In some instances the rate of blinking ranges from 5 blinks per minute to 30 blinks per minute. However, ranges outside of this are used in some embodiments. Further, the eyes can be maintained in an open position or a closed position. The speed of the blinks can be controlled as well. In some instances, the speed of each blink from open to closed to open is approximately 200 ms. However, the speed of the blinks can be increased or decreased as desired in some embodiments.

The patient simulator 1702 also includes a right side seizure module 1818 and a left side seizure module 1820. The right and left seizure modules 1818 and 1820 are configured to simulate a seizure of the patient on the corresponding sides of the patient's body. Accordingly, the seizure modules 1818 and 1820 are configured to cause shaking and/or convulsing in some embodiments. Also, the seizure modules 1818 and 1820 are used together in some instances to simulate a full body seizure. In some instances activation of the seizure modules 1818 and 1820 is controlled via the control system 1104.

The patient simulator 1702 also includes a rotational encoder module 1822 and a head encoder module 1824. The rotational encoder module 1822 and the head encoder module 1824 are configured to provide rotational positional data regarding the baby within the birthing canal of a maternal simulator. In that regard, the rotational encoder module 1822 and head encoder module 1824 are particularly configured to monitor the relative rotation of the baby within the birth canal. In some embodiments, the rotational encoder module 1822 is positioned on the delivery mechanism of the maternal simulator and the head encoder module 1824 is positioned within a portion of the baby. In some instances, the head encoder module 1824 is positioned within the head of the baby. The rotation of the baby is determined by comparing the relative rotation of the head encoder module 1824 on the baby to the rotational encoder module 1822. In some instances, the rotational encoder module 1822 is substantially fixed rotationally. Based on the relative rotation of the module 1824 compared to the module 1822 the rotational position of the baby can be determined. In some embodiments the modules 1822 and 1824 are optical modules. The rotational data from the modules 1822 and 1824 is communicated to the control system 1104 in some embodiments. In one such embodiment, a user or teacher utilizes the positional and rotational information to determine when to release the baby from the delivery mechanism of the maternal simulator. In other embodiments, the control system 1104 automatically releases the baby from the delivery mechanism based on a correct orientation and position of the baby within the birth canal.

The simulator 1702 also includes a right pupil dilation module 1826 and a left pupil dilation module 1828. In some embodiments, the pupil dilation modules 1826 and 1828 control the dilation of each of the simulator's eyes at least partially based on the amount of light received by an optical sensor positioned within the eye. The maximum size of the pupil and/or the rate of change or dilation of the pupil are controlled by the control system 1104 in some instances.

The patient simulator 1702 also includes a hemorrhage module 1832. In some embodiments the hemorrhage module 1832 is configured for use in maternal simulator. In that regard, hemorrhaging is a leading cause of maternal death. Although it is not unusual for a woman to lose 500 cc of blood during or after delivery of the baby, the loss of more than a liter of blood can lead to shock and ultimately death. The patient simulator is equipped with a reservoir containing simulated blood from which the simulated blood can be pumped to simulate hemorrhaging. In that regard, the hemorrhaging module works in a manner substantially similar to the right and left arm amputation modules 1758 and 1830 described above. In maternal simulator applications, the amount of bleeding and its flow rate are controlled via a flexible tube positioned between the reservoir and the birth canal. A user can stop the bleeding by applying appropriate pressure to deform the tubing and cutoff the flow of simulated blood.

Each of the various modules is connected to the master module 1706 via a power wire 1834, a ground wire 1836, and a 2-way communication wire 1838. In that regard, the master module 1706 can control the activation, deactivation, and power consumption of each of the modules. In some embodiments, the master module 1706 is controlled via a software program of the control system 1104. In other embodiments, the modules are directly connected to a power supply. In some embodiments, the master module 1706 is in wireless communication with one or more of the modules. In some embodiments, communication to one or more of the modules is 1-way communication. In some embodiments, the modules themselves are interconnected via the communication wire 1838 or an additional communication wire. In that regard, in some instances a non-master module acts as a master module for a subset of modules.

In some embodiments the patient simulators of the present disclosure are configured for physiological simulation. In that regard, in some embodiments an external control system or other software-based interface is configured to adjust the various physical parameters of the patient simulator based on a physiological simulation protocol. In some embodiments, the external control system includes a plurality of models including but not limited to a circulation model, respiratory model, myocardial infarction model, medication/pharmaceutical model, mother/fetus model, and/or other physiological models for controlling the simulated physical parameters. The physiological models are configured for simulating various physiological situations and medical conditions, such as heart attacks, decreased oxygen supply, and any other desired medical conditions that may be simulated by the associated patient simulator. Several specific embodiments of physiological simulation and physiological simulation models will now be described.

In one embodiment, physiological simulation is utilized with a maternal simulator and a fetal simulator. For example, in some embodiments the effect of an abnormal physical condition of the maternal simulator on the fetal simulator is simulated by changing the physical characteristics of the fetal simulator. Further, this effect is maintained or established in the newborn simulator after the simulated birth of the fetal simulator. In some instances, a maternal/fetal model generates a number of physiological outputs defining the physical characteristics of the maternal simulator and the fetal simulator. These physiological outputs are received by a master module of the simulators and the corresponding physical characteristics are then simulated. In some instances the physiological outputs include the maternal blood oxygenation. The level of maternal blood oxygenation relates to the fetal heart rate and how changes in fetal heart rate correspond to contractions of the maternal simulator. High levels of oxygenation relate to normal fetal heart rates and reassuring patterns of fetal heart tones. However, low levels of oxygenation relate to low heart rates and ominous patterns, such as variable decelerations. Further, the maternal blood oxygenation also relates to the level of oxygenation of the fetus. In particular, a low maternal blood oxygenation level signals that the fetus will be receiving a low amount of oxygen through the placenta. The level of fetal oxygenation relates to the well being of the newborn. A fetus that is well oxygenated throughout the delivery process usually exhibits good posture, good muscle tone, a heartrate in excess of 100 beats a minute, good color, and good breathing as a newborn. These 5 elements—posture, muscle tone, heart rate, color, and breathing—are used to estimate the APGAR score for a newborn. The APGAR score is normally determined 1 minute after birth, 5 minutes after birth, and if necessary at five minute intervals thereafter.

Accordingly, the maternal/fetal model provides physiological outputs that correlate the physical parameters of the maternal and fetal simulators to one another. In addition, characteristics of the fetal simulator are carried on to the newborn in some instances. The newborn is designed to exhibit these physical characteristics and, in some embodiments, can simulate a newborn exhibiting an APGAR score from 0 to 10. In this manner, the maternal simulator's wellbeing is transferred to the fetal simulator which is then transferred to the neonate. In that regard, in some embodiments the fetal simulator and the newborn or neonatal simulator are the same simulator. In other embodiments, the fetal simulator and the newborn simulator are separate simulators.

In addition to correlating the physical parameters of the maternal and fetal simulators to one another, the physiological modeling is also configured to correlate physical parameters within a single simulator. For example, in some embodiments the physical parameters of the simulator are adjusted based on the treatment provided to the simulator by a user. If the appropriate treatment is provided, then the physical parameters of the simulator improve. However, if the treatment is not adequate, then the physical parameters of the simulator stay the same or get worse. The particular interaction between the treatment and the physical parameters of the simulator are driven by the physiological model.

In that regard, in some instances the physiological model utilizes data received from the modules within the simulator to determine whether the treatment is appropriate. For example, the amount of pressure as sensed by a chest compression module or a ventilation module is utilized in some instances to determine whether the level of treatment is appropriate. Further, in some embodiments the physical parameters of the simulator are extended from one area of the simulator to another. For example, in some instances the respiratory system of the simulator indicates that the simulator has low oxygenation and if this problem is not adequately addressed through appropriate treatment, then the respiratory problem is extended to a problem in the simulated circulatory system. In that regard, the various physiological models are in communication with one another in some instances. The specific interactions between the various portions of the simulator are defined according to the natural physiological interactions within the body in some instances. In some instances, these interactions are defined at least partially based on medical studies and/or published papers regarding such interactions.

In some embodiments, the physiological modeling includes a circulation model. The circulation model is configured to control the simulated physical parameters of the circulatory system of the patient simulator. In that regard, the circulation model controls the blood pressure, heart rate, blood oxygenation, K-sounds, and/or other parameters of the circulatory system. In some instances, the circulation model controls the physical parameters within various compartments or regions of the patient simulator. In that regard, in some instances the circulatory system is divided into a plurality of regions, including but not limited to the 4 chambers of the heart. Further, in some embodiments the physiological modeling includes a myocardial infarction model. In some instances, the myocardial infarction model is part of the circulatory model. The myocardial infarction model is configured to control aspects of the circulatory system associated with a heart attack, including but not limited to the supply of oxygen to the heart. In some instances, the myocardial infarction model controls the specific location of the myocardial infarction. Further, in some instances the myocardial infarction model controls the ECG module of the patient simulator such that the ECG module emits electrical signals corresponding to the myocardial infarction, including but not limited to the location and/or severity of the problem.

In some embodiments, the physiological modeling includes a respiratory model. The respiratory model is configured to control the simulated parameters of the respiratory system of the patient simulator. In that regard, the respiratory model controls the respiratory rate, inspiration rate, lung sounds, $O_2/CO_2$ mixture, and/or other parameters of the respiratory system. In some embodiments, the physiological modeling includes a medicinal or pharmaceutical model. In some instances the pharmaceutical model is configured to integrate with other models and/or modules to modify the simulated parameters of the patient simulator based on the effects associated with introducing a pharmaceutical to the patient. In that regard, in some instances the pharmaceutical model maintains a database of the physical effects associated with a particular pharmaceutical. Accordingly, the pharmaceutical model trends or adjusts the parameters of the patient simulator based on the effects of the pharmaceutical. The rate of change of the parameters is based on the effects of the pharmaceutical in some instances. In some instances, the pharmaceutical model allows a user to define the effects of the pharmaceutical.

In some embodiments, the physiological modeling comprises a plurality of scenarios. In that regard, each scenario is defined by a particular grouping or sets of parameters. In some instances the scenario includes particular circulatory and respiratory parameters associated with a medical problem. Accordingly, a scenario integrates the features of the various physiological models in some instances. In some embodiments, the physiological modeling is configured to trend between scenarios. In that regard, a user or teacher establishes a predetermined series of scenarios. The user defines the length of time for each scenario and the amount of transition time between scenarios in some embodiments. In some embodiments, the series of scenarios is at least partially modified based on the treatment administered to the patient simulator. In that regard, the parameters of the patient simulator improve or decline at least in part based on the treatment administered. In some embodiments, at least some of the scenarios are predefined or provided by the physiological simulation models. In some embodiments, at least some of the scenarios are user defined. That is, a user can associate a plurality of parameters and define a scenario. Further, a user can associate plurality of scenarios—predefined or user defined—as an additional scenario.

Figure 45:
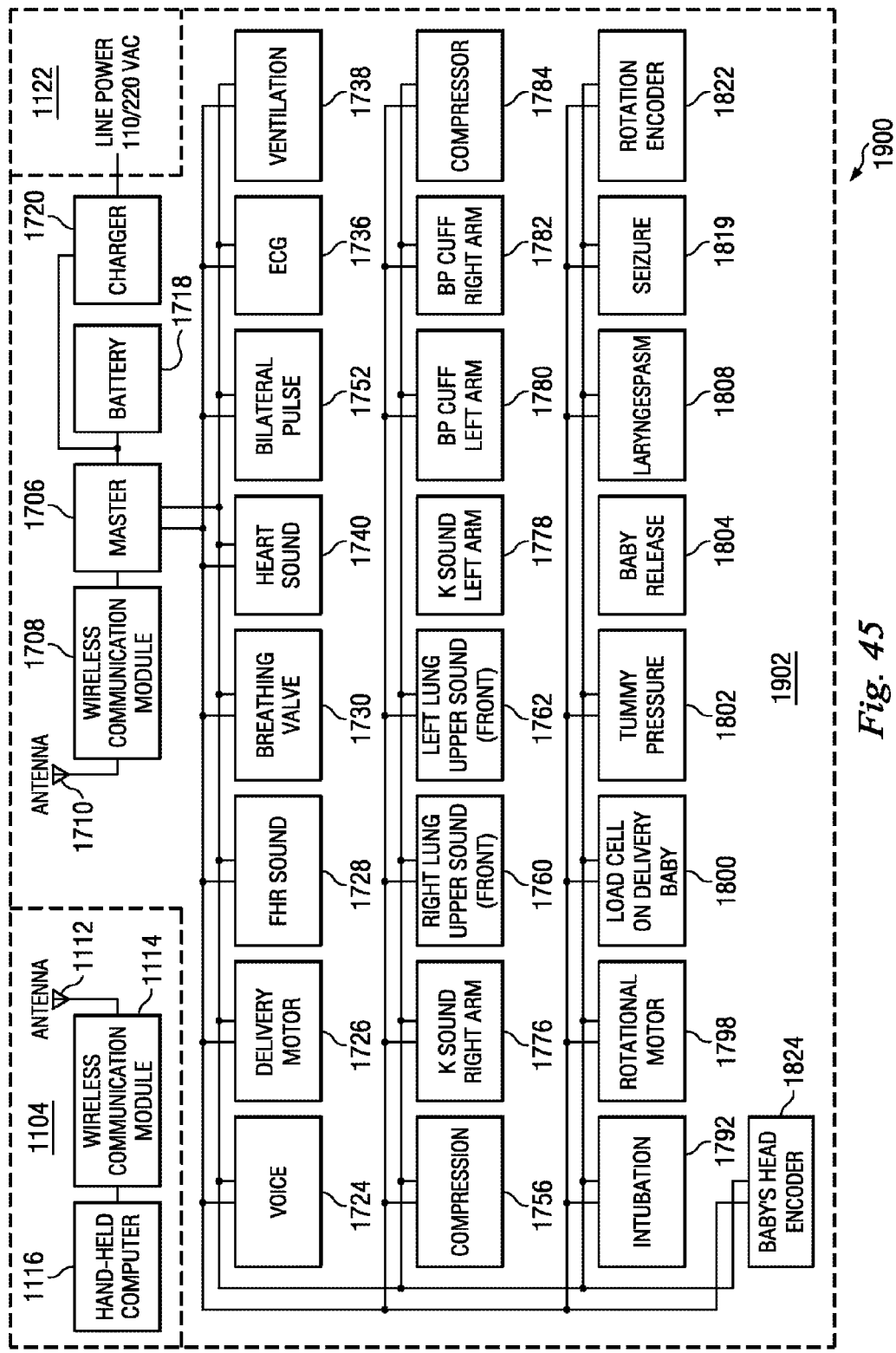
FIG. 45 is a diagrammatic schematic view of a patient simulator system according to another embodiment of the present disclosure.

Referring now to FIG. 45, shown therein is a diagrammatic schematic view of a patient simulator system 1900 according to one embodiment of the present disclosure. In particular, the system 1900 includes a patient simulator 1902 including a plurality of modules particularly suited for birthing simulation. In that regard, the simulator 1902 includes a combination of select modules described with respect to FIG. 44 above. In that regard, the patient simulator 1902 includes the master module 1706, communication module 1708, antenna 1710, battery 1718, and charger 1720. In addition to these components, the simulator 1902 includes the voice module 1724, the delivery module 1726, the FHR sound module 1728, breathing valve module 1728, heart sound module 1740, bilateral pulse module 1752, ECG module 1736, ventilation module 1738, compression module 1756, K-sound modules 1776 and 1778, lung sound modules 1760 and 1762, blood pressure cuff modules 1780 and 1782, compressor control module 1784, intubation module 1798, rotational module 1798, load cell module 1800, tummy module 1802, release module 1804, larynges module 1808, seizure module 1819 (a combination of left and right seizure modules 1818 and 1820 in some embodiments), rotational encoder module 1822, and head encoder module 1824.

Figure 46:
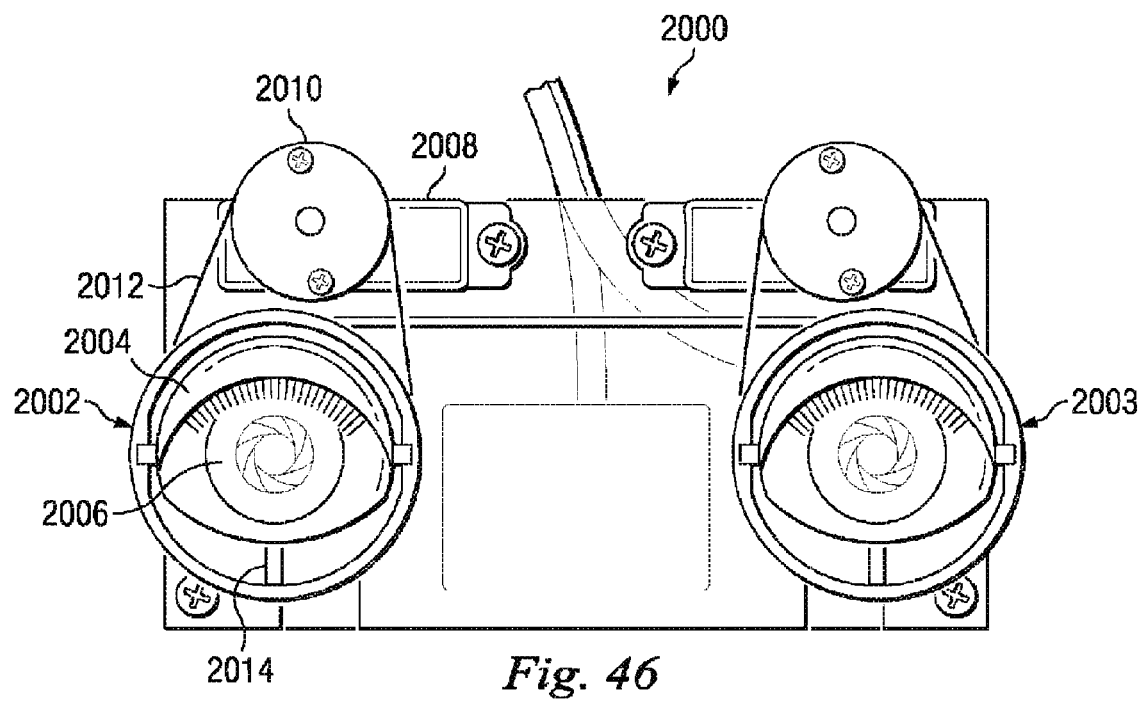
FIG. 46 is a front view of an eye assembly for use in a patient simulator according to one embodiment of the present disclosure.
Figure 47:
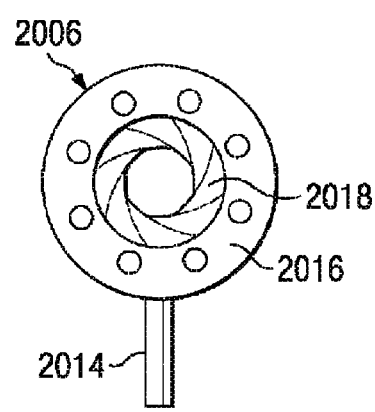
FIG. 47 is a front view of an iris diaphragm of the eye assembly of FIG. 46 according to one embodiment of the present disclosure.
Figure 48:
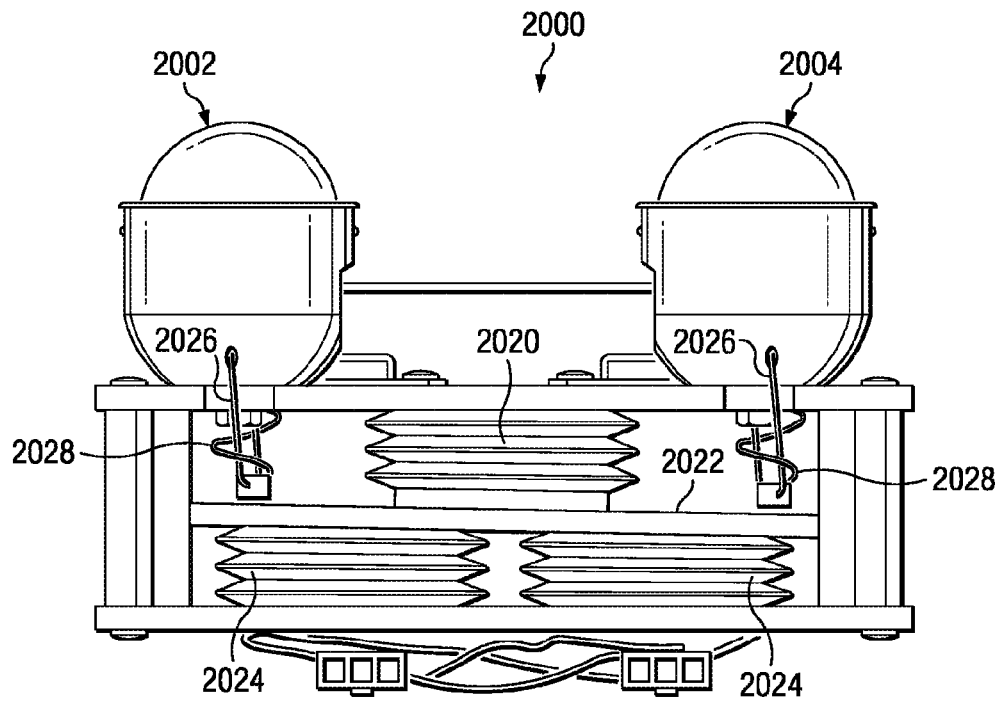
FIG. 48 is a bottom view of the eye assembly of FIG. 46.
Figure 49:
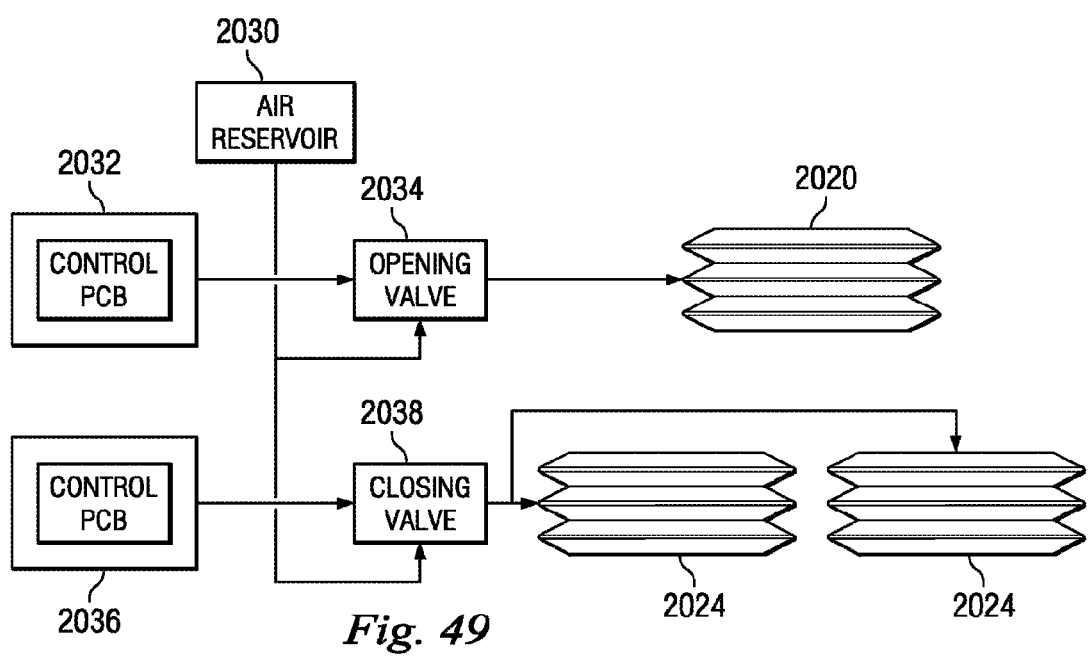
FIG. 49 is a diagrammatic schematic view of the blinking assembly of the eye assembly of FIG. 46.

Referring now to FIGS. 46-49, shown therein is an eye assembly 2000 according to one embodiment of the present disclosure. In particular, FIG. 46 is a front view of the eye assembly 2000; FIG. 47 is a front view of an iris diaphragm of the eye assembly 2000; FIG. 48 is a bottom view of the eye assembly 2000; and FIG. 49 is a diagrammatic schematic view of the blinking assembly of the eye assembly 2000. Referring more specifically to FIG. 46, the eye assembly 2000 includes a left eye 2002 and a right eye 2003. The left and right eyes 2002 and 2003 are sized, shaped, and colored to simulate a natural patient's eyes. In that regard, the eyes 2002, 2003 include eyelids 2004 and a simulated iris assembly 2006 that is configured to dilate in a similar manner to a natural eye. In that regard, in some embodiments the diameter of the pupils is adjustable from 1 mm to 8 mm. In some instances, the maximum diameter of the pupils is established by a control system in communication with the eye assembly 2000. In that regard, a user or teacher is able to set the pupil size in some embodiments via the control system.

The eye assembly 2000 includes a servo motor 2008 that is in communication with or directly connected to a wheel 2010. The wheel 2010 in turn is in communication with or directly connected to a microfilament line 2012 that is communication with or directly connected to the iris assembly 2006. In particular, the microfilament line 2012 is in communication with or directly connected to a pin 2014 of the iris assembly 2006. Referring more particularly to FIG. 47, the pin 2014 is moveable relative to an outer portion 2016 of the iris assembly 2006 such that an inner portion 2018 expands and contracts radially with corresponding movement of the pin 2014. In some embodiments, the pin 2014 moves left or right around the outside of the outer portion 2016 as shown in FIG. 47 to adjust the size of the visible portion of the inner portion 2018.

In some embodiments, the eye assembly 2000 includes an optical sensor that is associated with each eye 2002 and 2003. Based on the amount of light received by the optical sensor the servo motor 2008 is activated to increase or decrease the amount of the inner portion of the iris assembly that is visible. The greater the amount of the inner portion 2018 that is visible, the smaller the simulated pupil of the eye. Similarly, the lesser the amount of the inner portion 2018 that is visible, the larger the simulated pupil of the eye will appear. In this manner, pupil dilation is simulated by the eye assembly 2000. In some instances, the rate of change or responsiveness of the iris assembly can be slowed to simulate an abnormal medical condition that would result in slowed pupil dilation.

Referring more particularly to FIGS. 48 and 49, the eye assembly 2000 configured to simulate blinking of the patient. In particular, the eyelids 2004 of the eyes 2002 and 2003 are opened and closed to simulate blinking. In the present embodiment, the eye assembly 2000 utilizes a pneumatic system to simulate the blinking of the eyes. In particular, the eye assembly 2000 includes an opening bag 2020, a middle plate 2022, and closing bags 2024. The middle plate 2022 is connected to the eyelids 2004 via followers 2026 such that, as the middle plate translates due to the inflation and deflation of the bags 2020 and 2024, the eyelids open and close. A spring 2028 is also included in some embodiments to facilitate faster closing and opening of the eyelids 2004. When the opening bag 2020 is inflated the middle plate 2022 is forced away from the eyes and the eyelids 2004 are held open. When the closing bags 2024 are inflated the middle plate 2022 is forced towards the eyes and the eyelids 2004 of the eyes are closed. Accordingly, the bags 2020 and 2024 can be activated in sequence to simulate blinking.

Referring more specifically to FIG. 49, shown therein is a schematic of the blinking assembly of the eye assembly 2000. In that regard, the blinking assembly is in communication with an air reservoir or compressor 2030 for inflating the bags 2020 and 2024. In that regard, a control board 2032 controls the opening and closing of a valve 2034 associated with the opening bag 2020. Similarly, a control board 2036 controls the opening and closing of a valve 2038 associated with the closing bags 2024. In some embodiments the control boards 2032 and 2036 are in communication with or directly connected to a master module of the simulator. In such embodiments, the master module directs the control boards 2032 and 2036 when to open and close the valves 2034 and 2038 respectively. In some embodiments the rate, pattern, and/or speed of blinking are controlled by a control system in communication with the master module. In some instances the rate of blinking ranges from 5 blinks per minute to 30 blinks per minute. However, ranges outside of this are used in some embodiments. Further, the eyelids 2004 can be maintained in an open position or a closed position if desired. The speed of the blinks can be controlled as well. In some instances, the speed of each blink from open to closed and back to open is approximately 200 ms. However, the speed of the blinks can be increased or decreased as desired in some embodiments.

Figure 50:
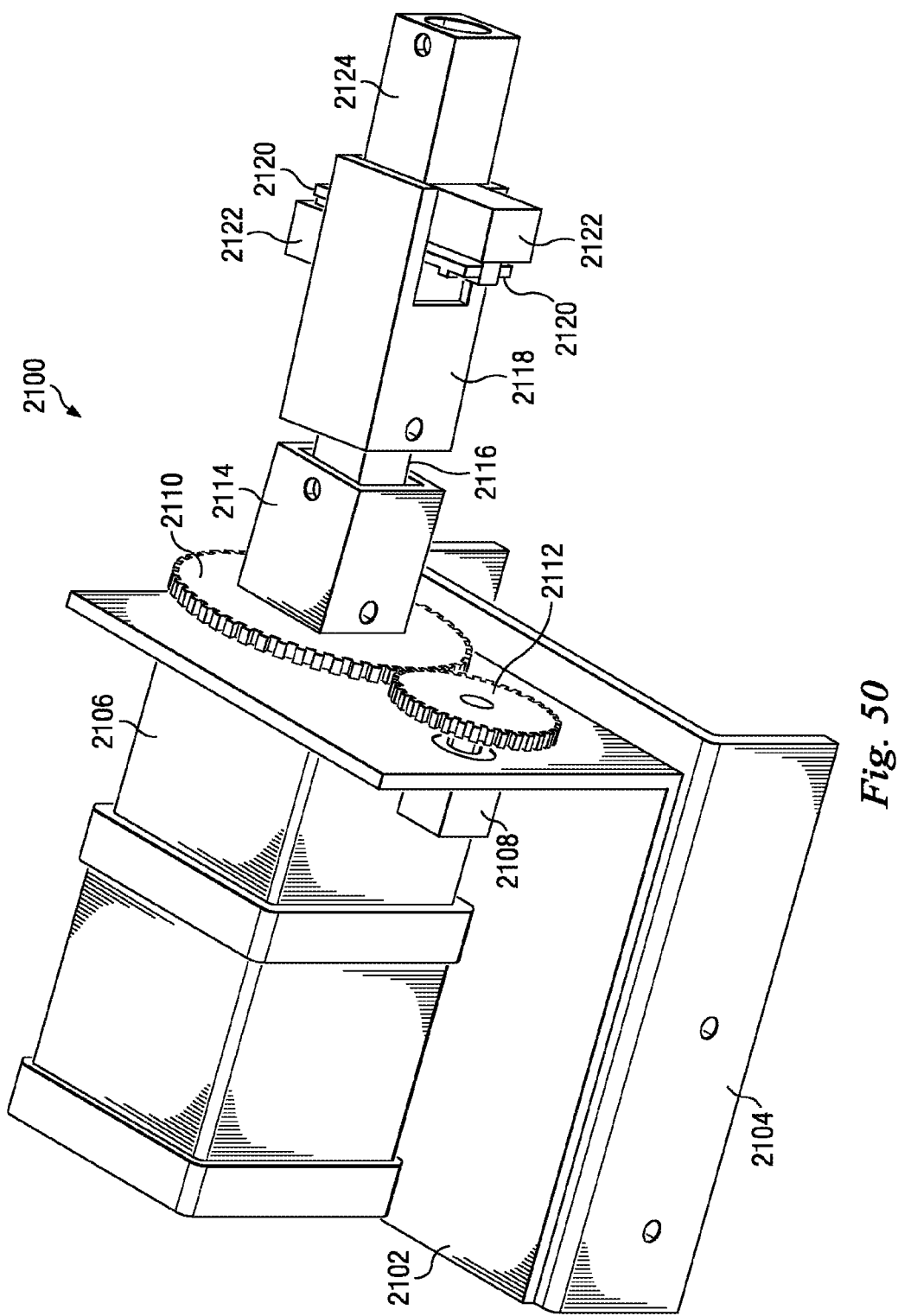
FIG. 50 is a diagrammatic perspective view of a delivery mechanism for use in a patient simulator according to one embodiment of the present disclosure.

Referring now to FIG. 50, shown therein is a diagrammatic perspective view of a delivery mechanism 2100 for use in a patient simulator according to one embodiment of the present disclosure. In particular, the delivery mechanism 2100 is configured for selectively rotating a fetal simulator, releasing the fetal simulator, and/or monitoring the force exerted on the fetal simulator as it travels through the birth canal. In some embodiments the delivery mechanism 2100 is configured to monitor the force exerted on the fetal simulator by a student or medical personnel during a simulated birth. The delivery mechanism 2100 includes a mounting plate 2102. The mounting plate 2102 is connected to a portion of the maternal simulator. In some embodiments, the mounting plate is connected via portion 2104 to a delivery mechanism configured to translate along the birth canal. In such embodiments, the delivery mechanism 2100 is configured to provide rotational movement to the fetus as the translational delivery mechanism translates the fetus along the birth canal.

The delivery mechanism 2100 includes a motor 2106. In some embodiments, the motor 2106 is configured to provide a rotational movement the fetal simulator. In other embodiments, the motor 2106 is configured to provide translational movement to the fetal simulator in addition to or in lieu of the rotational movement. In some embodiments, the delivery mechanism 2100 includes a potentiometer 2108 for monitoring the rotational movement of the fetal simulator. The potentiometer is connected to gear 2110 via gear 2112. As shown gear 2110 surrounds a swivel base 2114 such that as the swivel base 2114 rotates the gear 2110 rotates as well. The swivel base 2114 is associated with a swivel 2116 and swivel cap 2118 configured for imparting rotation to the fetal simulator. In some embodiments, the motor 2106 drives the swivel system causing the swivel 2116, swivel cap 2118, and swivel base 2114 to rotate. Accordingly, as the motor 2106 rotates the swivel components, the gear 2110 is also rotated causing gear 2112 to rotate. The rotation of gear 2112, in turn, is monitored by the potentiometer to determine the amount of rotation of the fetal simulator.

The delivery mechanism 2100 also includes a load cell 2120 and load cell supports 2122 for monitoring the force exerted on the fetal simulator during the birthing simulation. In that regard, the fetal simulator is securely attached to the delivery mechanism via attachment mechanism 2124. In some embodiments, the attachment mechanism 2124 is similar to that described with respect to FIGS. 24-27 above. Further, in some embodiments the engagement and disengagement of the fetal simulator to the attachment mechanism is controlled by a pneumatic valve located within the delivery mechanism 2100. In some embodiments, the pneumatic valve is controlled via a control system. Accordingly, in some embodiments a user or teacher can selectively release the fetal simulator from the attachment mechanism 2124. The secure connection between the fetal simulator and the attachment mechanism 2124 allows forces exerted on the fetal simulator to be transferred through the attachment mechanism and to the load cell 2120. In some embodiments, the load cell supports 2122 are positioned on either side of the load cell 2120 to prevent unwanted movement of the load cell. The amounts of force, torque, pressure, and/or derivatives thereof measured by the load cell 2120 are communicated to a control system in some embodiments. These measurements are then compared to an accepted standard to evaluate whether an appropriate amount of force was used in the birthing simulation.

Figure 51:
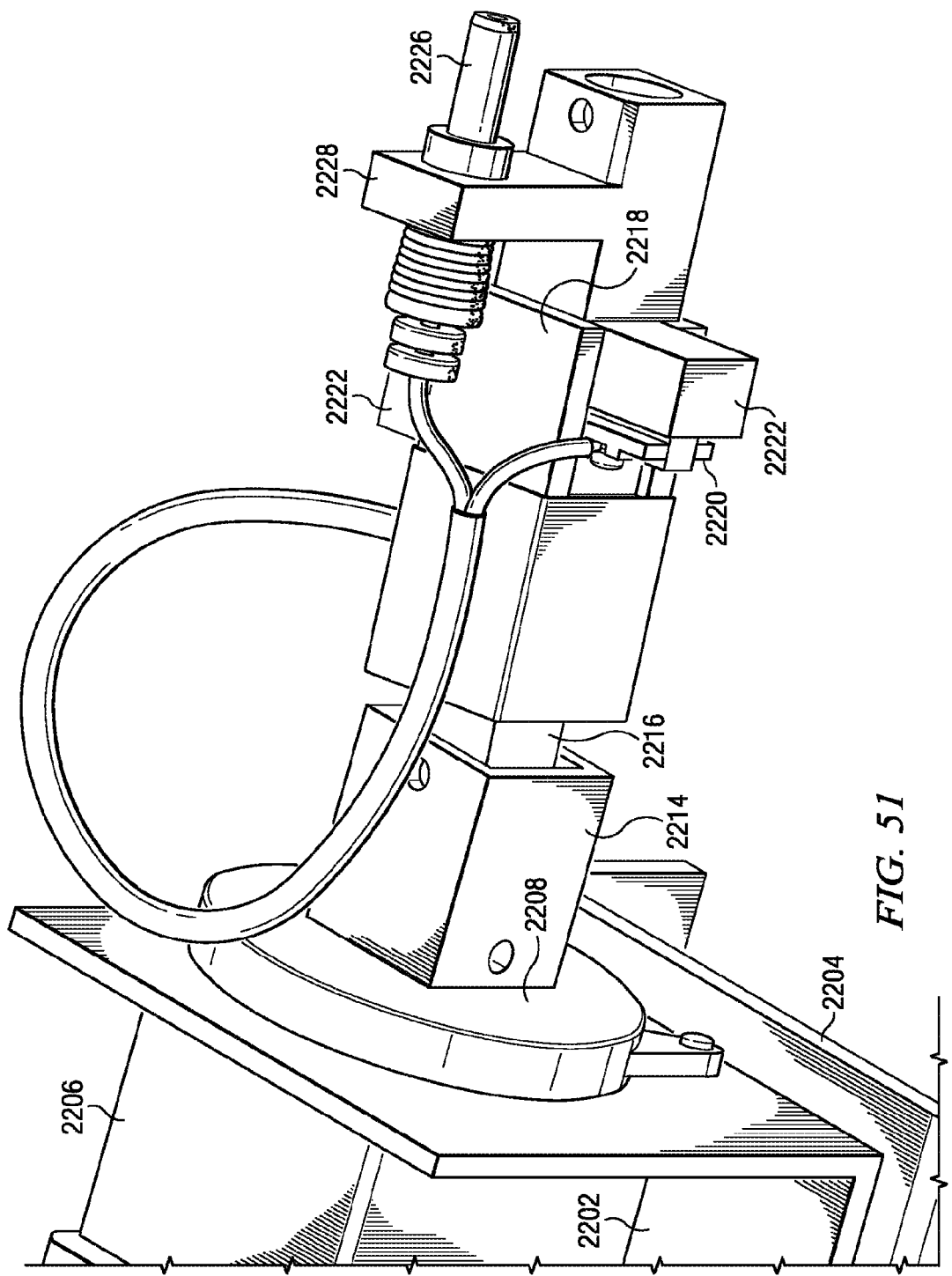
FIG. 51 is a diagrammatic perspective view of a delivery mechanism for use in a patient simulator according to another embodiment of the present disclosure.

Referring now to FIG. 51, shown therein is a delivery mechanism 2200 according to another aspect of the present disclosure. In particular, the delivery mechanism 2200 is configured for selectively rotating a fetal simulator, releasing the fetal simulator, and/or monitoring the force exerted on the fetal simulator as it travels through the birth canal. In some embodiments the delivery mechanism 2200 is configured to monitor the force exerted on the fetal simulator by a student or medical personnel during a simulated birth. The delivery mechanism 2200 includes a mounting plate 2202. The mounting plate 2202 is connected to a portion of the maternal simulator. In some embodiments, the mounting plate is connected via portion 2204 to a delivery mechanism configured to translate the delivery mechanism 2200 and/or the fetal simulator along the birth canal. In such embodiments, the delivery mechanism 2200 is configured to provide rotational movement to the fetus as the translational delivery mechanism translates the fetus along the birth canal.

The delivery mechanism 2200 includes a motor 2206. In some embodiments, the motor 2206 is configured to provide a rotational movement the fetal simulator. In other embodiments, the motor 2206 is configured to provide translational movement to the fetal simulator in addition to or in lieu of the rotational movement. In some embodiments, the delivery mechanism 2200 includes a sensor 2208 for monitoring the rotational movement of the fetal simulator. In some embodiments the sensor 2208 is similar to the rotation encoders 1228, 1336, and/or 1822 described above. The sensor 2208 is positioned adjacent to a swivel base 2214. The swivel base 2214 is associated with a swivel 2216 and swivel cap 2218 configured for imparting rotation to the fetal simulator. In some embodiments, the motor 2206 drives the swivel system causing the swivel 2216, swivel cap 2218, and swivel base 2214 to rotate.

The delivery mechanism 2200 also includes a load cell 2220 and load cell supports 2222 for monitoring the force exerted on the fetal simulator during the birthing simulation. In that regard, the fetal simulator is securely attached to the delivery mechanism via attachment mechanism 2224. In some embodiments, the attachment mechanism 2224 is similar to that described with respect to FIGS. 24-27 above. In the current embodiment, a power and communication connector 2226 is positioned adjacent to the attachment mechanism such that when the fetal simulator is engaged with the attachment mechanism the power and communication connector 2226 engages a connector of the fetal simulator to provide power and data transfers to the fetal simulator. In some embodiments, the communication connector 2226 is configured for 2-way communication with the fetal simulator. Also, in some embodiments a portion 2228 of the attachment mechanism 2224 serves as a ground for the connector 2226. In some embodiments the engagement and disengagement of the fetal simulator to the attachment mechanism is controlled by a pneumatic valve located within the delivery mechanism 2200. In some embodiments, the pneumatic valve is controlled via a control system. Accordingly, in some embodiments a user or teacher can selectively release the fetal simulator from the attachment mechanism 2224. The secure connection between the fetal simulator and the attachment mechanism 2224 allows forces exerted on the fetal simulator to be transferred through the attachment mechanism and to the load cell 2220. In some embodiments, the load cell supports 2222 are positioned on either side of the load cell 2220 to prevent unwanted movement of the load cell. The amounts of force, torque, pressure, and/or derivatives thereof measured by the load cell 2220 are communicated to a control system in some embodiments. These measurements are then compared to an accepted standard to evaluate whether an appropriate amount of force was used in the birthing simulation.

Although illustrative embodiments have been shown and described, a wide range of modification, change, and substitution is contemplated in the foregoing disclosure and in some instances, some features of the present embodiment may be employed without a corresponding use of the other features. It is understood that such variations may be made in the foregoing without departing from the scope of the embodiment. Accordingly, it is appropriate that the appended claims be construed broadly and in a manner consistent with the scope of the present disclosure.

What is claimed is:

1. A method for teaching patient care, the method comprising:
providing rotational and translational movement to a fetal simulator with a birthing mechanism disposed within a torso of a maternal simulator, wherein the birthing mechanism selectively engages the fetal simulator such that the fetal simulator is fixedly engaged with the birthing mechanism during the rotational and translational movement and disengaged from the birthing mechanism when the fetal simulator is to be removed from the maternal simulator.

2. The method of claim 1, further comprising dilating a cervix of the maternal simulator to simulate various stages of dilation.

3. The method of claim 2, wherein the cervix is dilated from about 2 cm to about 10 cm.

4. The method of claim 1, wherein the birthing mechanism fixedly engages the fetal simulator in a manner to simulate a breech delivery.

5. The method of claim 4, further comprising monitoring a force applied to the fetal simulator during a breech delivery simulation.

6. The method of claim 1, wherein the birthing mechanism fixedly engages the fetal simulator in a manner to simulate a normal delivery.

7. The method of claim 1, further comprising displaying fetal vital signs associated with the fetal simulator.

8. The method of claim 7, wherein the displaying the fetal vital signs includes synchronizing a fetal heart rate to contractions of the maternal simulator.

9. The method of claim 8, wherein the fetal heart rate is measured by an external fetal heart monitor coupled to the maternal simulator.

10. The method of claim 1, further comprising simulating maternal contractions with the maternal simulator.

11. The method of claim 10, further comprising monitoring the maternal contractions with an external contractions monitor.

12. The method of claim 10, wherein the simulating the maternal contractions includes varying air pressure in a tummy of the maternal simulator.

13. The method of claim 10, wherein the simulating the maternal contractions includes varying an intensity and/or varying an interval of the maternal contractions.

14. The method of claim 1, further comprising communicating data wirelessly between the maternal simulator and an external device.

15. A method for teaching patient care, the method comprising:
coupling a fetal simulator to a birthing mechanism of a maternal simulator;
engaging a locking mechanism of the birthing mechanism to fixedly secure the fetal simulator to the birthing mechanism;
utilizing the birthing mechanism to provide rotational and translational movement to the fetal simulator to simulate a birthing sequence; and
releasing the locking mechanism of the birthing mechanism to allow the fetal simulator to be removed from the birthing mechanism and the maternal simulator.

16. The method of claim 15, wherein the releasing the locking mechanism occurs based on a position of the fetal simulator within a birth canal of the maternal simulator.

17. The method of claim 15, wherein the locking mechanism automatically releases when the fetal simulator reaches a particular orientation and/or position within the birth canal.

18. The method of claim 15, wherein the releasing the locking mechanism occurs based on a release input from a user.

* * * * *